(12) United States Patent
Koblick et al.

(10) Patent No.: US 11,468,998 B2
(45) Date of Patent: Oct. 11, 2022

(54) METHODS AND SYSTEMS FOR SOFTWARE CLINICAL GUIDANCE

(71) Applicant: RADECT INC., Sharon, MA (US)

(72) Inventors: Yeshaya Koblick, Sharon, MA (US); Reuven Koblick, Sharon, MA (US)

(73) Assignee: RADECT INC., Sharon, ME (US)

( * ) Notice: Subject to any disclaimer, the term of this patent is extended or adjusted under 35 U.S.C. 154(b) by 389 days.

(21) Appl. No.: 16/596,267

(22) Filed: Oct. 8, 2019

(65) Prior Publication Data

US 2020/0111578 A1 Apr. 9, 2020

Related U.S. Application Data

(60) Provisional application No. 62/743,323, filed on Oct. 9, 2018.

(51) Int. Cl.
| | | |
|---|---|---|
| *G16H 50/70* | (2018.01) | |
| *G16H 70/20* | (2018.01) | |
| *G06N 3/08* | (2006.01) | |
| *G16H 10/60* | (2018.01) | |
| *G16H 80/00* | (2018.01) | |
| *G16H 50/20* | (2018.01) | |

(52) U.S. Cl.
CPC .............. *G16H 50/70* (2018.01); *G06N 3/08* (2013.01); *G16H 10/60* (2018.01); *G16H 50/20* (2018.01); *G16H 70/20* (2018.01); *G16H 80/00* (2018.01)

(58) Field of Classification Search
CPC ........ G16H 10/00; G16H 80/00; G16H 50/70; G16H 10/60; G16H 50/20; G16H 70/20; G16H 10/20; G16H 20/10; G06F 1/00; G06F 2221/00; G06Q 10/00; G06Q 2250/00; G06N 3/08; G06N 7/005; G06N 3/006; G06N 20/00
USPC .......................................................... 705/2–3
See application file for complete search history.

(56) References Cited

U.S. PATENT DOCUMENTS

| 10,881,463 | B2 * | 1/2021 | Mei ........................ G16H 50/50 |
| 2017/0124269 | A1 * | 5/2017 | McNair ................. G16H 50/20 |
| 2018/0293498 | A1 * | 10/2018 | Campos ................. G06F 8/311 |

FOREIGN PATENT DOCUMENTS

| EP | 2365458 | B1 * | 11/2017 | | |
| EP | 2365458 | B1 * | 11/2017 | ........... | G06F 19/322 |
| WO | WO-2016192612 | A1 * | 12/2016 | ............... | G06N 3/04 |

OTHER PUBLICATIONS

Levy-Fix et al., Machine Learning and Visualization In Clinical Decision Support: Current State and Future Directions, Jun. 6, 2019, https://arxiv.org/ftp/arxiv/papers/1906/1906.02664.pdf, pp. 1-42 (Year: 2019).*

Yu et al., Reinforcement Learning in Healthcare: A Survey, Aug. 22, 2019, https://arxiv.org/pdf/1908.08796.pdf, pp. 1-32 (Year: 2019).*

(Continued)

*Primary Examiner* — Joy Chng

(74) *Attorney, Agent, or Firm* — Tarolli, Sundheim, Covell & Tummino LLP

(57) ABSTRACT

Disclosed are methods and systems to aid medical practitioners with clinical decisions, in which recommendations and other information are derived utilizing a software reinforcement learning framework relating patient information to medical experiential case-files. The decision guidance systems and methods are applicable to medical and other applications.

18 Claims, 29 Drawing Sheets

(56) References Cited

OTHER PUBLICATIONS

Sohn, Ernest. Roski, Joachim, Escaravage. Steven, & Maloy, Kevin. "Four Lessons in The Adoption of Machine Learning in Health Care." Innovation in Care Delivery, May 9, 2017, http://www.openhealthnews.com/news-clipping/2017-05-09/four-lessons-adoption-machine-learning-health-care. Blog Article.

Jennifer Bresnick, May, 7 2018, "Health IT Analytics," Success of AI in Healthcare Relies on User Trust in Data, Algorithms, https://healthitanalytics.com/news/success-of-ai-in-healthcare-relies-on-user-trust-in-data-algorithms. News Article.

Ross, Casey; Swelitz, Ike, Sep. 5, 2017, "IBM pitched its Watson supercomputer as a revolution in cancer care. It's nowhere close", A Stat Investigation. Article.

Ravuri, et al. "Learning from the experts: From expert systems to machine learning diagnosis models", https://arxiv.org/abs/1804.08033 Journal Article Apr. 21, 2018.

Yuan Ling, et al., "Diagnostic Inferencing via Improving Clinical Concept Extraction with Deep Reinforcement Learning: A Preliminary Study." Proceedings of Machine Learning for Healthcare 2017, JMLR W&C Track vol. 68. Journal Article, Aug. 18-19, 2017.

Yuan Ling, et al., "Learning to Diagnosis: Proceedings of the the 8th International Joint Conference on Natural Language Processing, pp. 895-905, Taipei, Taiwan," Assimilating Clinical Narratives using Deep Reinforcement Learning. https://www.aclweb.org/anthology/I17-1090.pdf. Journal Article, Nov. 27-Dec. 1, 2017.

Luckett, Daniel, et al., "Estimating Dynamic Treatment Regimes in Mobile Health Using V-learning", https://arxiv.org/abs/1611.03531v2. Journal Article, Oct. 14, 2017.

Yuan Ling, et al. "Automated Clinical Diagnosis: The Role of Content in Various Sections of a Clinical Document", 2017 IEEE International Conference on Bioinformatics and Biomedicine (BIBM), 1004-101. http://www.sadidhasan.com/sadid-BIBM-role.pdf. Journal Article, Nov. 11, 2017.

Brown, N. and Sandholm, T. 2017. Libratus: Beating Top Humans in No-Limit Poker. Neural Information Processing Systems (NIPS). https://par.nsf.gov/servlets/purl/10077470. Journal Article.

Brown, N. and Sandholm, T. 2017. Libratus: The Superhuman AI for No-Limit Poker. International Joint Conference on Artificial Intelligence (IJCAI). https://www.cs.cmu.edu/~noamb/papers/17-IJCAI-Libratus.pdf. Journal Article.

Brown, N. and Sandholm, T. Jan. 2018. Superhuman AI for heads-up no-limit poker: Libratus beats top professionals. Science. 26. https://science.sciencemag.org/content/sci/359/6374/418.full.pdf. Book.

Mark Asch, Marc Bocquet, Maëlle Nodet: "Data Assimilation: Methods, Algorithms, and Applications", Society for Industrial and Applied Mathematics, ISBN 9781611974539, 2016.

Sutton, R. and A. Barto 1998. Reinforcement Learning: An Introduction. The MIT Press. ASIN: B015QL8B4O. Book.

Sohn, Ernest. Roski, Joachim, Escaravage. Steven, & Maloy, Kevin. "Four Lessons in the Adoption of Machine Learning in Health Care." Innovation in Care Delivery, May 9, 2017, http://www.openhealthnews.com/news-clipping/2017-05-09/four-lessons-adoption-machine-learning-health-care.

Jennifer Bresnick, May, 7 2018, "Health IT Analytics," Success of AI in Healthcare Relies on User Trust in Data, Algorithms, https://healthitanalytics.com/news/success-of-ai-in-healthcare-relies-on-user-trust-in-data-algorithms.

Ross, Casey; Swelitz, Ike, Sep. 5, 2017, "IBM pitched its Watson supercomputer as a revolution in cancer care. It's nowhere close", A Stat Investigation.

Ravuri, et al. "Learning from the experts: From expert systems to machine learning diagnosis models", Apr. 21, 2018, https://arxiv.org/abs/1804.08033.

Yuan Ling, et al., "Diagnostic Inferencing via Improving Clinical Concept Extraction with Deep Reinforcement Learning: A Preliminary Study." Proceedings of Machine Learning for Healthcare 2017, Aug. 18-19, 2017, JMLR W&C Track vol. 68.

Yuan Ling, et al., "Learning to Diagnosis: Proceedings of the the 8th International Joint Conference on Natural Language Processing, pp. 895-905, Taipei, Taiwan, Nov. 27-Dec. 1, 2017," Assimilating Clinical Narratives using Deep Reinforcement Learning. https://www.aclweb.org/anthology/I17-1090.pdf.

Luckett, Daniel, et al., "Estimating Dynamic Treatment Regimes in Mobile Health Using V-learning", Oct. 14, 2017, https://arxiv.org/abs/1611.03531v2.

Yuan Ling, et al. "Automated Clinical Diagnosis: The Role of Content in Various Sections of a Clinical Document", Nov. 11, 2017, 2017 IEEE International Conference on Bioinformatics and Biomedicine (BIBM), 1004-101. http://www.sadidhasan.com/sadid-BIBM-role.pdf.

Brown, N. and Sandholm, T. 2017. Libratus: Beating Top Humans in No-Limit Poker. Neural Information Processing Systems (NIPS). https://par.nsf.gov/servlets/purl/10077470.

Brown, N. and Sandholm, T. 2017. Libratus: The Superhuman AI for No-Limit Poker. International Joint Conference on Artificial Intelligence (IJCAI). https://www.cs.cmu.edu/~noamb/papers/17-IJCAI-Libratus.pdf.

Brown, N. and Sandholm, T. Jan. 26, 2018. Superhuman AI for heads-up no-limit poker: Libratus beats top professionals. Science 359. 26. https://science.sciencemag.org/content/sci/359/6374/418.full.pdf.

\* cited by examiner

METHODS AND SYSTEMS FOR SOFTWARE CLINICAL GUIDANCE

CROSS-REFERENCE TO RELATED APPLICATION

This application claims the benefit of U.S. Provisional Patent Application No. 62/743,323 filed on Oct. 9, 2018, and entitled METHODS AND SYSTEMS FOR SOFTWARE CLINICAL GUIDANCE, the entirety of which is incorporated herein by reference.

TECHNICAL FIELD

This disclosure relates generally to methods and systems for clinical guidance.

BACKGROUND

In recent years, there is a growing regional and global health disparity with regards to access to care and quality of care. This is exacerbated by a regional shortage of doctors. Medical practitioner knowledge, capacity, and efficiency using information technology is sought by providing a healthcare companion clinical support guidance as an aid in learning and decision making. The medical practitioners are seeking reinforcement in the areas of diagnosis, treatment, monitoring, prevention, and surgery from evidence gathering techniques from patient information, tests, exams, and review of other medical case-files including experiential learning from crowd sourced patient case-data.

There have been efforts for software to digitally learn and generalize patterns found in very large medical data sets, (i.e., machine learning) and choose the most likely relevant clinical concepts by means of software inferencing. There is no easy way to incorporate prior knowledge from existing literature or experts and the results cannot be quantitatively measured for accuracy. Meanwhile, matching patterns and finding clinical concepts rely on opaque reasoning considered a black box as to how decisions are derived using neural networks for e-systems to real-world clinical settings in such a way to offer useful clinical guidance.

The application to identify and treat patients as early prevention has been a promise of managed care for primary care to reduce hospitalizations, impact of chronic disease(s), and development or re-development of acute conditions. Nurses and primary care physicians currently do not have the longitudinal data analysis or clinical decision support information to offer useful clinical guidance for early prevention, and the longitudinal electronic health record to support early prevention analysis that is provided by the primary care practitioner or nurse.

Software to contextualize and reason the clinician understanding of the patient has been an outstanding challenge in the field of electronic health records that led software systems to inaccuracies.

SUMMARY

As one example, a guidance system includes a database to store a plurality of experiential case file data sets, each including at least one outcome and state-space parameters that represent an experiential state-space for a respective predetermined patient encounter associated with the at least one outcome. An index case file data set includes state-space parameters representing a state-space for a given patient. A reinforcement learning framework includes a master data set generator programmed to generate a master data set by combining the plurality of experiential case file data sets and the index case file data set into a flattened database of state-space parameters that represents an aggregate state-space for the plurality of experiential case file data sets and the index case file data set. The reinforcement learning framework also includes a learning identifier calculator programmed to compute a learning identifier that includes a set of common factors based on applying the given index case file with respect to the master data set. Each of the common factors in the learning identifier includes a weight/score that is calculated to quantify a measure of similarity of each common factor in a current index state-space of index case file data set and the aggregate state-space of the master data set. The reinforcement learning framework also includes an action interface to receive the one or more user-defined actions and/or set the predetermined policy. The learning identifier calculator is to recalculate the learning identifier in response to one or more actions that cause changes in the state-space parameters for the index case state-space, corresponding to a pathway of at least one state change from the current index state-space to a next state-space based on the scored common factors determined by the learning identifier and the predetermined policy data and an action parameter describing the at least one state change. An output device is to display user feedback representing at least one of an indication of an expected outcome, a proposed decision and a proposed intervention according to at least one of the current index state-space and the next-state space for the given patient.

Another example provides or more non-transitory computer-readable media having instructions programmed to perform a method. The method includes storing in memory a plurality of experiential case file data sets, each including at least one outcome and state-space parameters that represent an experiential state-space for a respective predetermined patient encounter associated with the at least one outcome. The method also includes storing in memory an index case file data set that includes state-space parameters representing a state-space for a given patient. The method also includes generating a master data set by combining the plurality of experiential case file data sets and the index case file data set into a flattened database of state-space parameters that represents an aggregate state-space for the plurality of experiential case file data sets and the index case file set. The method also includes computing a learning identifier that includes a set of common factors based on applying the given index case file with respect to the master data set, each of the common factors in the learning identifier including a weight/score that is calculated to quantify a measure of similarity of each common factor in a current index state-space of index case file set and the aggregate state-space of the master data set. The method also includes receiving at an action interface the one or more user-defined actions and/or set the predetermined policy. In response to one or more actions that cause changes in the state-space parameters for the index case state-space, the method also includes recalculating the learning identifier corresponding to a pathway of at least one state change from the current index state-space to a next state-space based on the scored common factors determined by the learning identifier and the predetermined policy data and an action parameter describing the at least one state change. The method also includes displaying on an output device user feedback representing at least one of an indication of an expected outcome, a proposed decision and a proposed intervention according to at least one of the current index state-space and the next-state space for the given patient.

Figure 1:
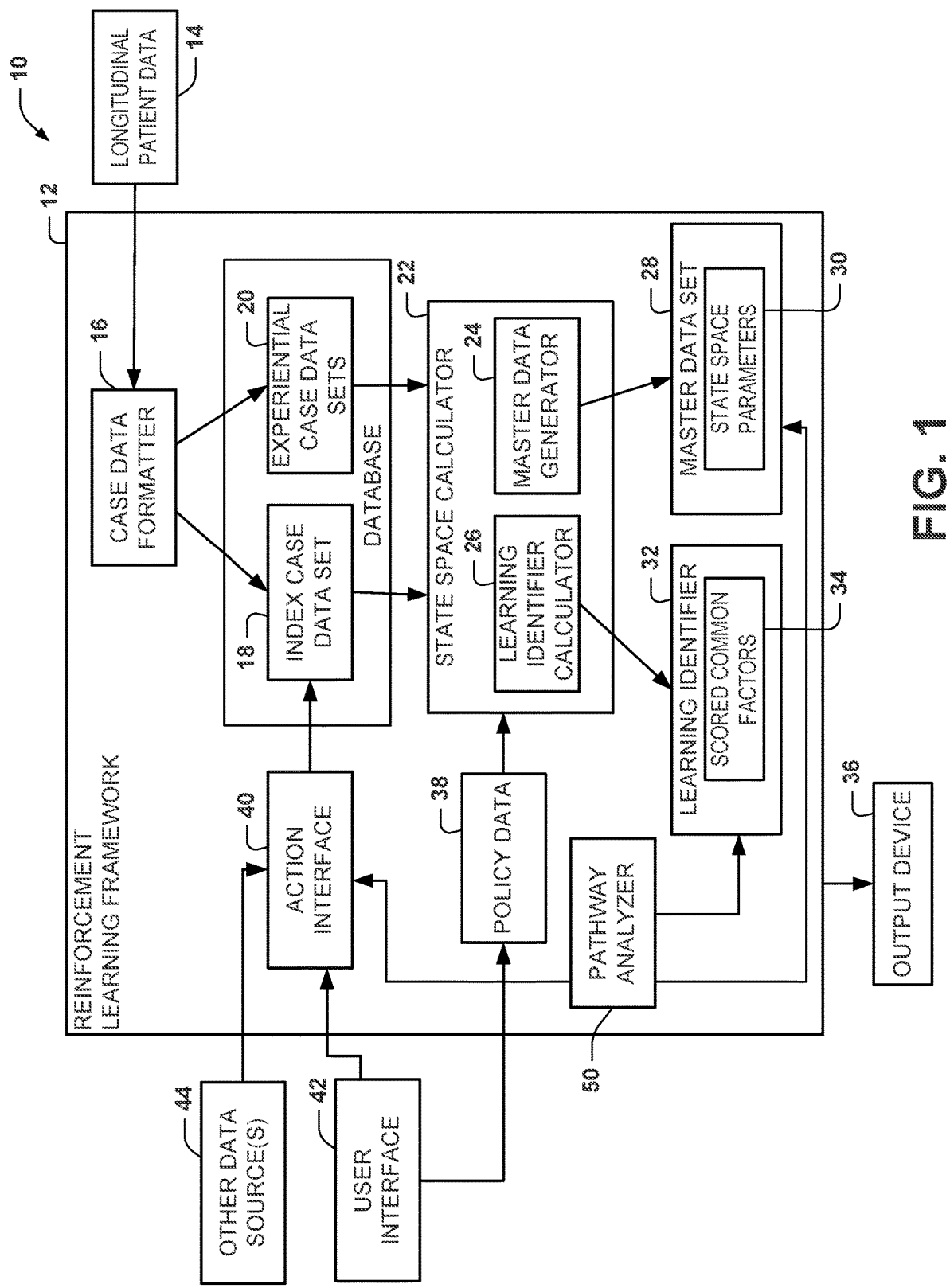
FIG. 1 depicts an example of a system implementing a reinforcement learning framework.

This application also includes Appendices 1 and 2 that contain further examples of various parts of the system and methods disclosed herein, including pseudo code for several methods and functions disclosed herein.

DETAILED DESCRIPTION

Overview

Methods and systems for clinical guidance are disclosed that perceive, reason, and explain medical knowledge from non-rule based software in order to ascertain medical information from data assimilation. The only rules is the reinforcement learning policy, which can be defined and stored in memory as policy data by the medical practitioner, clinic/hospital, and the like. The policy can identify hypothesis testing (e.g., also referred to herein as exploitation) or by searching (also referred to herein as exploration) of medical information from past and forward results, such as, experiential case-file data, to that of the index case-file data for a given patient.

The methods and systems disclosed herein utilize a reinforcement learning framework and a learning identifier programmed to generate a testing hypothesis and/or implement searching to score common factors of similar patient cases. The methods and systems can operate within diagnosis, treatment, and prevention, prognosis, provide differential, and compare hypothetical outcomes to a selected policy or patient what-if scenarios. There is decision causality, which can be ascertained with enough confidence to acquire outcome scenarios. This is opposed to probability and distributions used in some existing approaches that guide an outcome where some information may be correlative and others less so or even non-correlative.

The learning identifier is a composite of common factors within a pool of similar case-files selected from the entire body of experiential case files, where all are compared against a single index case. The greater the number of common factors, the more similar the cases. Once the learning identifier is derived, it can reveal potential information about the index case. The learning identifier when applied to policies, guides decisions as to what are the similarity of experiential case files for medical criteria, quality control/assurance for a particular longitudinal health variable, cost of medications, etc. As used herein, Longitudinal data refers to any health relevant information stored in electronic health record over short or long periods of time. For example, the electronic health record (EHR) is a specific longitudinal electronic record of patient health information generated by one or more encounters in any care delivery setting. Wireless monitoring of a patient is another specific longitudinal data source by measuring patient information over time.

'Experiential case files refer to a collection of patient electronic health record information stored one or multiple computers, such as distributed servers. The system can compare the learning identifier using policies to other cases in order to determine how well the outcomes fit other learning identifiers with different policies, such as, how well the processes, policies and/or guidelines for one organization might work for another. In some examples, the experiential case-files are stored in a public/private distributed ledger (e.g., blockchain). This is where information is transferred by a user, such as in a secure manner using known public-private key when sent from distributed sources, such as sensors, moving EHR case data, and the like.

The clinical guidance code disclosed herein is programmed to update the learning identifier from each new decision and health information in the form of an electronic health record that is operative to guide the clinician in making new decisions. The clinical guidance is programmed to discern properties of the learning identifier and perform analysis of the learning identifier properties. In an example, the clinical guidance displays on the user interface the learning identifier, the learning identifier properties, and analysis of the learning identifier properties. The learning identifier requires a minimalist set of states of electronic health information (e.g., stored in memory as EHR data) that need to be known beforehand, which is the amount of health and medical information initially given by the patient before the medical practitioner can start to diagnose or treat. In an example of minimalist states of information, a patient with heart pain would include the patient's family history, his/her patient history, procedures, vitals taken, objective questions answered about the heart pain and related pain, questions about the patient behavior, such tests for heart sounds, and EKG before the medical practitioner can consider the types of blood work, CT scan, Echocardiogram, etc. The minimalist set of states is an absolute form of exploration.

The clinical guidance can compare and identify when and how a transition occurs from exploration to exploitative, such as based on cost, outcome, and optimal pathways. Transition from exploration to exploitative is referred herein as turning points'. The exploration and resulting transition to exploitative may be based on patient information, tests, exams, diagnostic imaging, etc. For example, the clinical guidance is programmed to explore forward looking information, their learning identifier, and thus examines possible opportunities for treatment, patient monitoring, re-admittance and the like. The clinical guidance forward exploration is a non-rules based way of ascertaining future outcomes by the medical practitioner in order to decide, as an example, what would likely happen if a decision is made based on a particular diagnosis or course of treatment. Combining clinical guidance and medical longitudinal case-files from experiential learning from crowd sourced patient case-data provides a means for identifying early prevention diagnosis, treatment, and monitoring the objective alleviation and trajectories of the longitudinal data risk factors and population health metrics that is individualized for each patient. In consideration, the methods and systems are able to account for independent and dependent medical variables.

The clinical guidance system may further be programmed for capturing the contextual information and reasoning of the healthcare practitioner by evaluating what is the similarity of experiential case-files to clinical decision making of the healthcare practitioner. For example, the reasoning of information is useful to optimize billing, clinician (healthcare practitioner) notes. For another example, the reasoning is useful to collect useful clinical wireless health monitoring information to make informed decision about the patient diagnosis from several options. The use of the contextual information and reasoning from a nurse can be shared with primary care physician in a team based care setting about the patient social and environmental determinants.

In an example, the clinical guidance is integrated with one or more of health sensors, electronic mobile devices, and reading or directing information from mobile health sensors configured to gather case data. The clinical guidance may be used for educational purposes; as an example, by reviewing longitudinal medical case-files of a patient, by applying treatment to a given diagnosis which can be for particular time durations such as days, months, or years as the person experiences adolescence, mid-life, old age, etc. The clinical guidance further may be utilized to perform telemedicine by the medical practitioner and their attendee. This includes home healthcare and remote clinics serving as access points. The medical practitioner, for example, acquires patient information, performs tests and examinations in a controlled team-based care scenario where the guidance system is utilized. The information is sent, as an example, to computers in order to provide assessment, images, and other related information to other team members. They, in turn, can request information by means of the clinical guidance system. For example, team members can request and guide the medical practitioner, as an example, to perform an additional test, exam, etc.

In another example, guidelines can be created to determine when an attending medical practitioner will have to talk to the patient, or have enough information to make a diagnosis or offer treatment. The hospital or clinic or other governing body or committee (of one or more persons) can set the guidelines, which may be used to program policy data.

As another example, the clinical guidance uses a look behind and look ahead analysis using reinforcement learning by moving from one state to another or back in a state and generating a new learning identifier from the state space information that are displayed to the medical practitioner. The state space information for look behind is to go back a step and test what the learning identifier would be. The look ahead is a what if scenario of new medical information and what the learning identifier would be. For example, the outputs are visualized as a game-board that presents positions that describe how the board would change with new information (e.g., similar to a chess player replaying moves with new strategies).

By way of example, the state space is an array of states from state[0] to state[n], where n is a positive integer denoting a current state. It is possible to back up and create a new array such as state[0] to state[n-k] and from state [n-k] generate one or more new states given some desired outcome (e.g., also referred to as a testing hypothesis). Similarly, if the state space ranges from state[0] through state[k], it is possible to arrive at a hypothetical outcome (state[n]) by computing state [k+1] through state[n] with the goal of reaching such outcome (state[n]). The positions in the game-board are the indexes that range from 0 through n, where n represents an outcome and the index k represents the current state. The game-board visualization, for example, may be displayed using mobile app, desktop app, augmented reality, and the like. The state position uses one or more interactive visual cues (e.g., GUI elements) that are stationary and can be moved to create another position on the game-board, such as in response to user input or other data that is acquired. The data are labeled as former (previous) data assimilation, new data assimilation, when in diagnosis mode, treatment mode, turning points differential the minimalist states, etc. The GUI may represent the labels with different color, outline, an avatar, 2D or 3D image, or a combination thereof, such as to differentiate between different types and states of information presented on the GUI.

As another example, the clinical guidance is configured to provide the learning identifier pathways for testing hypotheses. The medical practitioner can visualize the potential next steps, and what would be turning points differential and the like, such as may be visualized from their input or the visualization may be generated automatically. A clinical guidance analyzer may be programmed to observe look ahead pathways and look behind to set new pathways from learning identifiers with new state space information. The clinical guidance analyzer may search for evidence based guidelines in treatment, and diagnosis by testing potential outcome results from the learning identifier pathways. The clinical guidance analyzer can also account for testing time intervals associated with a given pathway or patient condition.

As another example, the clinical guidance software includes a reasoning identifier that is programmed to contextualize the healthcare practitioner decisions made by observing from the learning identifier which case files are similar from updating the learning identifier, and capturing the exploration and exploitative behavior of the case file, as well as, what is considered different from the similarity of the case file. The reasoning identifier derives from the observation how the index case file relates to what is similar and not from the similar experiential case files. The reasoning identifier is programmed to use the contextualized decision information to derive the reasoning of the clinician, and generate a contextual description of the electronic health record of the patient behavior, measurements, and how this is evaluated by the medical practitioner. The reasoning identifier may also generate an action or command (e.g., machine readable instructions) that may be executed in response to a user input to operate on the contextualization for the index patient data. The healthcare practitioner reasoning of a case-file can be shared across team based care. This reasoning can be updated by the case-file being updated by another healthcare practitioner in the team based care.

This disclosure further relates to methods and systems that use data assimilation information in a reinforcement learning framework to score common factors using a learning identifier from aggregate experiential case-files; and from such data extraction, organize the sub-environments and environment. Experiential case-files refer to positive feedback from patient outcomes, and additionally execute predictive data assimilation steps from positive feedback of patient outcomes. The experiential case-files provide utility are for discovering, learning, and providing a (testable) hypothesis about a set of conditions, such as a diagnosis, treatment, monitoring, and prevention by means of the learning identifier.

As an example, the experiential case-files collect negative feedback to discover, learn, and perform hypothesis testing (e.g., exploitation) about a condition. The experiential case-file information provides a beneficial for look ahead of data assimilation from scoring common factors within experiential case-files to determine from wrong directions and/or bad hypothesis, i.e., continue giving tests, exams, that have high score common factors, but may be a bad hypothesis, i.e., leading to an undesired outcome. This is a particular challenge of clinical guidance. The experiential case-files describe the amount of data assimilation in learning about the patient conditions or non-conditions. This helps in testing how much data assimilation is needed and when it is required for a patient. The experiential case-file can have triggers built into it that cause the learning identifier to perform some action. The experiential case-files can be dynamic, and not just passive. For example, the experiential case files can have tags to search information from experiential case files. The tag can provide an interactive note that is displayed (e.g., a GUI), like the software to ask questions to the doctor and/or it can invoke an agent based on the doctor diagnosis, then seek out information automatically. The experiential case-files from notes further can trigger queries to be presented to the doctor based on the experiential case-files by using tags of notes.

Example Embodiments

Turning to the figures, FIG. 1 depicts an example of a clinical decision guidance system 10 that includes a reinforcement learning framework 12. In this example, the guidance system 10 and framework 12 are described in the context of medical information. In other examples, systems and methods disclosed herein are extensible to other contexts such as may include finance, banking, insurance, advertising, agriculture, psychology/mental health, education, biotechnology, engineering, or any related data that can be describe as experiential case files with a codified and taxonomy language.

The reinforcement learning framework 12 of the system includes a database to store a plurality of experiential case file data sets 20. Each case file set includes at least one outcome and state-space parameters that represent an experiential state-space for a respective predetermined patient encounter associated with the at least one outcome. The system 10 also includes an index case file data set that includes state-space parameters representing a state-space for a given patient.

As an example, the index case data set 18 and the experiential case data sets 20 can be constructed from longitudinal patient data 14. The longitudinal patient data can be stored in one or more data repositories, such including electronic health record (EHR) repositories. For example, the set of longitudinal patient data 14 may include structured and unstructured medical data stored in one or more EHR repositories that are accessible by the framework 12. In other examples, data sets may be provided separately or otherwise accessible for providing the longitudinal patient data 14.

A case data formatter 16 is programmed to process the longitudinal patient data 14 for generating the index case data set 18 and experiential case data sets 20. For example, the longitudinal data 14 can be cleaned, filtered and re-structured to provide the index case data set and the experiential case data sets 20, such as organized according to a schema. The data further can be normalized according to a standard, such as by utilizing dictionaries, a predefined ontological frameworks and the like to store the data in a consistent manner to facilitate processing by the framework 12.

To this end, the framework 12 includes a state space calculator 22 that is programmed to generate and construct an aggregate state space based on the index case data set 18 and experiential case data sets 20 according to policy data 38. For example, the state space calculator 22 includes a master data generator that is programmed to generate a master data set 28. For example, the master data generator 24 is programmed to generate the master data set 28 by combining the plurality of experiential case file data sets and the index case file data set into a flattened data space of state parameters that represent the aggregate state space for both the index case data and experiential case data sets. As an example, the flattened database of state space parameters is stored in a data structure such as in the form of a matrix of state space parameters. A matrix may be a two-dimensional matrix or it may be a higher dimensional matrix. An example of the matrix is as follows:

array([['chest', bilaterial-lower-extremity', retrosternal-chest', 'precordial-chest', 0, 0, 0, 0],
['3-minutes', 'episodic', 'continuous', 'activity', 'minutes', 0, 0, 0],
['tearing-chest', tearing', elephant-on-chest', pressure', 0, 0, 0, 0],
['10', 0, 0, 0, 0, 0, 0, 0],
['exertion', 0, 0, 0, 0, 0, 0, 0],
['severe', burning', significant', 0, 0, 0, 0, 0],
['lower-back', 0, 0, 0, 0, 0, 0, 0],
['sudden', 0, 0, 0, 0, 0, 0, 0],
['nausea', 0, 0, 0, 0, 0, 0, 0],
['arm-neck', 0, 0, 0, 0, 0, 0, 0],
['at-rest', fevers', dizziness', shakes', chills', 'palpitations', syncope', dyspnea'],
['none', antacids', activity-cessation', 0, 0, 0, 0, 0],
['edema', 0, 0, 0, 0, 0, 0, 0],
['feet', calves', 0, 0, 0, 0, 0, 0],
['sharp', severe', 0, 0, 0, 0, 0, 0],
['acute', 8/10', 0, 0, 0, 0, 0, 0],
['lower-back', 0, 0, 0, 0, 0, 0, 0],
['continuous', 0, 0, 0, 0, 0, 0, 0],
['increasing', 0, 0, 0, 0, 0, 0, 0],
['lifting weights', 0, 0, 0, 0, 0, 0, 0],
['at-rest', exertion', 0, 0, 0, 0, 0, 0],
['3-months', 3 years', 0, 0, 0, 0, 0, 0],
['rests', 0, 0, 0, 0, 0, 0, 0],
['30 min', two-hours', 0, 0, 0, 0, 0, 0],
['long-distances', 0, 0, 0, 0, 0, 0, 0],
['both-legs', 0, 0, 0, 0, 0, 0, 0],
['pattern', 0, 0, 0, 0, 0, 0, 0],
['intermittent', 0, 0, 0, 0, 0, 0, 0],
['significant', 0, 0, 0, 0, 0, 0]], dtype=object)

As a further example, the state space parameters 30 in the master data set 28 for each of the index case data set 18 and each of the experiential data sets 20 can be stored as a hierarchical arrangement of ordered pairs of isomorphically mapped state space parameters such as maybe organized along one or more pathways. As used in this context, a pathway refers to a set of state transitions from a current or starting state space for the index case data 18 and the transitions from that space, if transitions may be look ahead for subsequent state spaces and/or look behind transitions from the current space for previous/preceding state spaces, to one or more subsequent state spaces. The learning identifier 32 and associated scored common factors are computed by the state space calculator 22 and stored in memory associated with each state transition (each state space) along a given pathway.

For example, the state space calculator 22 also includes a learning identifier calculator that is programmed to compute a learning identifier 32. The learning identifier calculator 32 applies the given index case file data 18 to the master data set 28 to store and retrieve the set of state space for the scored common factors 34, and where the scored common factors 34 are computed by the learning identifier calculator 26, that provide a measure (e.g., a weight or scored value) to quantify a similarity among each of the common factors for the current index state space of the index case file set 18 with respect to the aggregate state space of the master data set 28. The scored common factors 34 are stored in memory as part of the learning identifier for the given state space.

In an example, the state space calculator 22 can utilize policy data 38 to generate the learning identifier 32. The policy data can define a set of rules associated with a medical condition such as to describe one or more equilibrium strategies associated with a set of state transitions for each of a plurality of possible outcomes. For example, the policy may be part of the learning identifier that imposes a bias on the scored common factors. The bias can be looking first for life threatening (acute) case-files to perform differential diagnosis first, or find the least redundant tests and exams to find between two exploitative pathways (two conditions). The policy further is an instruction, which can execute a search, to identify what to score the common factors. The policy can be, if certain results are defined by the scored common factors, to act on this information with an action, such as, perform tests as a next state to examine potential life-threatening case files first before non-life threatening case files. Additionally, one part of the policy can impact another policy. For example, one rule of a given policy can override a rule of another policy. As another example, a rule defined by such policy is learned by the scored common factors and causes a second policy to add an instruction of scored common factor results (e.g., to provide an alert or other notification for better understanding the relationship between policies).

The reinforcement learning framework 12 also includes an action interface 40 to implement one or more actions with respect to the current state space. For example, the action interface 40 can receive a user input or other data 44 from health mobile data, medical device, wireless monitoring, and the like to implement a change in the current state space, such as by changing (e.g., adding, deleting or otherwise modifying) one or more state space parameters in the index case state space. In response to changing the state space in this way, the learning identifier calculator 26 is programmed to recalculate the learning identifier 32 and scored common factors 34 for the new (e.g., updated) state space. For example, the transition from one or more previously generated state spaces to the new state space, which may involve modifying, adding or removing state space parameters from a current state space, defines a pathway. The pathway thus includes the set of one or more state transitions caused by actions that modify the index case data to connect a series of state spaces. For each new state space, the learning identifier calculator 26 computes the learning identifier and scored common factors 34 that are determined for the new state space parameters and the predetermined policy data according to the action interface 40 effecting the at least one state change.

As an example, the learning identifier calculator 26 is programmed to apply an operator to evaluate (e.g., by correlation or otherwise) the current state space of the next (modified) index case file set with respect to the aggregate state space of the master data set 28. The learning identifier 32 also includes a scoring function that is programmed to compute each of the scored common factors 34 for the learning identifier 32. In this way, the learning identifier 32 includes scored common factors 34 to indicate a reward in the reinforcement learning framework 12 that is associated with the implemented action that causes a transition from a current (or other preceding) state space to the new state space according to the changes implemented on the index case data set 18. The reward may be implemented in the reinforcement learning framework 12 as a positive or negative reward.

As an example, the case data formatter 16 contains a growing medical glossary to relate the language of the experiential case data set 20 that is that includes structured specific terms that comprise a taxonomy. The medical glossary is codified by means of a hash, or some identification within the database. The database can contain any information that is structured in the form of the medical glossary. The terms in the medical glossary can have associated ontologies, user parts of speech, and contextual understanding based on known techniques of natural language processing. The medical glossary grows by new submissions. Each of the submissions are universal and may be specific to the user. The medical glossary includes references to type of environment, sub-environment, and sub-sub-environment being taught by the growing experiential case-files, to associate word usage and several contexts based on usage and sentiment.

As an example embodiment, the medical database can grow from a known set of words and context from an EHR database, online resources like Wikipedia medical pages, WebMD, and medical dictionaries, and the like. As another embodiment, the medical glossary is grown by doctor usage from voice recognition, and selecting items during an appointment using augmented reality, and collecting user notes from before, during and after and appointment. In a further example, the medical glossary grows by frequency of term usage by medical practitioner across larger case-files. The less frequent words are tagged by the medical practitioner as their usage and part of speech, which the medical practitioner includes the common usage of term as a synonym.

In some examples, the action interface 40 receives user input commands via a user interface 42, such as may be a graphical user interface (GUI), associated with a device that implements or is otherwise in communication with the reinforcement learning framework 12. For example, the user interface 42 may be implemented on a personal computer, desktop, workstation, a portable device (e.g., tablet computer, laptop or smart phone) or other form of input device. The user interface 42 may be used to set the policy data. Additionally or alternatively, the user interface may be used to change the index case data, such as for evaluating one or more pathways, such as disclosed herein.

In additional or alternative examples, the action interface 40 may be coupled to receive commands and/or data from one or more other data sources 44, such as through a corresponding API. The other data sources 44 can be implemented as an IOT device, such as an IOT sensor that may receive health data from a given patient. In other examples, the other data sources 44 may be an API to particular data (e.g., laboratory data, such as blood or other biological testing). In this way, the action interface 40 can implement changes into the index case data set for a given patient, corresponding to one or more state transitions.

In some examples, the index case data 18 and/or the experiential case data sets, each being longitudinal data, may be continually updated based on changes to the corresponding longitudinal patient data 14. Such changes can be propagated through the data formatter 16 into the index case data set and/or the experiential case data set for each respective patient—similar to how actions being imposed by the action interface 40 are propagated.

In some examples, the scoring function implemented by the learning identifier calculator 26 is programmed to compute the scored common factors for state parameters by measuring one or more of a frequency of a state space parameters between the master data set 28 and the index case data set, and/or the number of common factors between the index case data set 18 and the master data set 28. Other examples of scoring criteria are disclosed herein. Each time the action interface changes the index case data, such as in response to new data or explorative or hypothesis based changes, the state space calculator 22 recalculates the master data set and the learning identifier, including scored common factors, as disclosed herein, and the recalculated master data set and learning identifier are stored in memory.

In addition to propagating actual changes in patient data into the current state space (e.g., in response to new or updated data via the action interface 40 or updates in the longitudinal data 14), the action interface 40 can be used to implement explorative (e.g., hypothetical) changes in the state space. For example, the action interface 40 can receive instructions to modify the index case data 18. Such modifications result in transition from a current state space to a modified explorative state space, as reflected in the state space parameters 30. The instructions to modify the index case data 18 may be received in response to a user input via interface 42, such as during exploration. Additionally or alternatively, the action interface 40 may receive instructions to modify the index case data 18 automatically, such as based on policy data 38 or other means (e.g., from machine-readable instructions implementing pathway analyzer 50). For example, the action interface 40 can implement such changes as part of evaluation of one or more of look-ahead or look-behind pathways (e.g., by pathway analyzer 50 implemented by the framework 12), automatically and/or manually in response to a user input instruction.

By way of example, the pathway analyzer 50 is programmed to determine one or more state transitions from an initial state space (e.g., based on the state of the index case data set 18 and the master data set). The pathway analyzer 50 determines the state transitions that correlate to an explorative pathway based on the learning identifier 32 that is computed for each state space and corresponding transitions along the respective pathway. As an example, the pathway analyzer 50 is programmed to compute which actions, corresponding to a set of one or more state transitions, optimize the learning identifier based on the scored common factors for one or more explorative pathways. By analyzing the learning identifier and associated scored common factors for a plurality of different explorative pathways, the pathway analyzer can determine an exploitive pathway. The exploitive pathway thus can define a desired or hypothesized outcome associated with a given patient. The learning identifier for each state space along the pathway defines a reward for each transition, which when aggregated represent the total reward for the respective pathway.

As a further example, the pathway analyzer 50 may be implemented as program modules including a look behind pathway analyzer and/or a look-ahead pathway analyzer. The look behind pathway analyzer is programmed to analyze the state space for the initial index case data set by inverting the isomorphic mapping of state space parameters associated with a given patient with respect to state space parameters 30 in the master data set. That is, the look-behind pathway analyzer 50 removes one or more state-space parameters to determine a next state space and the learning identifier calculator 26 computes the scored common factors 34 to find similar experiential case files for each next state space along the look-behind pathway. The scored common factors determine the reward for the look ahead, look behind, and combination pathway analyzer associated with state transitions along the pathway and for the pathway in aggregate. The reward is computed by how similar is the decision hypothesis of the pathway, and ability to find pathway from the similar experiential case files for each next state by comparing the scored common factors from the last state using reinforcement learning methods, such as, temporal difference, direct policy search, error driven learning, and actor-critic methods known by those in the art. Signal processing time series analysis. The scored common factors 34 are assessed by pathway analyzer 50 determining how similar the scored common factors 34 are with respect to the different pathways using multi-agent system methods, which may be existing methods. The pathway analyzer 50 explores the reward to find a dynamic equilibrium for multiple next states.

Similarly, the look-ahead pathway analyzer (executed as part of the pathway analyzer 50) is programmed to analyze the state space for the index case data set by analyzing the mapping of state space parameters 30 associated with a given patient with respect to the entire master data set 28. For the example of look-ahead pathway analyzer, one or more state space parameters are added to generate a next state space. The learning identifier calculator 26 computes the scored common factors and reward for each next state space along the look-ahead pathway. The resulting scored common factors determine for each state space corresponds to the reward associated with state transitions along the pathway and for the look-ahead pathway in aggregate. The pathway analyzer may implement a combination of look-ahead and look-behind pathways, automatically or in response to a user input, to provide a corresponding set of state transitions and resulting explorative pathways.

As a further example, the pathway analyzer 50 may apply guidelines to the index case data set 18 through the action interface 40, which may be guided according to the policy data 38 as well as other data that may be generated in response to user interface 42 and/or information received via the other data sources 44.

As another example, a practitioner can employ the framework 12 to test one or more questions ahead of time to learn from the evolving experiential case-files 20 if certain information is then mapped or there are differences between the index case data 18 and the experiential case files 20. The results of the analysis (e.g., look-ahead analysis learning) can inform a practitioner learns of what differences exist in the patient based on their logic reasoning. This means that the framework enables a practitioner to input a hypothesis of the patient condition to the framework (e.g., via user interface 44) and have the analysis look ahead and learn what would lead this hypothesis to be wrong to look out for, and how this evolves as new information might be added about the patient.

The system 10 also includes one or more output devices 36 that can display, graphically, textually or otherwise, guidance that is derived from the reinforcement learning framework 12. The guidance may be in a form of suggestion one or more actions that maximize or otherwise optimize the scored common factors associated with transitioning one state space to another state space (e.g., representing an explorative pathway). In some cases, the user interface 42 may be implemented on the same device on which the output 36 is also provided. For example, the user interface can be providing an interactive graphical user interface that enables the user to select and modify guidance for other actions such as disclosed herein.

Unlike existing EHR systems, the systems and methods herein can use experiential case files to determine (e.g., learn) from the experiential case-file pathways as a property of the experiential case files to find diagnosis and treatment, such as to determine what a decision hypothesis is for the experiential case files, and provide notes that dynamically adjust based on patient feedback, such as, social and determinant information, response to medication, patient input information into a health app, or mobile health data, such as, medical device, health wireless monitor sensor and the like. For example, the analysis 50 can evaluate temporal characteristics in the experiential case files 20 and an index case 18. For example, analysis of experiential case files 20 can determine information about time effects from the experiential case-files to ascertain how time would affect the index patient based on the index case data 18.

As a further example, systems and methods herein also can learn from experiential case files 20 to direct a search, such as to investigate a decision hypothesis. As one example, the analyzer 50 can implement a search, for example, to find the cost of pharmaceuticals. For instance, the search can invoke an agent (e.g., computer-readable instructions running on server) that is programmed to send a request to pharmacies, request data from one or more IoT health sensors (e.g., other data sources 44), and/or to collect MRI information on these type of related experiential case files. The agent can further be programmed to perform a calculation via an equation based on learning certain known information in the state-space 30 and return the results to the analyzer 50. For example, an equation requires certain variables. The variables can be calculated (e.g., by state space calculator 22) as a next state in the state-state-space or analyzer 50 can further analyze the equation to lead to a new pathway. Additionally or alternatively, the equation can trigger calling another equation based on the results. The results of the calculation using the equation further may be embedded or linked to experiential case files 20.

Additionally or alternatively, state-space calculator 22 or analyzer 50 can seek certain environment, sub-environments, or sub-sub environments, etc., in the experiential case files. This may include, gathering evidence by sending an API request to another application or device (e.g., other data sources 44) and/or determining gaps in one or more experiential case files 20 considered pertinent for a given patient. For example, the state-space calculator 22 or analyzer 50 can based on the above learning, fill in the gaps or missing variables with corresponding data for a given patient. For example, a patient may leave certain details out of a patient record, but data that is stored as part of another case-file can be used to fill these gaps with corresponding patient data.

Systems and methods further can learn information from state-space analysis (e.g., by pathway analyzer 50) in the reinforcement learning framework 12 and then apply that learned information to a new experiential case-file 18. In this way, historical information can be used to update the experiential case file data 20 for a given patient to be used as part of the learning identifier.

The experiential case-file results can be applied to other experiential case-files as an example embodiment. For example, consider a robot being trained. If the robot learns to pick up a block and then build an object from a plurality of the blocks, it already learned how to pick up the object. This is the analogy used with learning from experiential case-file to then learn similarity of the index patient.

The examples describing FIGS. 2 through 29 and the appendices submitted herewith provide additional examples, generally in the context of clinical guidance, to demonstrate various features of systems and methods that are programmed (e.g., as computer-readable instructions, which are stored in one or more machine-readable media and executable by one or more processors) to implement a reinforcement learning framework and learning and reasoning within the framework, as disclosed herein.

Figure 2:
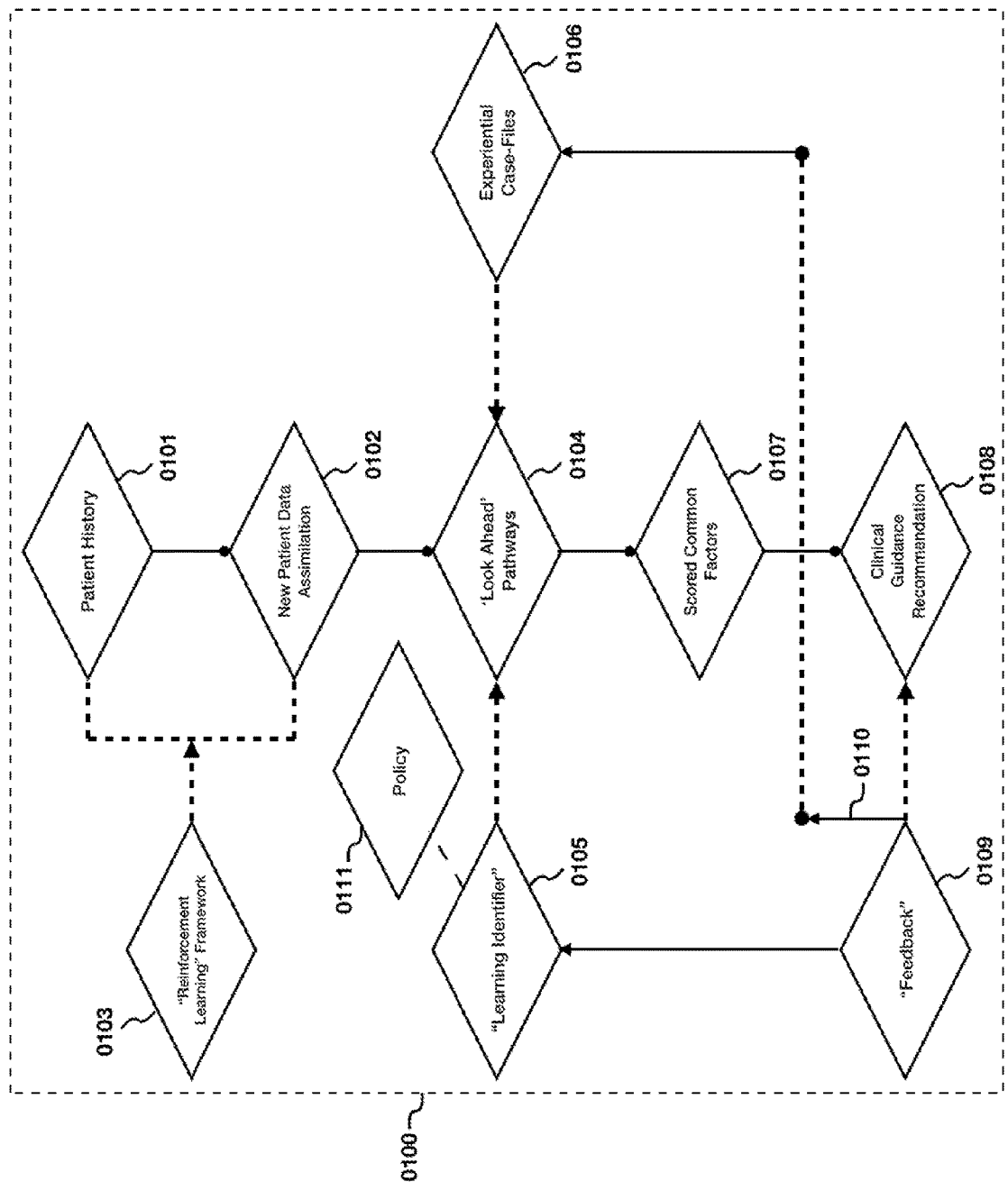
FIG. 2 is a flow-chart illustrating an example of Clinical guidance illustrating a basic operation: to find similarity of patient case with experiential case-files.

FIG. 2 is a flow-chart diagram that illustrates the clinical guidance system 0100 in which patient history 0101 (e.g., corresponding to case data set 18) is collected from EHR records, patient providing the information, distributed public/private ledger, and the like. New patient data assimilation 0102 is collected by at least one medical practitioner by means of test, exam, patient interrogation, diagnostic test, and the like, known by those in the art. The patient history 0101 and new patient data 0102 is recorded into a reinforcement learning framework 0103 as one state of an environmental system (called a state-space). The state is comprised of the environment, sub-environment, sub-sub-environment, etc., where this is accumulated from experiential case-files of the environment, sub-environment, sub-sub-environment, etc., by look ahead pathways of related case-files as potential new states as an evolving state-space (not illustrated in the figure). As disclosed, the reinforcement learning framework contain actions and rewards whose decision is to enter a new state either automated by clinical guidance or the prerogative of the medical practitioner.

As the look ahead pathways 0104 are observed with each new patient data assimilation (e.g., by the pathway analyzer 50), the learning identifier 0105 (e.g., corresponding to the learning identifier calculator 26) chooses pathways dependent on the polices, rewards returned, and action value functions chosen by the program. For example, both the look ahead pathways 0104 and the learning identifier (e.g., calculator 26) observe and operate on the experience case-files 0106 (e.g., master data generator 24). The look ahead pathways 0104 scores common factors 34 by similarity represented as the new patient data 0102 assimilation and look ahead pathways to offer the scored common factors 0107. The system 0100 automates a next state or states, and/or at least one medical practitioner's decision to make a clinical guidance recommendation at 0108 (e.g. from the output device 36). For example, the guidance recommendation 0108 includes patient information, further tests, exams, and the like, and the patient receives feedback 0109 as outcomes of the information, feedback, test results, etc. The learning hypothesis that explains prediction based on how the scored common factors were determined. The feedback 0109 then allows new patient data assimilation 0110 that is reviewed by the learning identifier 0105 (e.g., by calculator 26) and look ahead pathways 0104 (e.g., from the pathway analyzer 50) to score common factors based on similarity of the experiential case-files 0106. The information is recursive by cycling through new data assimilation to arrive at patient diagnosis, treatment, monitoring, and preventative, postoperative surgery, which may be output as the guidance recommendation at 0108. Such information is of common use by medical practitioners. We can incorporate exploration with new type of information like introducing a new pharmaceutical, or new medical data case-files.

The patient information and new data assimilation is stored in the reinforcement learning framework 0103, as well as the experiential case-files 0106 (e.g., case file data set 20). The patient data assimilation 0102 is considered a look behind'. The look behind and look ahead pathways 0104 are controlled (e.g., like a chess board) to observe pathways of the experiential case-files 0106. This analysis and clinical guidance recommendation 0108 can be graphed, such as by using programming data visualization tools using Python science stack libraries, Javascript d3.js, Tableau, and without limitation displayed in the form of a desktop app, mobile app, web app, and for use by video gaming platforms, such as Unity3D, Swift, and the like known by those in the art. In this way, the medical practitioner can visually review the steps of the patient history, new patient data assimilation, look ahead look behind scored common factors, related experiential case-files, the explanation of the clinical guidance recommendations, feedback from the patient outcome, and as graphs, gamification features, and integrative features, such as, voice recognition, noise sounds to indicate next steps, API into the gamification of health sensors. The gamification features are a network as a chess board, look ahead pathways visualized, and review of costs.

The learning identifier 0105 includes or is configured to access software agents that are programmed to compute next step in a pathway by means of one or more policies selected by algorithm or by the medical practitioner acting as an agent. The agent searches for guidelines, quality measurements, etc., with attributes that may be pre-configured. The agents can perform look ahead by experimenting different unselected policies. The agents are visually graphed individually for each agent. The graph analyzes the different policy scenarios which inform the medical practitioner what are the deviations and how they impact the patient case if pursued as next states.

The learning identifier 0105 can be implemented as including one or more software agents that can be defined or pre-selected by the medical practitioner. The software agent's behavior can be trained for a specific medical practitioner role. The software agents are both learn and integrate desired outcomes during practice.

The learning identifier 0105 as software agents are selected according to agent policy descriptors set forth by the medical practitioner, hospital, and possibly an insurance company. Policies can be changed in response to a user input, such as by medical practitioners having sufficient authorization within the system. A software agent would display the case as part of the user interface. The medical practitioner who would have to render an opinion by selecting user input from the case on the user interface. In certain circumstances, the medical practitioner can unlock a test or exam for another medical practitioner to perform.

The policy 0111 (e.g., corresponding to policy data 38) is rule based. The policy is pre-programmed. The policy also can suggest, as an example, the lowest cost next test from similar patient case-files, or what is the correct diagnosis. Policy is written and tested prior to use on small data-sets to verify correct behavior. As an example, the policy 0111 includes one or more of the following: i) medical criteria, described as guidelines for a particular clinic/hospital, medical practitioner, and inpatient or outpatient departments, medical curriculum, and optimal pathway, closest test to exploitative behavior, ii) quality assurance and control, which authorize a particular medical practitioner authority to prescribe medication (or not), perform acute case differential diagnosis, treatment to monitor if there are complications, and send a request to the patient, iii) a request that can link other software, such as, deep learning medical imaging, collect longitudinal data from IoT devices (e.g., sensors), send a software agent to search criteria of the web journal articles, perform analytics from another software, data collection needed by patient, schedule appointment, physiology information database, iv) to assign tasks like scheduling an appointment, review of certain medical practitioner by telehealth or ask a specialist a question for opinion or review, and collect commands from the Clinical guidance to perform a calculation, or that can be automated, and v) recommendations of analysis to the medical practitioner to review based on certain case-files, longitudinal data, such as, for a diabetic patient with weight gain. The policy defines a process or procedure that a hospital or clinic can build-in a specific requirement, such as to try lowest cost procedure. The policy also can suggest a lowest cost next test from similar patient case-files, or suggest what is the correct diagnosis.

As an example, policy 0111 is written and tested prior to use on small data-sets to verify the correct program behavior using training, validation, and testing data. The policy can be embedded in a particular diagnosis, treatment, prevention outcome, practitioner decisions, information in the environment, and within the sub-environment, such as time, diagnosis cost, results of one policy to dictate another policy.

As a further example, the experiential case-files is extensible for clinical guidance for readmission rates, patient conditions from becoming acute, longitudinal patient information by looking at similarity of experiential case-files for the behavior of longitudinal patients as case studies to prevent hospitalizations. The policy 0111 can include instructions programmed to perform an analysis to set or define risk factors that are updated based on readmission relationships of experiential case files for the index patient, population health related to the index patient condition, case studies developed as experiential case-files, and the like. Policies can establish requirements to compare multiple index patient conditions.

In some examples, the policy can be updated, like guidelines as disclosed herein. The update is a higher level command interpreter. It is believed this data is useful for inpatient and outpatient. As an example embodiment another example, the policy can be changed through exchange of information in a distributed public/private ledger (a more generalized blockchain).

The scored common factors 0107 (e.g., scored common factors 34) may differ from traditional machine learning, and include instructions programmed to implement counting, and more specifically, filters, statistical inference, and more specifically, deductive inference, frequency inference, group theory, set theory, topology/real analysis, statistical-Bayesian inference, and more specifically, temporal difference, fuzzy logic, vector calculus, topological mapping; that may include logical operations, Boolean algebra, decision theory, and dynamical systems, casual inference using medical rules, pre-computing look ahead outcomes, and the like. The scored common factors provide a way for the clinical guidance to be reviewed. The combinatorics of the state space, and each next state, or for look ahead can guide the scored common factor differential. The scored common factors can also use imitation learning, and dynamical systems approaches.

The experiential case-files 0106 (e.g., experiential case data set 20) can be stored on a single server, multiple servers, or across a farm of distributed of servers. To achieve high speeds across the experiential case-files are read by the learning identifier and scored common factors using multiple CPU, GPU, or a combination thereof, using multi-processing methods or multi-threading by those known in the art. The scale of computation as the experiential case-files are added to the system are in a meta-layer, with a speed-layer feeding the newly formatted information as gaps into the meta-layer, which may be copied common to known techniques in Big Data. This way, the copies allow for pre-computation of results. Copies of the meta-layer are tracked.

The experiential case-files 0106 grow and are stored into one or combination of databases. The experiential case-files 0106 may be sent to one or a combination of servers. For example, an intermediate speed layer includes the mobile device, augmented reality device, server, desktop app, or connectivity to any of these or other devices. The speed layer operates as recent data and is stored in intermediate storage with several speed layers generally distributed across several storage that then feed to a batch layer to manage updates to the master data. The master data can be stored in a server. The master data thus may be time-lagged from new information, due to latency throughout the system, so that every user access of the master data is the same and consistent. As a further example, the speed layer can have experiential case-file data stored across several hospitals or team based care centers, such as in one or more EHR systems. This reads to a larger meta-layer that is stored on a server.

The communication between the speed layer and meta-layer may be encrypted. The encryption may include patient information, medical practitioner information, such as, decisions, outcomes, patient notes, and information from evidence gathering, such as pharmaceutical cost information, or health sensor information. The evidence gathering information may be directly read by a speed layer, meta layer, or from a speed layer to the meta layer. Information is designated from the evidence gathering to kept long-term or short-term, and of saved on which platform, the medical practitioner device or server. The servers may be located at the hospitals or clinics or distributed. An example of short term is pharmaceutical cost information. The database include a central repository of experiential case-files that would compare results from the Clinical guidance with a particular EHR record, experiential case-files from a certain hospital or clinic, and data from particular medical practitioners.

The scored common factors 0107 (e.g., corresponding to scored common factors 34) may be tested if undesired outcomes are returned as a result of scored common factors. These factors will be placed in a database to be retested to understand patient outcome and scoring learning to update ways to improve scoring methods using the non-rule based algorithms. Part of the learning is an evaluation, for example, to determine if policy led to the poor approach using computational methods, or scoring methods were inaccurate, or if human error by the practitioner determining action led to error, i.e., hypothesis testing of the system, and stored decision making of tests, exams, etc., determined by the medical practitioner.

The scored common factors 0107 determine how the system came to a clinical decision by providing the ability to review the steps in clinical guidance. The steps in the clinical guidance is stored as part of the experiential case-file. As an example, the information can be integrated into a public/private ledger, and displayed using holomorphic encryption and the like to observe aggregate information without knowledge of the parties involved, with or without their explicit consent.

The explanation of the learning identifier 0105 can understand from the reinforcement learning based on the dynamic equilibrium of what the medical practitioner chooses as the next state. One example of the reinforcement learning framework 0103 is to utilize actor-critic methods by assessing f the medical practitioner if he/she is making the right decision when the system is utilized as a medical practitioner education tool from known testing data. In this way, the medical practitioner decision hypothesis can be reviewed and instructed by the curriculum or instructor themselves to update their course of action. The progress for the medical practitioner decision hypothesis may be plotted in a graph to demonstrate if the medical practitioner is learning. Another example learning identifier 0105 is a generalizer to learn by the system to repeat the methods of the medical practitioner to discover from similarity of case files and policies, and learning aspects, such as time-stamping. It can relate the generalizer to a way that the software can understand medical information. There may be competing generalizers to understand the medical information.

The scored common factors 0107 may use, as an example embodiment example, a comparison of results from casual inference to review the clinical guidance using machine learning neural networks, such as including, deep Q-learning, convolutional neural networks, recurrent neural networks, or a combination thereof, and whereby incorporating adversarial networks, and actor-critic methods.

The clinical guidance recommendation 0108 is programmed to determine from the hypothesis testing from the look ahead pathways 0104 what the medical practitioner's decision is. This is added to the index patient case data set 18 that is stored by the system.

The clinical guidance recommendation 0108 has uniqueness when accounting for differential for diagnosis and treatment. For example, the differential diagnosis and treatment analysis is implemented by clinical guidance recommendation 0108 can identify a test, exam, patient information, etc., that will recommend one or more actions, corresponding to state transitions, to improve the look ahead pathways 0104 and scored common factors 0107. In certain circumstances, the clinical guidance recommendation 0108 will add considerations in a differential, such as time aspect of a diagnosed STEMI and if a gated-CT should be taken to rule out an aortic dissection before performing a Percutaneous Coronary Intervention (PCI).

The feedback 0109 is the outcome of the patient that may be determined in one or more of the following ways: 1) patient, family member, healthcare aid, and other medical practitioners using a mobile descriptor of how the patient feels, 2) follow-up test and examination from a medical practitioner, 3) information from health sensory equipment, 4) diagnostic test, imaging, etc., and the like or a combination thereof. The patient outcome in the feedback 0109 is extensible to longitudinal data measurements. The outcome when defined is tagged to be uploaded into the speed-layer. The experiential case-file 0106 is continuous, meaning the case continues with further monitoring, but there are aspects of episodic states and, in such cases, may serve as another form of turning points'. The turning points are moving from monitoring to a condition diagnosis to treatment. Another aspect is surgery outcomes from a diagnosed condition as intermediary step of treatment and healing.

Figure 3:
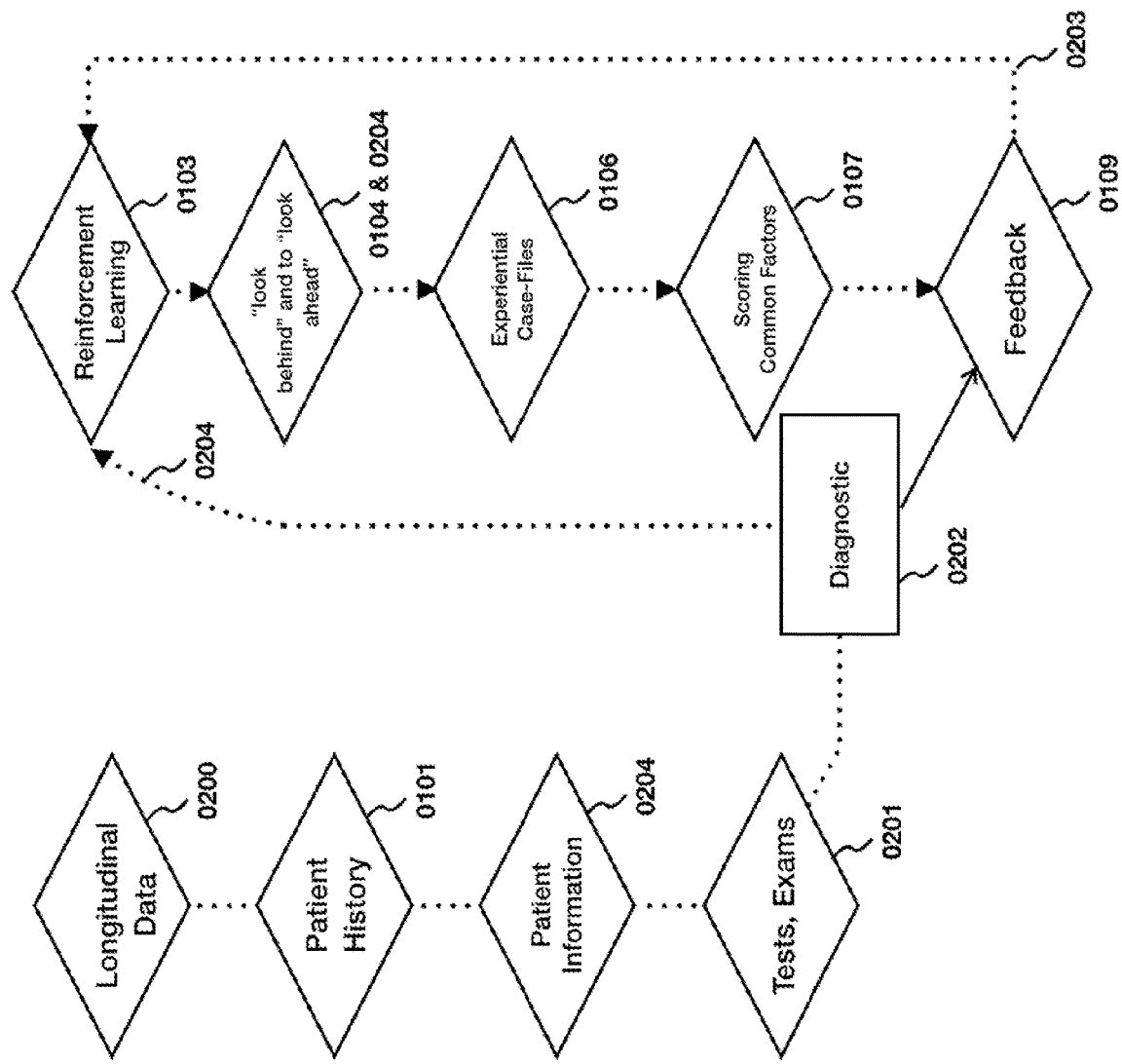
FIG. 3. is a flow-chart illustrating an example of Clinical guidance for integration of longitudinal data that monitor, relate, and potentially diagnose information relating to the index patient from similar experiential case-files.

FIG. 3 is a workflow diagram illustrating an example of monitoring longitudinal data 0200 to determine a diagnostic (or diagnosis, prognosis) 0202 to relate experiential case-file data to the index patient. As disclosed herein, a minimalist set of states is needed to execute clinical decision guidance, and the approach in FIG. 3 is an automated method programmed to determine the minimalist set of states for a given condition or decision hypothesis. In the example of FIG. 3, there is relationship of environment, sub-environment, and sub-sub environment, etc. from a state space from a decision hypothesis of the healthcare practitioner, identified similar experiential case-files 0106 by the healthcare practitioner to find a learning identifier, or the patient describing a health problem to indicate an exam based on longitudinal data 0200 from information generated that reads and writes the patient history 0101 and patient information 0203 (or next state) to find minimalist states of tests and examinations 0201 including a respective diagnosis 0202. The diagnosis is read to a reinforcement learning framework 0103 (e.g., from the reinforcement learning framework 12) as look behind and look ahead 0204 and 0104 by evaluating the experiential case-files 0106 that are scored by the common factors 0107 to propose another test with predictive feedback 0109. The predictive feedback 0109 determines a new reinforcement learning 0103 to recursively find the next state 0203. The diagnostic 0202 provides validation as predictive feedback 0109 of the index patient as a next state 0203 for the longitudinal data 0200, or if the longitudinal data is partially or not relevant (e.g., no longer relevant), then such data is sent to the reinforcement learning framework 0103.

As an example, the longitudinal data 0200, patient history 0101, patient information 0204, tests, exams 0201 and combination thereof medical information is acquired from the following, at least one health sensor, medical device, digital health app voice recognition by medical practitioner, nurse, home healthcare worker, or related, such as, patient or family member. The health sensor, medical device, or digital health app is configured to capture information and has a directed API to wirelessly transmit the medial information that writes as part of longitudinal data 0200 to the clinical guidance system 10 as other data source(s) 44. The longitudinal data 0200 can be specific to the patient electronic health record as the state space environment, sub-environment, sub-sub environment, etc., or a combination thereof written by the health sensor as other data source(s) 44. The clinical guidance system 10 using a directed API wirelessly transmit longitudinal data 0200 instructions to a health sensor, digital health app, and the like.

The longitudinal data 0200 is thus tracking patient information, tests, exams, imaging, etc., at different points in time, such as across any number of one or more patient encounters. This is a way to incorporate continuous learning or discrete learning of patient behavior, and to understand specific monitoring of the patient as longitudinal data 0200 and relate this to similar experiential case-files. The longitudinal data is more generally integrated by patient information from API to read in patient data. As an example, sensors (e.g., IoT sensors) may be placed in positions to record urinalysis information and have wireless access to transmit the data. Other types of signals may be captured and sent in other examples. As an example, the signal is automated and sent to a medical practitioner who reviews oversight of the sensor data. As a further example, a home health care worker that would take exams, tests, guided by the clinical guidance autonomously, and when an identifying signal that indicates a condition is observed from longitudinal data, such as, from health heart monitor to measure from longitudinal data arrhythmia, or social and environmental determinants input from a person written into a health app, a software agent that for example is an alert of a condition seen or derived from the longitudinal data 0200, or explanation the patient is gaining weight from the health app, will be sent to the attending doctor. This is a way to improve preventative care.

As another example, the clinical guidance is programmed to act autonomously to instruct the medical practitioner what next test, exam, etc., to perform by providing a recommendation for diagnosis, treatment, and monitoring. The recommendation may be sent to the attending medical practitioner. As yet another example, the attending medical practitioner determines the policies and/or adjusts the policies for the home healthcare worker to search for a particular condition. The example arises when a nurse in home health setting has a policy to perform tests, exams, and social and environmental, and from the data captured by the clinical guidance system 0100, the guidance system recommends a new policy for nurse to perform new tests, exams, and collect patient data, such that the clinical guidance works autonomously. The medical practitioner can additionally review the case-file from the clinical guidance system and accept or adjust the policy for what the nurse scope of practice for the particular patient case.

The reinforcement learning framework 0103 is autonomously placed in the patient environment, sub-environment, and sub-sub-environment by information type or category. The reinforcement learning framework 0103 is programmed to generate a growing state-space for the patient. The environment has to account for time prediction between the longitudinal data. This time-stamping is useful in establishing behavior of the signal when tests are performed. It also serves as a baseline of the patient, like how the diagnostic 0202 is modified.

The diagnostic 0202 may be implemented in new explorative pathways. The longitudinal data 0200 and diagnostic 0202 include sensory information from tests 0201, such as genomic tests, proteomic tests, molecular tests, microbiome information, medical tests using deep learning software, such as, medical ultrasound, skin cancer deep learning tests, and the like. The diagnostic 0202 can incorporate the sensory information as longitudinal data from population health studies of what if scenarios to request another test or patient information, such as for an early cancer diagnostic test. For example, information from the early cancer diagnostic may provide case study information that improves population health prediction based on test results. Also, the longitudinal data and diagnostic results may be directed to a surgery, wherein the clinical guidance system 0100 uses a clinical guidance recommendation 0108 by using a learning identifier and searching to find complications from patient information in post-operative healing from the experiential case files 0106. The clinical guidance system 0100 can identify both doctor and assisted the diagnostic tests integrated into the environment, sub-environment, sub-sub environment, etc.

As yet another example, experiential case-files 0106 may be kept as a data-set to compare, kept by the individual hospital and clinic, or a consortium of hospitals and clinics. The data generated will have their own encryption key and coding that will link each patient to the particular medical practitioner, hospital, and clinic. In this way, the data entered and sent by API to the appropriate endpoint for inpatient and outpatient services of patient records. For example, the encryption is a public/private key that use ECC and RSA standards. The clinical guidance system 0100 may use a quantum encryption and post encryption. The quantum encryption techniques to encrypt patient data include quantum key distribution (QKD), quantum commitment, quantum coin flipping, bounded and noisy quantum storage model, and position-based quantum cryptography. The post encryption may include lattice-based cryptography, multivariate cryptography, hash-based cryptography, super singular elliptic curve isogeny cryptography, symmetric-key based cryptography, code-based cryptography, physical quantum encryption techniques over optical and wireless communication, or a combination thereof. There can be a combination of entities who own the private keys by the patient, medical practitioner, and hospital and clinic. Each key may represents a particular unit of information of the patient, clinic, hospital, or connectivity of the hospital. A general experiential case-file database of patient records may be anonymized and obfuscated, such as its location may remain hidden.

Figure 4:
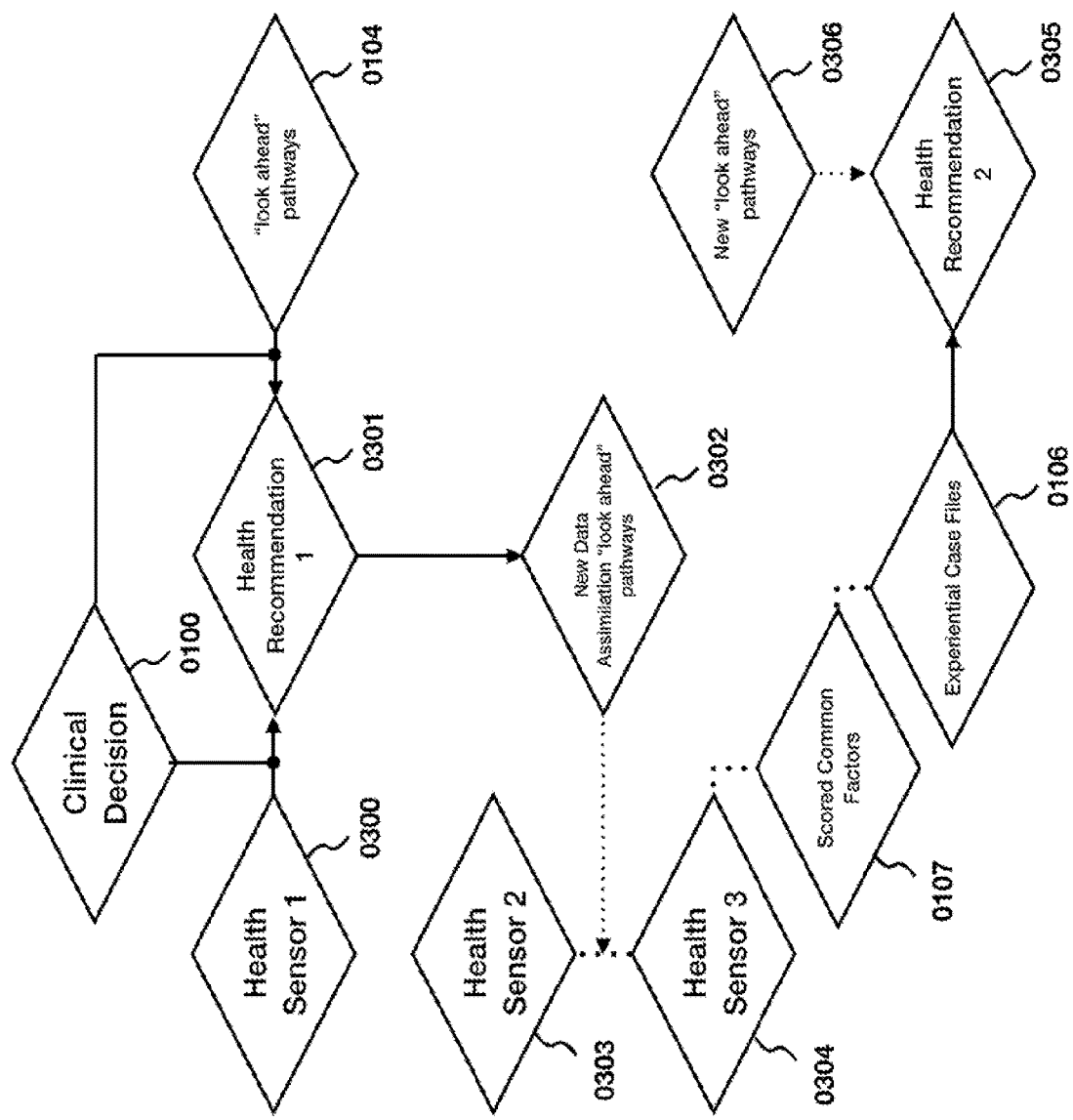
FIG. 4 is a flow-chart illustrating an example of Clinical guidance wherein evidence gathering utilizes hypothesis testing, or look ahead pathways to acquire new data assimilation.

FIG. 4 is a flow diagram illustrating an example of a first health sensor 0300 that is used by the clinical guidance system 0100 to provide a first health recommendation guidance 0301 from look ahead pathways 0104 as the testing hypothesis. In this example, the results are then needed to determine what the best next states to further differentiate the medical episodic outcome. From the learning identifier policy (not part of the illustration), the recommendation 0301 is used to determine from new data assimilation look ahead pathways 0302 that automate a second health sensor 0303 and third health sensor 0304. For example, the new data assimilation look ahead pathways 0302 activate sensors 0303 and 0304 to supply medical information (e.g., respective sensor data) read by the clinical guidance scored common factors 0107 from the experiential case-files 0106 to provide a second health recommendation 0305. Additionally, there is a new look ahead pathway 0306 to observe the optimal path for the most likely pathway. An example look ahead pathway 0306 that may be used to find the optimal path is counting the highest frequency of similar experiential case file outcomes from the look ahead pathway analysis. The objective of the look ahead pathways 0302 is for the medical practitioner to expand their own experiential training to that what is in the experiential case files, and observing the learning identifier to determine, which experiential case files are relevant to review.

The example of FIG. 4 describes a health sensor that is automated to run a test via an instruction provided via an API from the clinical guidance system 10. This is especially useful when monitoring a patient, or informing a nurse what to test, examine, etc. As an example, the nurse may not be experienced in a particular field of medicine and cannot competently perform a diagnosis, but knows how to run the required tests. This information can be prepared for an attending team-based care clinician. This further can be extended to where the health sensor can help with differentiation of the experiential case-files. The health sensor is not limited to a digital device, and include voice recognition, information typed into a computer and data sent wirelessly.

The new look ahead pathways 0306 are information (e.g., including state transitions) that relate information like a Chess game to recognize the combinatorics of information to similarity of information in sets experiential case-files 0106 by looking at how each next state creates a new learning identifier to find similarity of experiential case-files, such as in the same manner as a Chess game. As an example embodiment, there is a reverse of positions, where information does not predict the hypothesis testing from acquiring new known data assimilation, the system instead determines what predicted correctly from those tests as health information 1 0301 read by the clinical decision 0100 and, like starting a new game as new health recommendation 2 0305, is able to repeat the Chess board in the state-space data assimilation as new data assimilation look ahead pathways 0302, and re-testing the newly hypothesis testing as look ahead pathways 0306 from the new health sensor 3 0304 test that scores the commons factors 0107 to find similar experiential case-files 0106. The medical practitioner can request this information in basing a potential hypothesis testing or their own hypothesis testing using a new look ahead pathway 0306.

One or more health sensor 0300, 0303 and 0304 can be added to the system for purposes of back propagation. In this context, back propagation is termed look behind for purposes of adding data assimilation in a look behind pathway to determine if the prior steps predict the hypothesis testing. This is performed in such a way as demonstrating dynamical system approach to knowing the initial parameters of relevant similarity of the index patient and experiential case files that would result in an exploitative pathway were found. The look behind pathway may further be programmed to perform a perturbation of parameters by observing if adding an additional or reducing the parameters that does not find the diagnosis or provide treatment. This is a feature of imitation learning that may be implemented by the clinical guidance system 100. Every patient is different, but when certain initial parameters of the actual diagnosis or treatment, based on experiential-files are highly similar, such as at least 90 percent of all factors, then the information is predictive with high likelihood between new data assimilations. There are differences in the look behind that would then drift from the exploitative, such as a patient having the same diagnosis, but the dosage of medicine is different, because they have different weights. The turning points identify the differences for what is considered similarity between exploitative pathways, and to find the patient similarity in experiential case-files as decision hypothesis, or to refactor and find new turning points for other exploitative pathways. Each exploitative pathway has variables that define their turning points using look ahead by identifying the similar experiential case files for the exploitative pathway.

Figure 5:
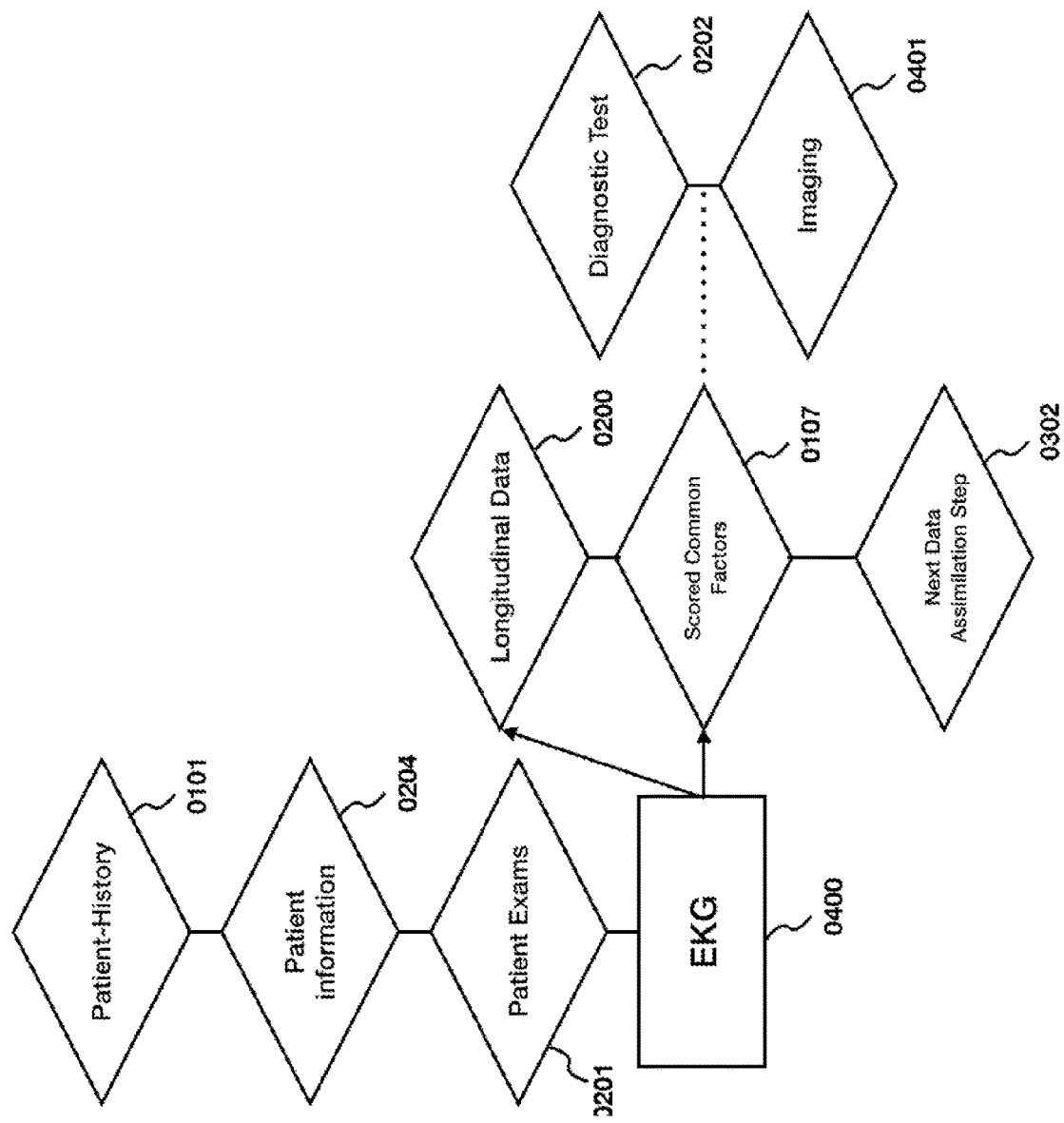
FIG. 5 is a flow-chart illustrating an example of Clinical guidance that illustrates a sub-environment example interpreting an electrocardiogram from patient data and similar experiential case-files coupled with the incorporation of longitudinal data within the sub-environment.

In FIG. 5 is a workflow diagram illustrating of an example of the clinical guidance system serving as a software learning tool to learn from sensor information. For example, the clinical guidance system is programmed to read by accessing and using data information by an electrocardiogram demonstrated at EKG 0400. The data additionally includes patient history 0101, including longitudinal data of the EKG 0400, and longitudinal patient information 0204, such as patient pain type, patient examinations 0201, such as, jugular venous pressure (JVC), and receive the (EKG) data, and this is read by the clinical guidance system 0100. The clinical guidance system can also read diagnostic test 0202, such as cardiac biomarkers, and/or imaging information 0401 requested by the medical practitioner. The scored common factors 0107 can further form information requests for the next data assimilation step 0302.

FIG. 5 is a workflow diagram illustrating an example scenario where the clinical guidance system is able to learn the behavior of health sensory information. In this example, the entire patient longitudinal history, including but without limitation heart pain, weight gains, abnormal heart sounds, social and environmental determinants, family history of heart failure, etc., is needed to make a decision of what the EKG reading is. The decision may be made by comparing from longitudinal data, patient information that would lead to a hypothesis testing of what the EKG was before reading it using data assimilation. For example, the hypothesis testing may be programmed as a search using a longitudinal learning identifier to find similar experiential case files that are relevant for patient history, longitudinal data, and environment, sub-environment, and sub-sub environment, etc., when trying to identify a similar hypothesis testing particular condition(s) from the EKG data. For example, the EKG reading 0400 can be compared with both patient information 0204 and longitudinal data 0200 where the scored common factors 0107 can try to predict the similarity of experiential case-files and longitudinal data 0200 to then explore the EKG data information to find decision hypothesis and send this information for the medical practitioner to run tests. As an example, wearable watch EKG digital health apps are slightly or lesser accurate than a 12 lead EKG, but have the ability to collect a lot more data health information for the medical practitioner to identify a patient heart condition. A 12 lead EKG can then be tested in a clinical setting.

As a further example, the scored common factors 0107 is programmed to determine index for patient information on multiple information sources. For example, the scored common factors 0107 can determined the index from same tests, such as direct reading of EKG, longitudinal data reading to EKG, and relationship of changes in the longitudinal patient information. In an example, the longitudinal data is dependent on the type of data read, such as whether the EKG is read from rest or the EKG is read from high exertion. This type of data differentiation may be generalized to any tests similar to the diagnostic 0202 demonstrated in FIG. 3, such as being genetic test, biomarkers, imaging, and the like known to those in the art. Next data assimilation step in the Clinical guidance system can recommend the evidence gathering of how tests learn from changes in patient vitals, blood pressure, and general patient information, such as, the clinical guidance system reading from the digital health app or guided by a healthcare practitioner a stress test in home environment and how patient reacts to specific stimuli, or effects of EKG applied exertion such as behavior of a stress test. This produces an additional scored common factors of the index patient, which are stored in memory for the index patient.

Figure 6:
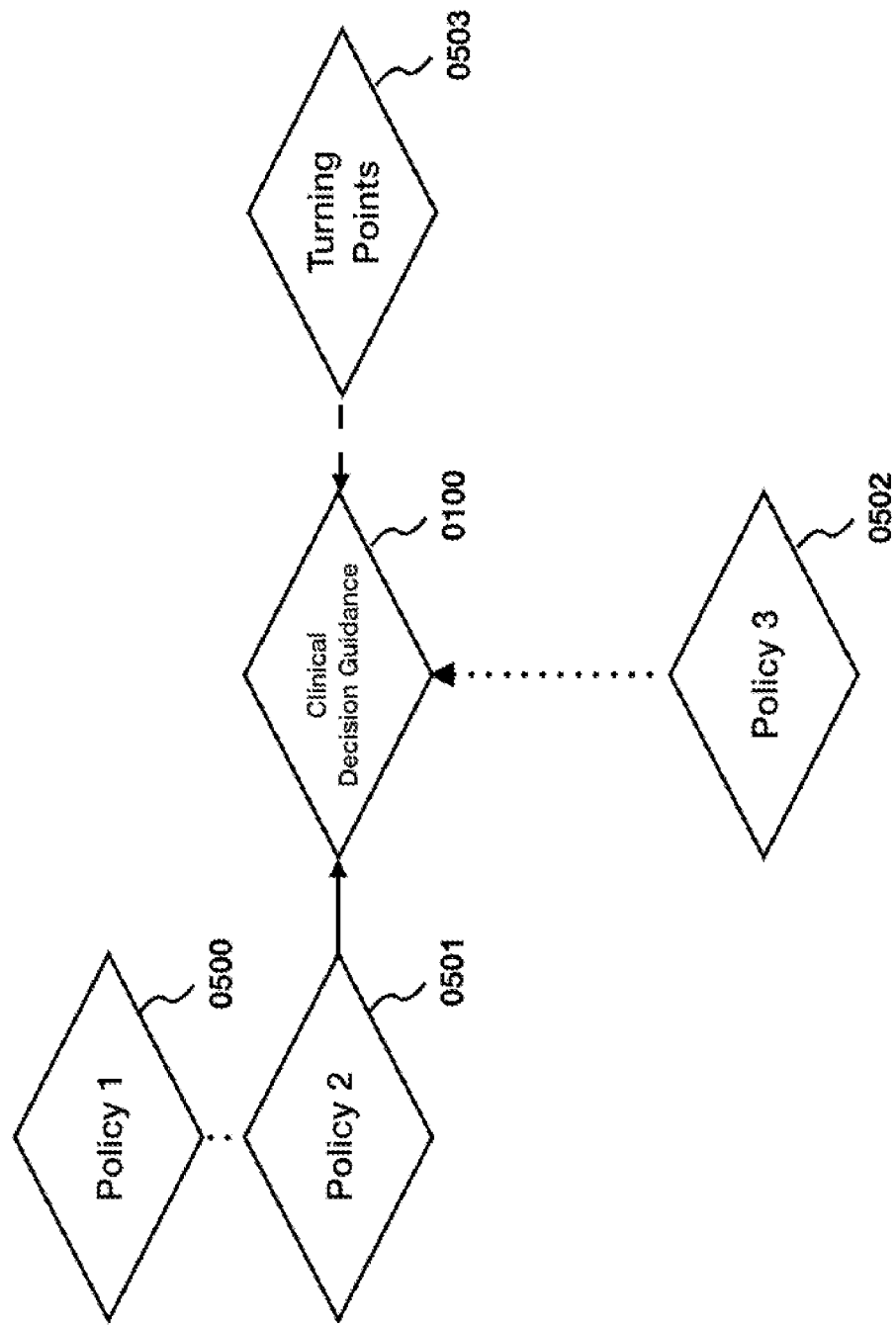
FIG. 6 is a flow-chart illustrating an example of Clinical guidance demonstrating policies from FIG. 1 in the context of medial guidelines.

FIG. 6 demonstrates an example where the clinical guidance system 0100 uses two policies to access and utilize guidance of the learning identifier, policy 1 0500 and policy 2 0500, that each look for the similarity of the experiential case-files to the index patient, where this is rule-based. Another policy 3 0502 which results from finding similar experiential case files is then reviewed along with policy 1 0500 and policy 2 0501 to ascertain how the similarity of the experiential case-files to the index patient changes. For example, the turning points 0503 are analyzed by each policy, for example, when a policy is a medical criteria that is tested how well the number of tests and exams are reduced by finding the turning points from lesser tests and exams.

The turning points 0503 is an example of the foregoing Clinical guidance, such as corresponding to a transition from an exploration pathway to an exploitation pathway. As an example, the transition (e.g., turning point 0503) of the exploitative pathway for diagnosis or treatment can test and learn to navigate the testing hypothesis to understand casual inference. For example, to find the casual inference requires a case study by keeping static similar variables and modifying a single variable of medical information and testing how that behaves based on medical literature that is explainable. By holding the variables constant and relating the similarity to similar experiential case files, and by adjusting the variables of the index patient and testing different new data assimilation compared to medical information explanation to build the case study. The described case study is referenced to medical literature for the similar experiential case files to relate the similar experiential case file physician notes. A particular method is using the dynamic equilibrium state space of the patient decision hypothesis, and further by applying game theory techniques to shift the reasoning of the index patient compared to similar experiential case files from the physician note decision hypothesis of the experiential case files by testing each of the turning points next state space tests from the similar experiential case file decision hypothesis. The turning points lead to predictive next steps. The aim is to understand the turning point by the clinical decision guidance 0100 adjusting the look ahead of the case to see how such turning point shifts in various pathways, and by determining least loss between similarity of experiential case-files for the index patient. This is a version of cross-entropy as part of information theory. For example, the similarity correlation using healthcare practitioner decisions for each learning identifier of the experiential case files to the index case, or what are called weights may be computed based on the relevance of each data assimilation and how they relate to the current testing hypothesis. In this context, the weights are the equivalent of weights (term constants) in neural network, but rather they seek to explain using the similarity of experiential case files by each new data assimilation that illustrates the correlative and non-correlative data and an amount of such correlation or non-correlation. The data assimilation create a plausible understanding of the signal similarity of experiential case-files and signal pathways with respect to the index patient. This provides an interpretable language conversion from human readable information that is transformed to a computation isomorphism that is manipulated in a manner that is analogous to a SOG (sea of gates) and subsequently converted back to medical knowledge. The reward in the reinforcement learning framework is the data assimilation outcome to hypothesis testing likelihood.

Figure 7:
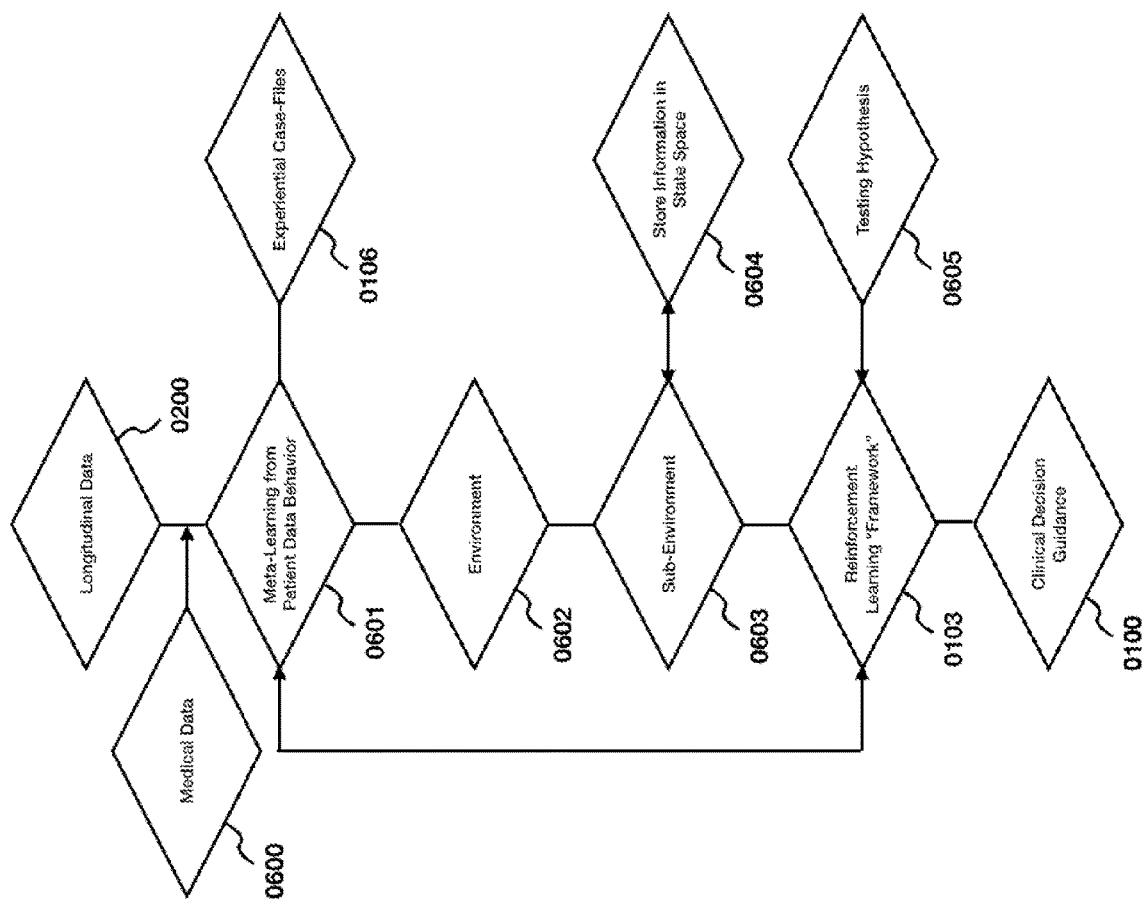
FIG. 7 is a flow-chart illustrating an example of Clinical guidance that demonstrate meta-learning of medical data including longitudinal data to extract and transform information into the clinical guidance.

FIG. 7 is a workflow diagram that illustrates an example of meta learning of medical data and longitudinal medical data to learn from a known medical concept of the patient to include the meta learning or predetermined medical concept written as part of the state space (e.g., environment) of the index patient 0602. The medical concept is a medical scientific behavior known about the patient. This could be the patient would have a pre-existing medical behavior based on a pre-existing medical condition. For example, the medical data 0600 is compiled with the longitudinal data 0200 using meta learning from patient behavior 0601 to the type of experiential case-file sub-space for review. The meta learning 0601 is programmed to use the environment 0602 and sub-environments 0603, collecting that information as a criteria from the state-space database 0604 and creating a reinforcement learning framework 0103 state space and how it evolves based on similar experiential case-files with emergent hypothesis testing 0605 that will adjust the meta learning to determine the next reinforcement learning framework which is fed into the Clinical guidance 0100 as illustrated in FIG. 2.

By way of example, it is common in a game to learn the sub-game. The environment and behavior of the game have to be learned. The meta learning 0601 is analogous to this behavior. The meta learning is programmed to perform a method of learning from one or multiple concepts that have been previously learned in other contexts. In the context of the clinical guidance system 0100, the meta learning 0601 is programmed to classify the type of patient behavior from knowing the similarity of experiential case files. The similarity may include a classifier, information from longitudinal data, medical data collected by patient. In a further example, the similarity may include patient condition key-terms, population health data, general exam, or a combination thereof. The meta-learning is updatable for readmission likelihood based on similarity to the index patient in outcomes across similar index patients, and hospitals and clinics.

As a further example, the environment 0602 is learned (by meta learning 0601) from the database containing the experiential case-files. The sub-environment includes aspects of how to organize the data. For example, for cardiovascular, minimalist information is organized by sub-environment of patient history, patient examination, and EKG. The sub-environment relate to a new data assimilation that leads to what can be CT, PET, or MRI imaging, possibly leading to surgery, and blood work. The hypothesis testing is useful to discern what the medical practitioner perceives is the condition classification. The hypothesis testing is useful if the experiential case-files are similar to the hypothesis testing for several sub-spaces. This is a way of looking at different sub-games when exploring case-files. This can be repeated (e.g., by clinical guidance system 0100) in subsequent steps as new data assimilation is added. The clinical guidance system 0100 would see if there is a similarity between sub space and the environment of similar conditions. One or more additional sub-space can be added at any state transition of a given pathway at any time.

Figure 8:
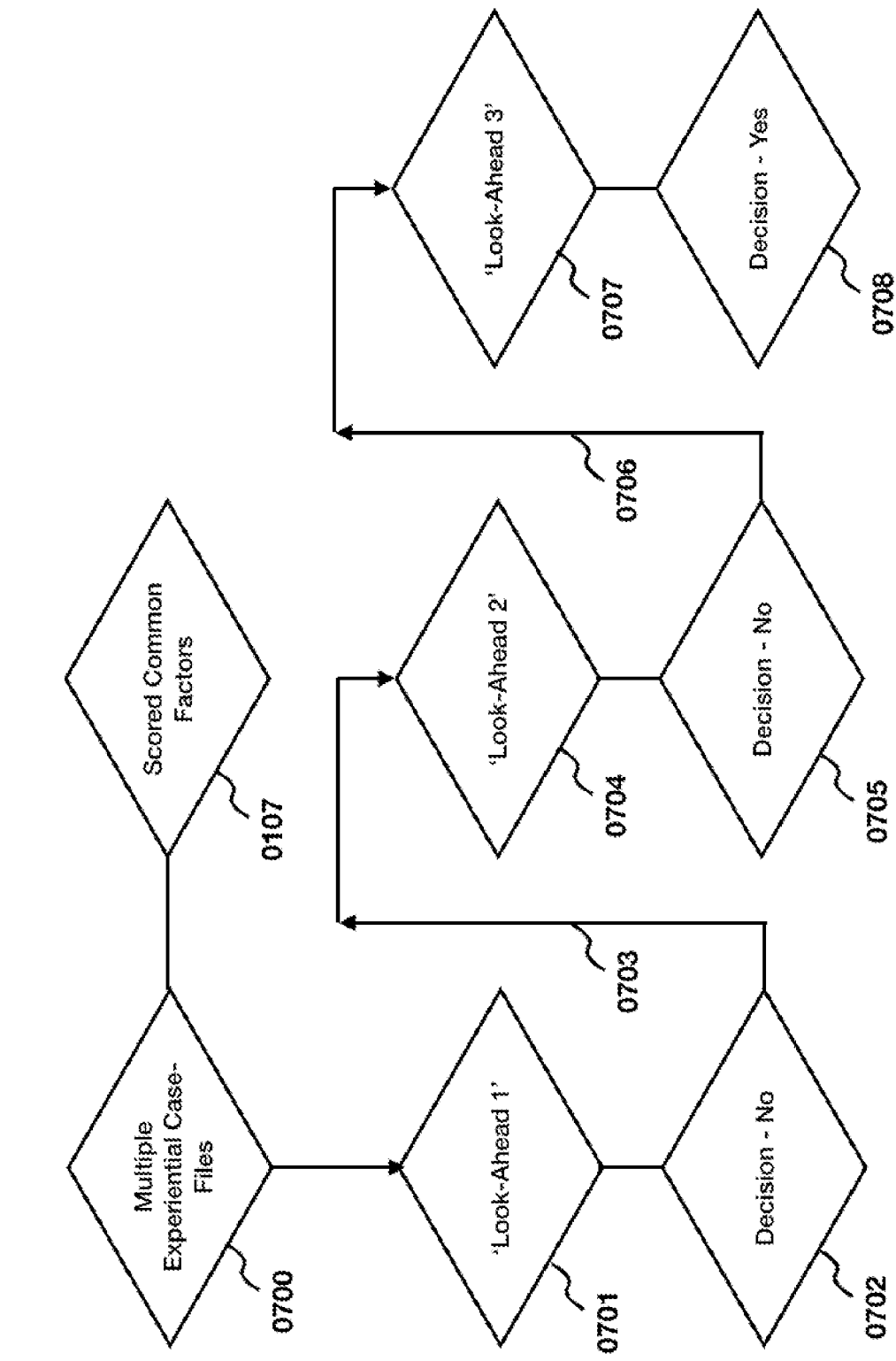
FIG. 8 is a flow-chart illustrating an example of Clinical guidance that demonstrates learning of correlative and non-correlative sub-environment information.

FIG. 8 is a workflow diagram illustrating an example of learning when the similarity of case-files require look ahead when a sub-environment is non-correlative. The similarity is examined by scoring the common factors 0107 of similar experiential case-files, and observing same multiple experiential case-files 0700 of the same diagnosis or treatment as look-ahead 1 0701. The look-ahead 1 0701 determines if the healthcare practitioner decision was made by either for diagnosis or treatment from the sub-environment or sub-sub-environment, and look how related the experiential case-files 0703 to correlate a decision from next sub-environment or sub-sub-environment. If there is no decision, the next step is observed as another look-ahead 2 0704 pathway that is repeated by simulating if a decision 0705 was made, and if not, then the system looks at how correlative or non-correlative 0706 is to making a decision by looking at turning points (e.g., turning points 0503) and which variables in the environment, sub-environment, and sub-sub environment is correlative or non-correlative to each similar experiential case file, and this information is counted based on frequency and standard deviation averaging. The identified variables that are correlative or non-correlative from the found similar experiential case files are then compared to the index patient with each new look-ahead 3 0707 with this time the decision is yes from the sub-environment or sub-sub-environment. The clinical guidance recognizes this decision by repeating this process and by understanding the correlative and non-correlative behavior of the sub-environment or sub-sub-environment. This was learned from monitoring and treatment the relevance of how to weigh a particular diagnosis, treatment, prevention, and through the use of non-rule based methods.

The decisions 0702, 0705, 0708 are recorded using the testing hypothesis and outcome recorded by the Clinical Guidance System 0100 that compares similarity of experiential case-files. As a use case example, when adding new data assimilation, look ahead is performed to understand if the next information can lead to similarity of experiential case-files. The look ahead performed on the data assimilation may find a particular similarity of experiential case-files based on the present data assimilation, but the medical practitioner needs to learn ahead if the similarity can change based on tests, exams, monitoring, etc. The ability to look ahead is a primary reason to investigate patient outcomes.

The clinical decision system is programmed to look ahead by steps to inform the medical practitioner what turning points are useful to understand the patient condition. This way, the system is able to understand one step, next step, and how they are scored in decisions. This may lead to a gamification approach similar to chess.

Figure 9:
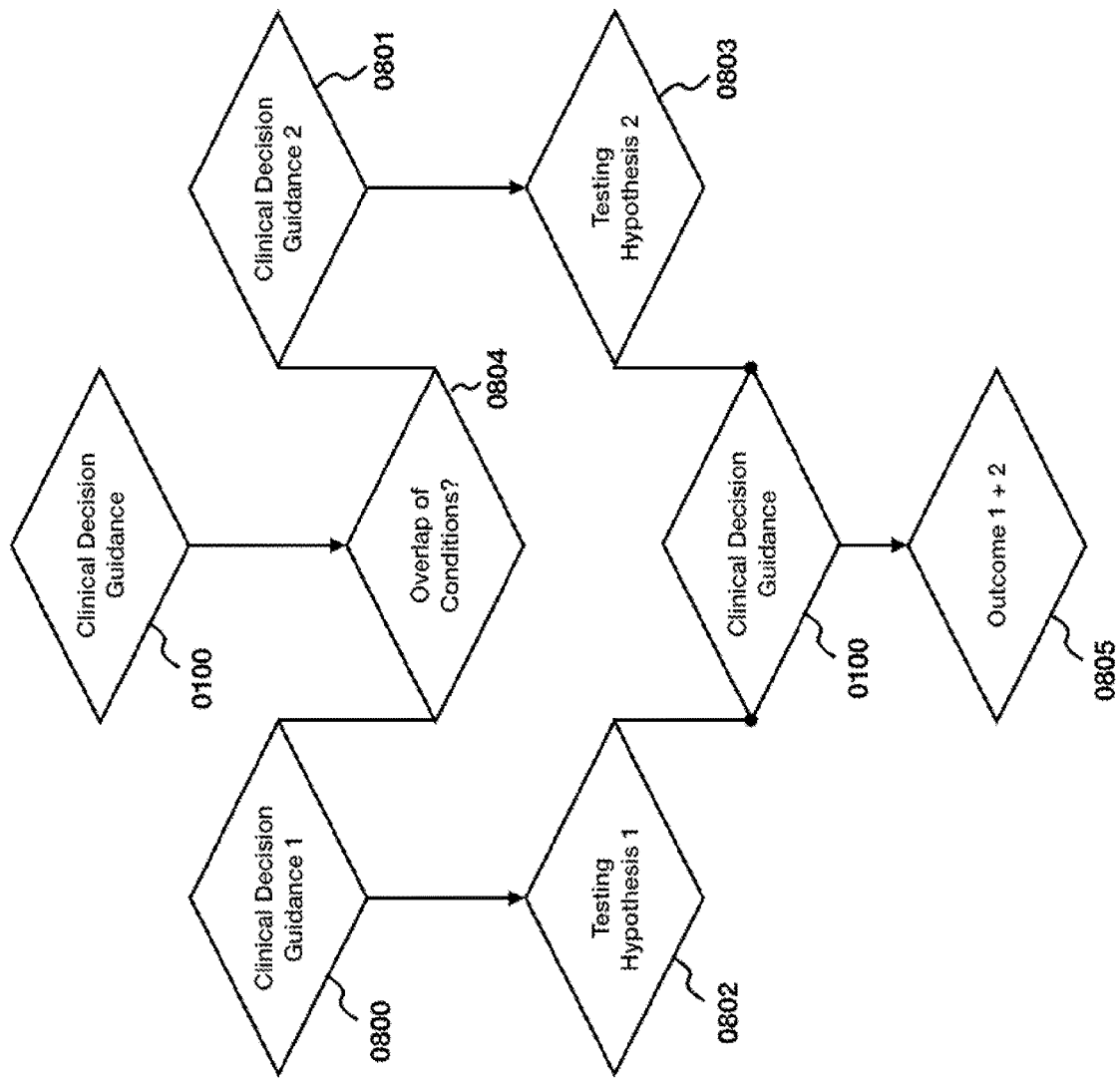
FIG. 9 is a flow-chart illustrating an example of Clinical guidance demonstrating the identification of an index patient's multiple conditions as related to experiential case-file data with multiple conditions.

FIG. 9 is a workflow diagram that illustrates an example of a method for exploration and determination of similarity between experiential case-files with multiple conditions and the index case file. The Clinical guidance system 0100 (from FIG. 2) observes patient overlapping state space 0804 for the experiential case files, such as determined from vital signs or medical procedure from the environment and sub-environment when evaluating similar experiential case-files. As mentioned, the environment corresponds to the state-space for a given set of index data and experiential case data. The state-space contains a plurality of sub-environments (also referred to as sub-spaces) of information that describe characteristics. Each environment may consist of a plurality of sub-environments, each of which may include one or more sub-sub-environments and so on to define a set of hierarchical structured data.

In the example of FIG. 9, the state space is incorporated into clinical decision guidance 1 0800 and clinical decisional guidance 2 0801. The clinical decision guidance blocks 0801 and 0802 are programmed to evaluate each medical diagnosis condition, such as, for example, looking for a stroke and aneurysm separately with a testing hypothesis 1 0802 for the first condition, and aneurysm 2 0803 for the second condition. Based on such evaluation, the outcomes are then combined by Clinical Decision Guidance 100 to relate back to the similarity of experiential case-files of the multiple conditions demonstrated as the Outcomes of 1+2 0805.

The overlap of conditions 0804 in the example is two, but can include any number of conditions. Different policies can be used for each parsed Clinical guidance 0800 and 0801. The environment and sub-environment is broken up and recombined as the index patient to find similarity of experiential case-files. The Clinical guidance can combine environments and sub-environments to then review overlapping experiential case-files. New data assimilation that is useful for determining overlapping conditions; the similarity of experiential case files could be specific for each condition, or a combination of both conditions. The clinical guidance system 0100 can find a learning identifier for each condition separately or find similar experiential case files that contain both conditions. The state space can be split for each conditions or combined for the overlapping conditions for combining both conditions as then a single condition of two conditions.

As a further example, the testing hypothesis 0802, 0803 is directed to several potential outcomes. It may be that the potential outcomes inter-relate, and this inter-relationship can be identified by the clinical decision guidance 0100 when parsed based on the similarity of experiential case-files. The system 0100 can propose several conditions and outcomes of these two or more conditions by identifying from the scored common factors and next experiential case-file how the several conditions would increase similarity of the experiential case files. The policy can dictate how the relationship of tests, exams, monitoring, and the like as a medical criteria for each condition, and another medical criteria for how conditions relate. The Clinical guidance 0100 can further be programmed to specify (e.g., via a user interface) how a particular condition can be monitored to adjust the testing hypothesis from longitudinal data. This would be an equivalent patient alert sent to the medical practitioner.

Figure 10:
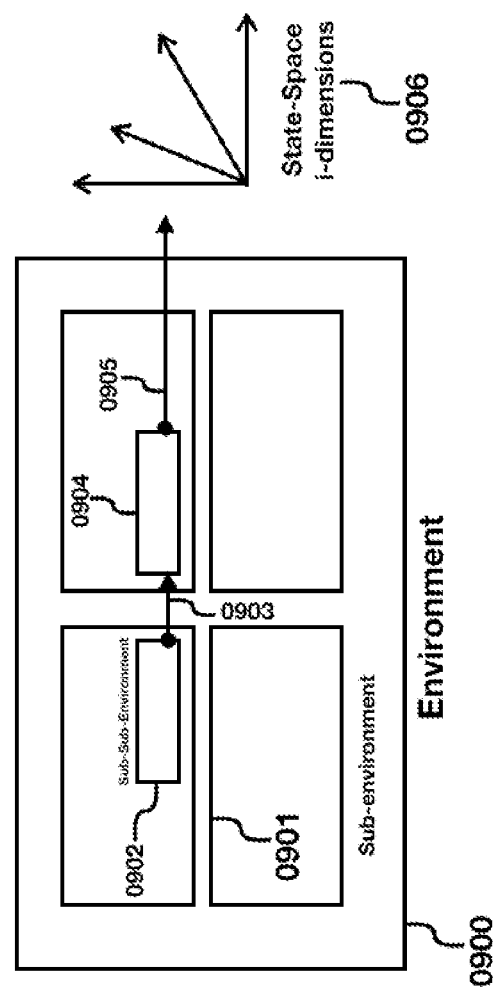
FIG. 10 depicts an example of a topological representation for an environment.

FIG. 10 depicts an example of a topological representation for an environment 0900 of i-dimensions for the reinforcement learning framework (e.g., framework 12 or 103). The environment 0900 includes a sub-environment 0901 of m-dimensions, which includes a sub-sub-environment of n-dimensions 0902. In this example, the sub-sub-environment of n-dimensions 0902 maps 0903 a new sub-space of sub-sub-environment 0904 of l-dimensions. The mapping 0903 is the state space from the index patient to the similar experiential case files. The sub-sub-environment 0904 maps 0905 a new state space 0906 that is a collection of state-space of i-dimensions 0906. The mapping 0905 is a complete state space for the index patient and same experiential case files. The sub-environment 0902 of m-dimensions has at least sub-sub environment of n-dimensions, and is a multiple of each sub-sub environment dimensions. In an example, state space that is created from the experiential case file as a new database containing the state space of l-dimensions. Each environment is the state space, and each sub-environment are sub-states, and sub-sub-environment are sub-sub-sub states.

As a further example, each dimension of the environment 0900 may be of a different dimensional size within the database. The state space dimensions can be rotated or shifted based on a topological state space in the database. The order of the database is not predetermined. The dimensions of the environment 0900 may grow by adding dimensions with each new additional sub-environment. The topology mapping 0903 to a new sub-space occurs with new data assimilation, or healthcare practitioner decision, testing hypothesis, and outcome. For example, each dimension contains information including time-stamp, unit results, patient information, tests, exams, etc. In an example, the relationship between an environment 0900 and another environment, sub-environment, and sub-sub environment based on time is a difference between the time of the environment 0900 and another environment. The time difference from one state and another is determined (e.g., by clinical guidance system) based on a time stamp at multiple time instances in the state space. For example, dates and ranges between heart pain is found from the learning identifier for finding time related index patient case-file to then find similar experiential case files.

As an example embodiment, the topology of the environment 0900 is such that the sub environment 0902 and sub-sub environment 0902, 0904 shift to reflect the experiential case-files. This is a translation and rotation of the sub-space. This can be the sub-environment, sub-sub-environment, and the like. As another example embodiment, the rotation and translation is read by the database as a hash, or position by identifying position using positions as a gate, wherein the gate is an operation on sub environment or sub-sub environment information from the similar experiential case file and index position. In an example, gate can be an AND, OR, NAND, and the like, to compare variables within the state space. In another example, the gates can represent a tree database structure known by those in the art. The database is written and read by relational or preferably a non-relational to create each index patient copies indexed to each experiential case-file or the experiential case-file indexed to the index patient. The database is kept on a single or multiple services, such as by using a distributed ledger to direct where the information is located to build a particular database specific for the index patient. As another example embodiment, the data is read using a distributed ledger type blockchain, which is linked to cryptography.

An example of encryption that may be implemented is described by the experiential case-files in FIG. 3. For public/private key, the database can be encrypted. As yet another example embodiment, the database is growing to organize case-files based on the classification from its own index patent to similar experiential case-files. The experiential case-files can be copied and shifted by rotation and translation and be tagged using the distributed ledger with each new data assimilation. Collections of new data assimilation for the index patient can be directed for new tests, exams, or patient information from the similar experiential case-files by the clinical guidance system. The system may autonomously interact information from the similarity of experiential case-files to send an alert to the medical practitioner. The provision of an alert may be dependent on policy, or testing hypothesis.

Figure 11:
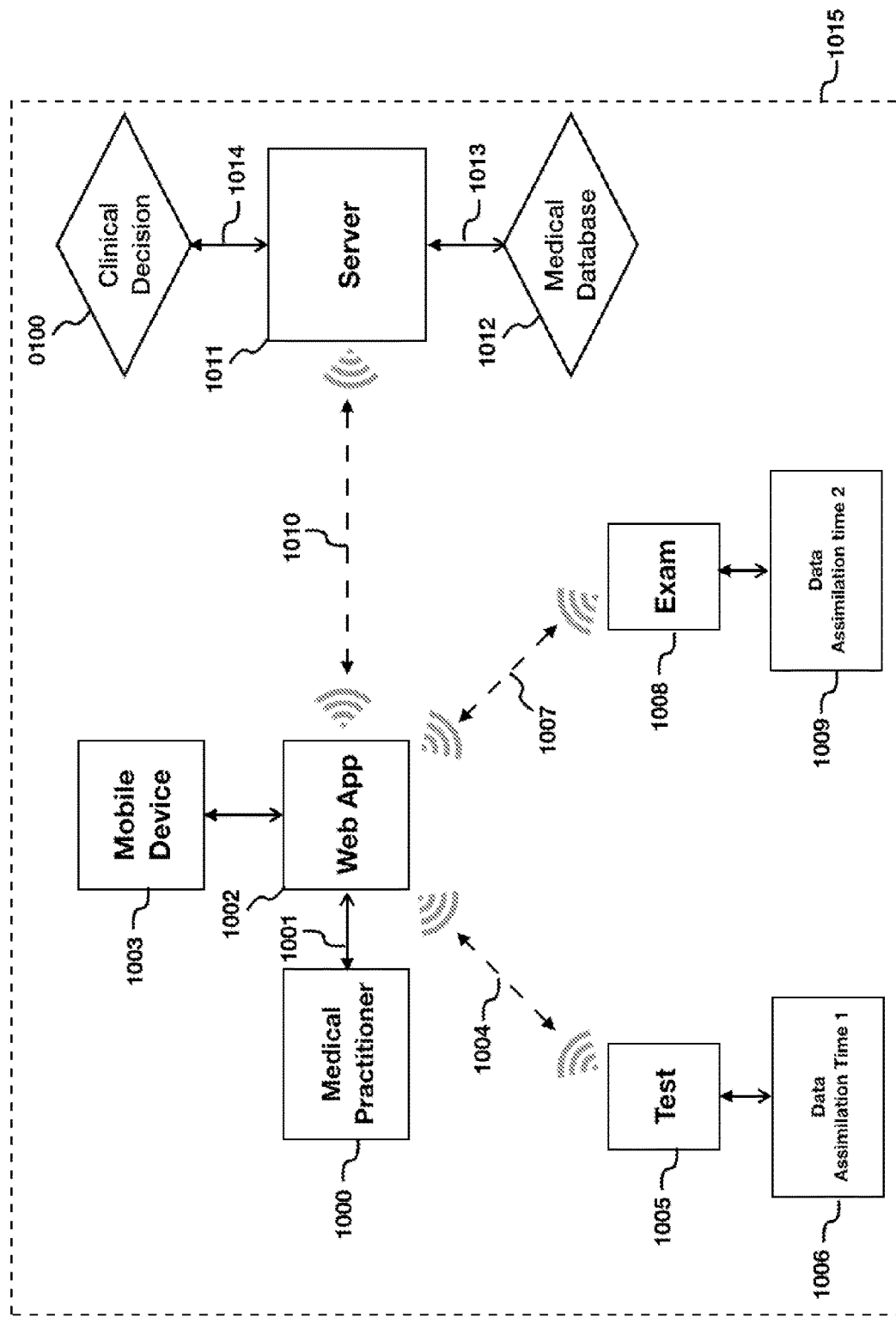
FIG. 11 another example of a clinical decision system.

FIG. 11 illustrates another example of a clinical decision guidance system 1015 (e.g., corresponding to system 10 or 0100). In this example, the clinical decision guidance system 1015 includes a dashboard (e.g., a graphical or other form of user interface) 1001 with which the medical practitioner 1000 may interact (e.g., read or write with respect to). The dashboard 1001 may be implemented by a web-app 1002 that is executing on mobile device 1003, for example. In the example of FIG. 11, the web app 1002 is shown communicating wirelessly 1004 with a test 1005, which communication may include the medical practitioner to speak by voice recognition, diagnostic test or monitoring, imaging information as a specific type of data assimilation at time 1 1006. The web app 1002 thus can read the data assimilation time 1 1006 and provide it to the mobile device 1003 for use processing by clinical decision guidance 0100, as disclosed herein. The web app 1002 may also be programmed to employ a second wireless communication 1007 to receive an examination 1008, which is another specific type of data assimilation at time 2 1009. The two times for data assimilation at time 1 1006 and at time 2 1009 are for purposes of having a time stamp to help place in the longitudinal record. The examination 1008 thus is sent to the web app 1002. The web app 1002 is further programmed to communicate wirelessly, demonstrated at 1010 with a server 1011. The server 1011 contains the experiential case-files 1013 that are read from the medical database 1012 and written to the server 1011 for further processing by the clinical decision system 0100.

The clinical guidance system 0100 may include one or more such servers 1011, which may be distributed. The mobile device, for example, a smartphone, augmented reality device, laptop or desktop computer, transparent screens, holograms, and the like. The clinical decision on the server may or not have a user interface to run commands sent by the web app in response to user input instructions from the medical practitioner as an API as a set of digital instructions or health information from the clinical guidance systems 0100.

As an example, the web app 1002 is programmed to send an evidence gathering request by API to the test or examination. The medical database 1012 relates to FIG. 10, being one or multiple, such as using a distributed ledger and servers. The wireless communication, demonstrated at 1004, 1007 and 1010, may include WIFI, broadband, cellular and related IP wireless protocols served by the web. With encrypted permission, the information in the server 1011 may be sent to each mobile device in real-time. The data assimilation may include data representing a diagnostic test and examination related to each other and which overlap their time stamp as concurrent time. A random number generator assigned to both can assign the order with which they enter the server. The data assimilation can be a discrete number of steps that is stored contiguously for the patient record. This information is added per each case, time, outcome, etc., and we will build the longitudinal patient record with age, type of condition progression, treatment, etc. for the index patient.

Figure 12:
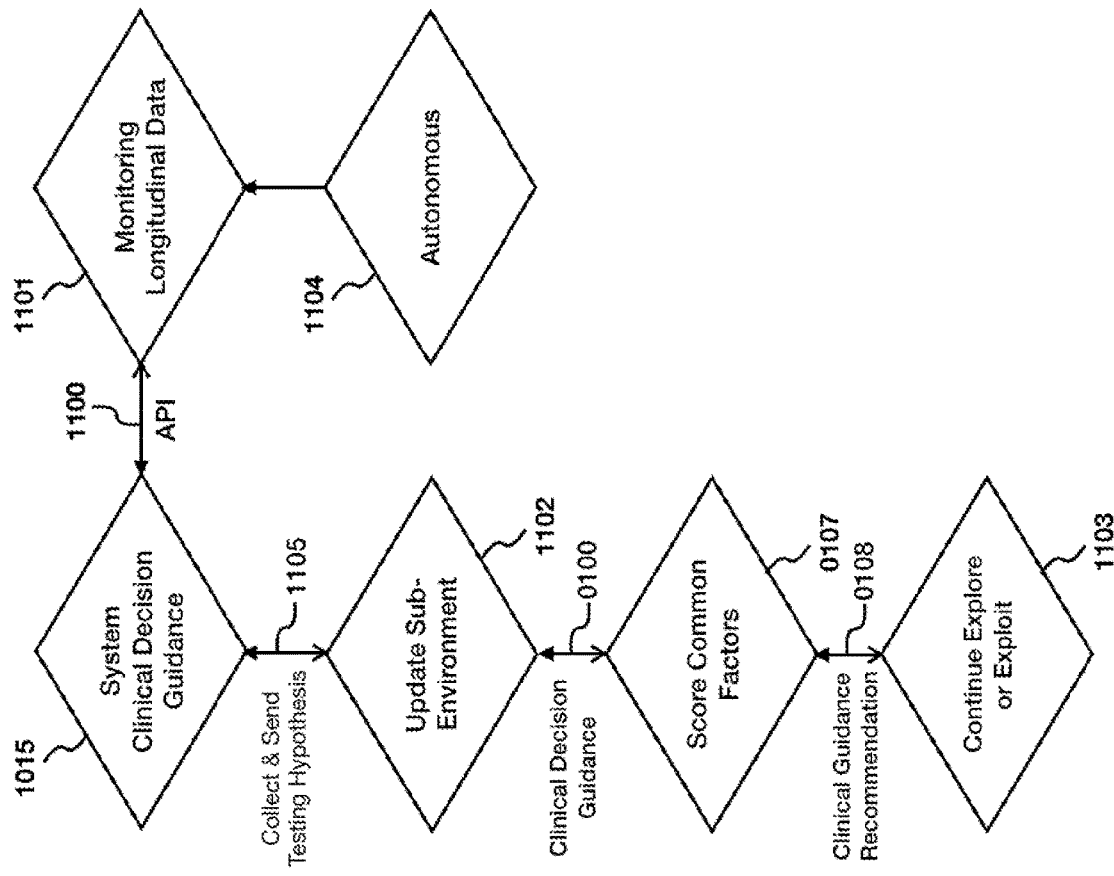
FIG. 12 is a workflow diagram is a workflow diagram illustrating an example method for autonomous monitoring.

FIG. 12 is a workflow diagram illustrating an example method for autonomous monitoring 1104 that may be implemented by the clinical decision guidance system 0100. For example, longitudinal data 1101, which is acquired by a health sensor or medical practitioner providing environment data, is sent to the clinical decision guidance system 1015 by API 1100. The clinical decision guidance system 1015 (e.g., corresponding to clinical guidance 0100) is programmed to collect and send back and forth, demonstrated at 1105, the testing hypothesis by the medical practitioner guidance or another medical practitioner. The testing hypothesis 1105 in turn updates the sub-environment 1102 and looks at the pathway testing hypotheses from the Clinical Decision Guidance 0100 by scoring the common factors 0107. For example, the testing hypothesis is generated by collecting medical information from a digital health app and relating this to the index patient EHR to understand the patient condition, and find what is the right decision hypothesis from the available ways that data is able to be collected. A clinical guidance recommendation 0108 is made (e.g., to the practitioner via a user interface) to choose to continue to explore with the longitudinal data or exploit 1103. In response, the medical practitioner can decide intermittently to review the data and create new healthcare or medical decisions using the clinical decision guidance system 1015 such as to define a testing hypothesis (e.g., corresponding to clinical guidance system 0100).

As a further example, the autonomous monitoring method 1104 is programmed to collect data and decipher the data autonomously without a medical practitioner present. This allows patients to be treated in circumstances by family members or other non-professionals. Autonomous data collection facilitates diagnostic testing, collection of data from disparate sources like a pharmacy, medical imaging center, and the like. For example, multiple medical practitioners can request this data, relate analysis of the testing hypothesis, and see how well the testing hypothesis is predictive or the treatment needs to change. The medical practitioner can access tests, examinations originating from autonomous data that can be obtained manually by a person or electronically (e.g., from a device or sensor). The autonomy is not limited to monitoring longitudinal data, but also may be applied to diagnosis or any other outcome that the system performs. The medical practitioner can intervene in or request to review the patient case-file to continue to explore or exploit 1103 from the clinical decision guidance system 1015 (e.g., corresponding to clinical guidance 0100) patient index case-file, and ascertain when possibly an exploitive pathway has an increased likelihood of a better outcome, or what would indicate a differential in the testing hypothesis. The medical practitioner may seek several testing hypothesis. The medical practitioner may seek to change the testing hypothesis at 1105 which directs which test, examinations, diagnostic, etc. are indicated and by whom. The system clinical decision guidance can test multiple testing hypotheses based on the longitudinal data 1101. As an example, this information can relate to readmission likelihood with new data assimilation.

The Continue Explore or Exploit 1103 generated by the clinical guidance recommendation 0108 is how much information is known from the monitoring of longitudinal data 1101 with the goal of elucidating the testing hypothesis score. The turning points (e.g., turning points 0503) from the option to continue explore or exploit 1103 is to identify the exploitative pathways. This can be sent via alert to the appropriate medical practitioners. It is feasible that longitudinal data 1101 can be augmented or replaced by further tests, examinations, and the like. The medical practitioner can explore until they can find one or several exploitative pathways to then test, examine, or, for example, gain approval for imaging such as a CT or MRI to learn from.

Figure 13:
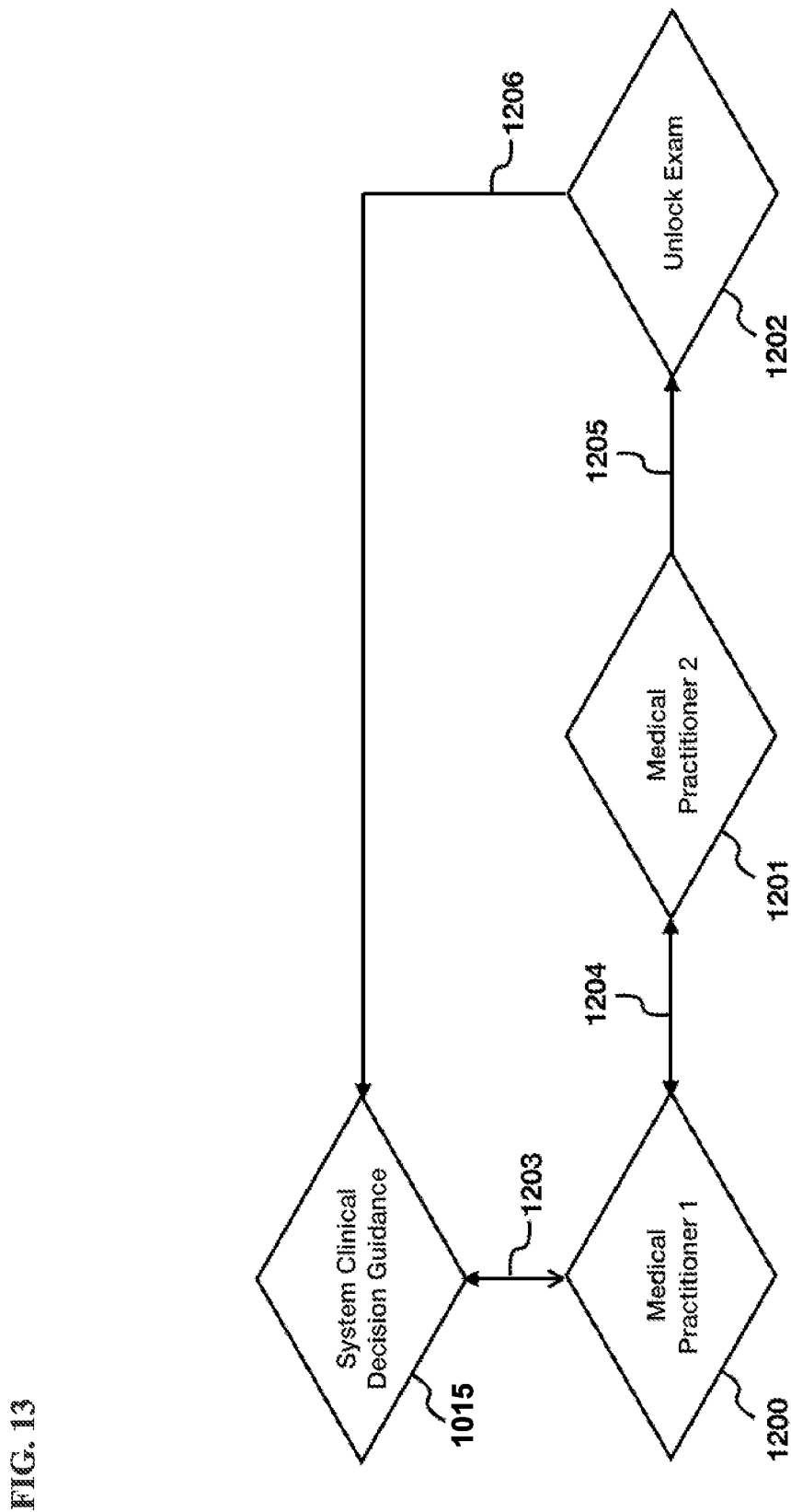
FIG. 13 workflow diagram that illustrates an example method of interactions between medical practitioners.

FIG. 13 is a workflow diagram that illustrates an example method of a medical practitioner 1 1200 receiving a request to review 1204 from another medical practitioner 2 1201 that makes a decision to unlock an exam (or any procedure or intervention) 1202. For example, the examination could be from a specialist sharing the clinical decision guidance system 1015 (e.g., corresponding to clinical guidance 0100) with the other medical practitioner 1 1200 that could be a primary care physician using telehealth. For example, the medical practitioner 1201 that unlocks examination 1202 for medical practitioner 1 1200 is giving permission for examination and this updates the System clinical decision guidance 1206 where the medical practitioner 1 then performs the examination 1203.

As an example FIG. 13 demonstrates a scenario in which an attending medical practitioner 1200 is reviewing the clinical decision guidance system 1015 to determine what test to perform. The unlocking of the examination is a policy the hospital or medical practitioner is permitted. The attending medical practitioner 1200 can review what other medical practitioners may perform and can also collaborate with decisions. The medical practitioner can further learn by looking at similar experiential case files identified by the system. For example, aspects of similarity between experiential case files found from the learning identifier can be compared by having the medical practitioner look at other similar experiential case files and the degree to which they are similar or not throughout the environment including sub-environment, and sub-sub-environment, etc., per category if so chosen. The practitioner may also review one or more look ahead pathways for the index case to understand based on his/her data analysis (e.g., observing look ahead pathways analysis using temporal difference in reinforcement learning, multi-agent reinforcement learning directed by the medical practitioner to test as setting the strategy, observing similar experiential case file, decisions they would make and compare to what is found similar from the learning identifier, time-series analysis, and simulation of the case-file with different policies) makes the index case more or less similar to the experiential case files.

The clinical guidance system 0100 is yet to look for low probable conditions seen, called Zebras. The identification of these may require specialists to build Telehealth or other external consultants. These consultants can indirectly guide the system which would perform untried path exploration. The medical community can explore by unlocking cases analogous to unlocking exam 1202 that have yet to be exploited.

Figure 14:
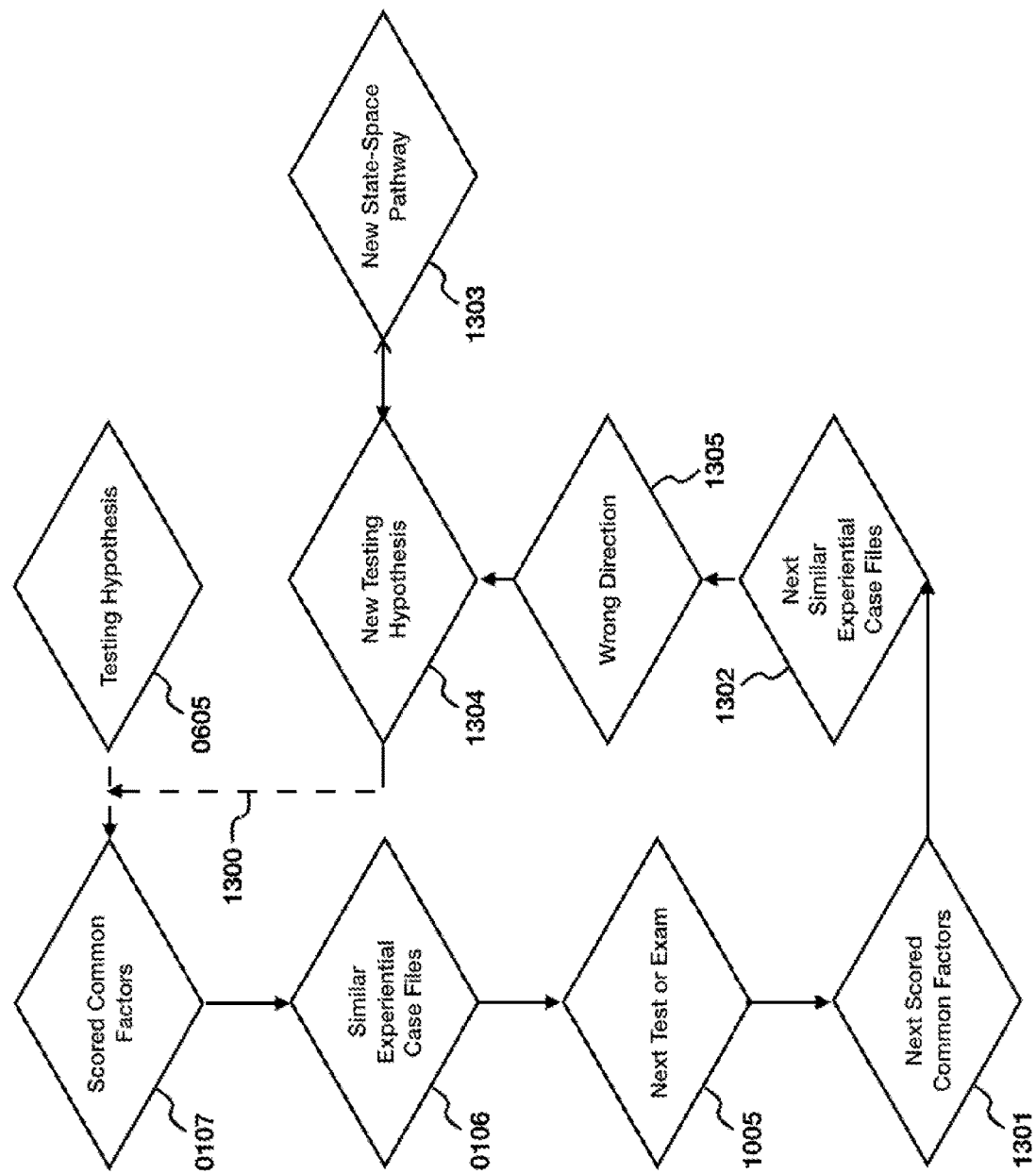
FIG. 14 is a workflow diagram illustrating an example of a method of clinical guidance that evaluates a testing hypothesis.

FIG. 14 is a workflow diagram illustrating an example of a method of clinical guidance that evaluates a testing hypothesis 0605. In this example, the clinical guidance computes scored common factors 0107 to evaluate the testing hypothesis 0605. For example, based on scored common factors 0107, the clinical guidance is programmed to find similar experiential case files 0106 and assume next test or examination results 1005 and explorative or exploitatively score common factors 1301 and from the next similar experiential case file 1302 determine a low predictive value 1305. A new testing hypothesis is derived 1304 by going back to an older state-space pathway 1303 that includes different next test and/or examination 1005 by exploring or testing the new hypothesis. The exploration would be for the healthcare practitioner to use a new look ahead to find different pathways and what differential diagnosis or treatment could lead to a new understanding of the index patient from the similar experiential case files. This may be a missing information from the electronic health record is pertinent, such as social and environmental determinant or observing longitudinal data.

The situation when the predictive value is not correct, such as by not finding similar experiential case files from a decision hypothesis after several new data assimilations from next test or examination hypothetical results, the clinical guidance determines it is going in a wrong direction. This requires a recalibration to find a new testing hypothesis either by exploring or then finding another pathway to exploit. The ability to have the Clinical guidance system to look for a higher similarity experiential case set with look-ahead and/or look-behind pathways enables the Clinical guidance to generate outputs for review why an unsuccessful hypothesis led to different undesired results. The clinical guidance system may further be programmed to find similar experiential case-files that corroborate what other medical practitioners concurred upon. As an example, the patient's condition would have been similar to the experiential case-files but required further differential diagnosis to see identify a bad pathway. This is analogous to trying a chess move and then rejecting it after looking several moves ahead. Such pathway analysis signifies a good policy or what can be considered an acceptable or even optimal outcome for diagnosis or treatment.

As another example embodiment, experiential cases with an aging factor that is to review from similar experiential case files from the learning identifier newest case-files as a bias, medical practitioners receive case-studies and performance for patients of different aspects based on their state-space response to a new pharmaceutical, treatment, and population health data. Because such treatment or medication was not previously practiced, and its results are superior (e.g., because it is newer), it is given preference to older cases where prior treatments or medications were utilized. The reinforcement learning identifier will find similar experiential case files, for example, similarity factor increase multiplier from the scored common factors for similar case files that decreases exponentially or linearly with experiential case files that are dated later.

Figure 15:
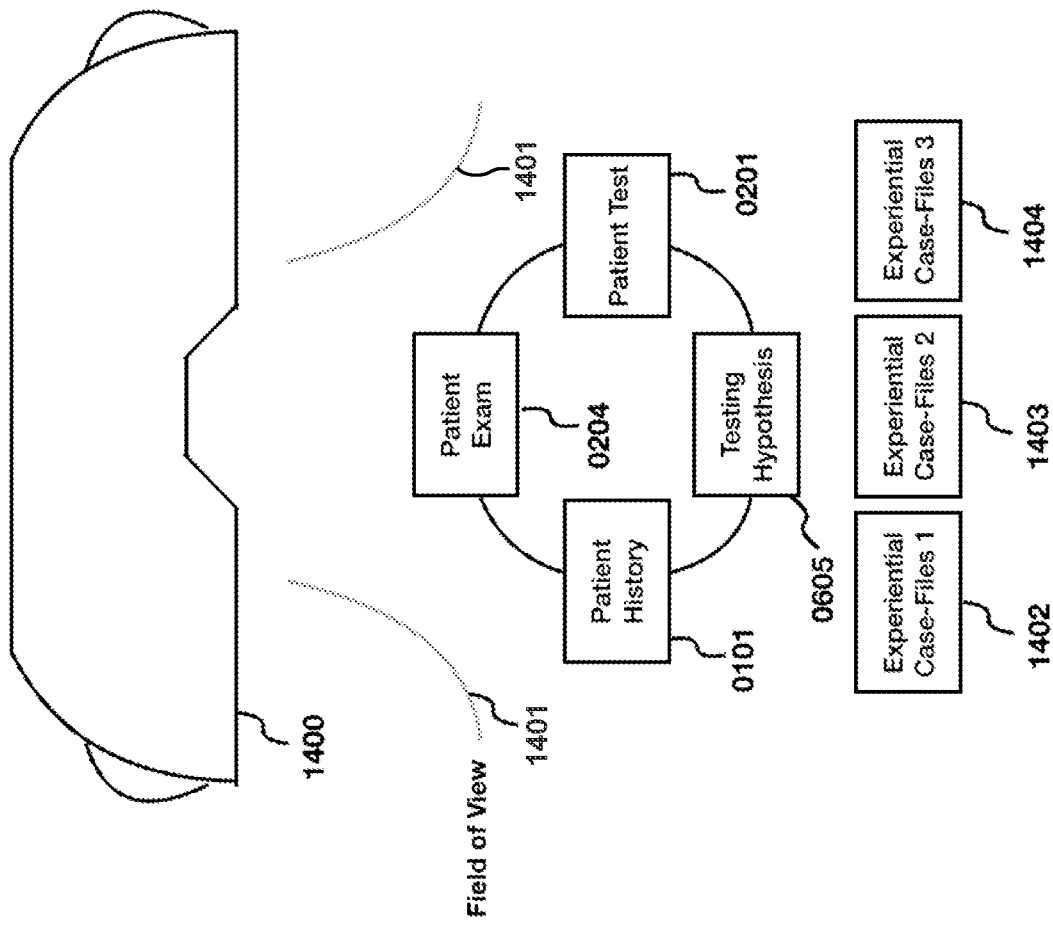
FIG. 15 depicts an example of Clinical guidance being visualized using an augmented reality device.

FIG. 15 depicts an example of Clinical guidance being visualized using an augmented reality device 1400, such as where information appears within the device's field of view 1401 worn by the medical practitioner, such as in the presence of their patient. In this example, patient history 0101, patient examination results 0201, patient test data 0204, and testing hypothesis 0605 appear in the field of view 1401 as new Information is entered into the system via one or more user interface, such as by means of voice recognition interface, hand signals (e.g., via gesture user interface), and the like. Experiential case-files-1 1402, experiential case files-2 1403, and experiential case-files-3 1404 may be visualized for the medical practitioner who can ask questions as what-if scenarios for look ahead pathway analysis in response to user input instructions (e.g., by voice or hand signals) and similarly request system functionality. The augmented reality device 1400 thus is used as a tool for the medical practitioner.

By way of example, medical practitioners can share the information with each other by looking at a web app or other application that is running and visualizing such information from the other medical practitioner's augmented reality field of view 1401. The images visualized in the field of view 1401 may be created using standard programming languages like Unity3D and Swift. As an example embodiment, the medical practitioner can visualize positions on the body where tests are to be performed. For anatomical purposes, the Clinical guidance is able to show visuals of locations of the heart, brain, etc. And, in a further example, health sensors (e.g., microphones) can record the heart sounds from the patient that the medical practitioner hears and send them to the system for storage as part of the patient exam 0201. This use the microphone as part of the augmented reality device 1400 or external sensor with heart sound sent by API from the augmented reality device to the medical practitioner or other user such as a teacher. Such information may include noise, health sensors including augmented reality embedded health sensor, external health sensor measuring blood flow, pressure, facial expression, eye tracking, oxygen, pulse, EKG, Galvanic Skin Response, Accelerometer (patient position), temperature, Electromyography, and the like.

Figure 16:
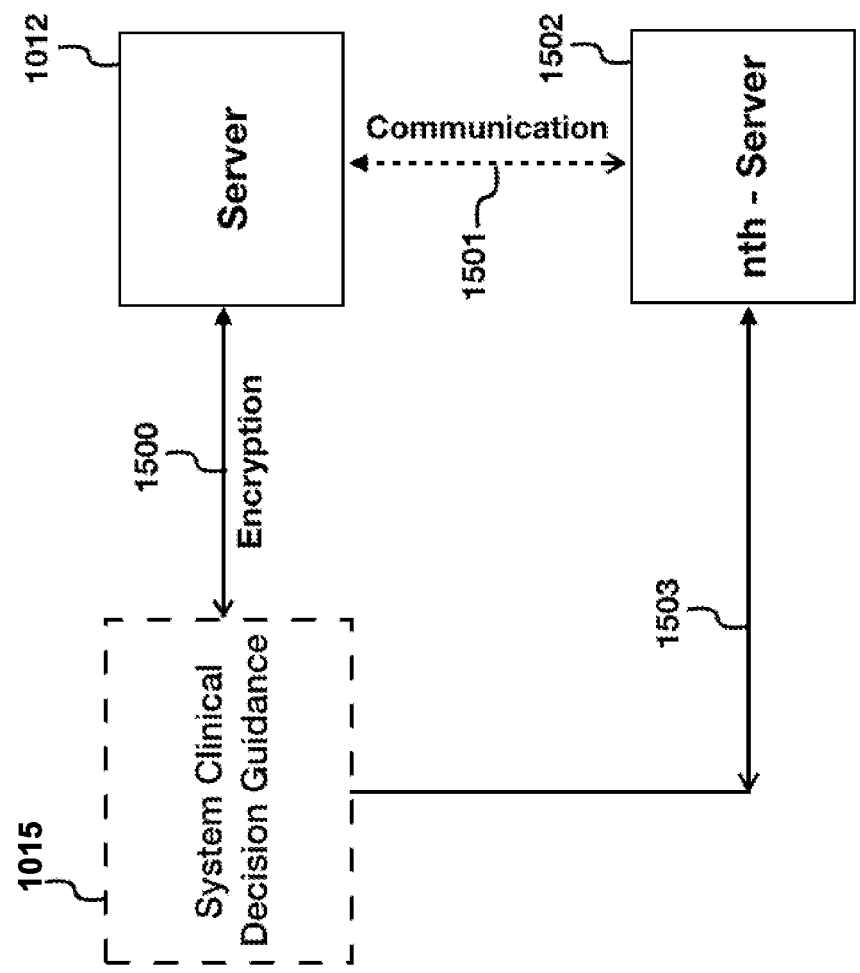
FIG. 16 illustrates an example system that includes multiple servers interacting with a clinical guidance system.

FIG. 16 is a block diagram demonstrating the Clinical decision guidance System 1015 implementing encryption 1500 in communication of data to and from a server 1012. For example, data is encrypted before sending patient and medical practitioner data assimilation and clinical guidance data to and from a server 1012 that may communicate with multiple other servers 1502. Such one or more other servers 1502 may be configured to either communicate with the clinical decision guidance system 1015 via secure link 1503 or to a central server 1012 that is communicating with the System Clinical guidance.

In an example, servers 1012 and 1502 can communicate with each other over a communication link 1501. There can be a central server 1012 for training and validation for review of prior learnt case-studies. These can be used for storing the longitudinal patient data, which may be called for by a medical educator for the purpose of diagnosis, treatment, and prevention, such as disclosed herein.

Figure 17:
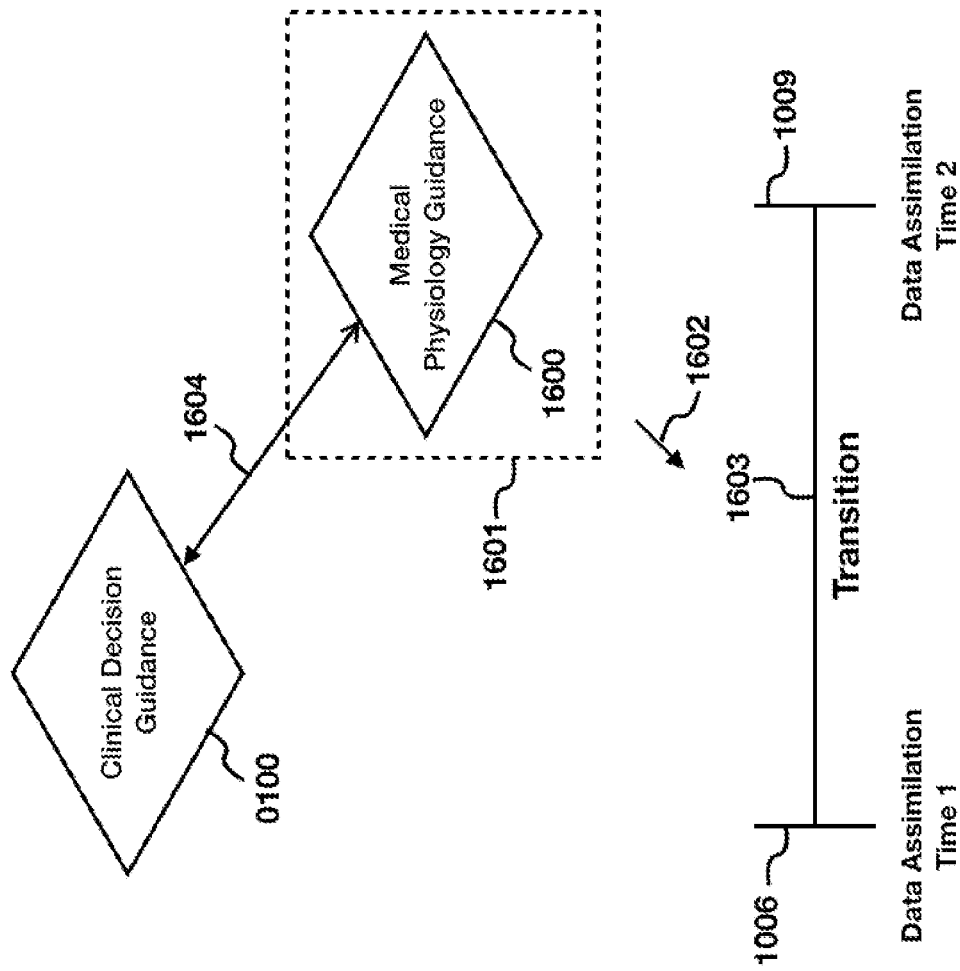
FIG. 17 depicts an example method for a learning chain from the Guidance System.

FIG. 17 depicts an example method for a learning chain from the Guidance System. For example, Clinical decision guidance 0100 collects information from data assimilation time 1 1006 and from data assimilation time 2 1009. The learning identifier finds similar experiential case-files that are consistent with a decision 1604 by the medical practitioner across those similar experiential case-files. For example, the clinical decision guidance 0100 is discovering biologically relevant properties of humans, like heart behavior. In this example, the system 1601 utilizes a transition 1603 between data assimilation times 1006 and 1009, which are reported by the medical physiology guidance 1600, to relate what is happening to the transition by explaining physiology 1602 by finding similar experiential case-files that indicate the particular physiology. For example, the transition is physiological behavior of the patient's heart that would indicate one condition or another if the patient then had a different physiological data result. The medical physiology guidance 1600 includes a medical glossary and is programmed to train on experiential case-file data from known medical knowledge. As an example, the medical physiology guidance 1600 may learn the properties of an ST-Elevated Myocardial Infarction for an EKG signal versus a non-ST-Myocardial Infarction, and other physiological markers of an EKG signal. From experiential case-files there are EKG amplitude and frequency components that determine reading of the EKG measurement. The Clinical decision guidance can observe this behavior by finding the learning identifier describing the outcome with the properties read by the EKG of large number of similar experiential case files.

As an example, the experiential case-files can be trained by medical educators and medical practitioners, such as disclosed herein. The experiential case-files can be read from one guidance system to another to relate sub-sets of dimensional information and learn from it. This extends to looking at diagnosis transition to treatment and looking back to diagnosis from known data assimilation. The clinical guidance experiential case-files can be grouped by a state manager to read information that can relate not only time-stamping, but include any of the Clinical guidance variables, turning points similarity signals or base-line changes, decision, testing hypothesis, differential, and the like. The relevant similar experiential case-files that lead to diagnosis for a can generate search criteria for lookups to external data sources of their treatment to compare how they relate to the index patient. This can be contextualized using Natural Language Processing (NLP) methods known to those in the art, such as sentiment, n-grams, intended classification set of synonyms, and semiotics, which indicate the sense of writing, machine translation of predicate, and organizing the medical language to ascertain specific questions for evidence based guidelines. As an example of the search criteria, it can be sent by API to a search and recommender system. A search and recommender system is configured to finds the healthcare literature information from keyword queries and recommends answers from the healthcare literature. In an example, this could be searching the medical journal articles or an evidence based clinical resource for current clinical information and pharmaco-kinetic drug treatments.

Figure 18:
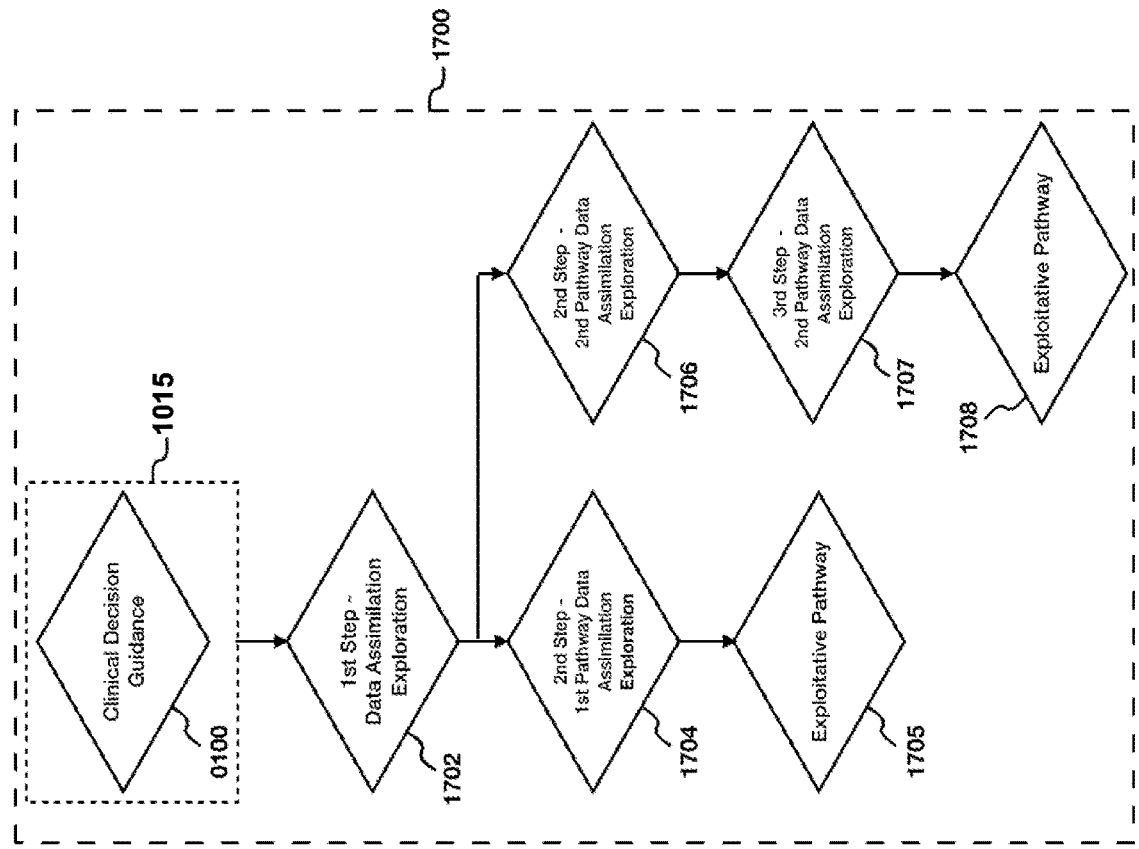
FIG. 18 is a flow diagram illustrating an example of a turning point exploitative pathway analyzer.

FIG. 18 is a workflow diagram illustrating an example method of Clinical guidance to determine a turning points exploitative pathway 1705 or 1708. In the example of FIG. 18, the method is programmed to implement a turning point exploitative pathway analyzer 1700 in clinical decision guidance system 1015 that reads a first step of data assimilation exploration 1702. From the data assimilation exploration 1702, the look-ahead 1700 then forks to a 2nd step for each of two different explorative pathways 1704 and 1706. More than two pathways may be explored in other examples. The first pathway 1704 finds a turning point exploitative pathway 1705 in response to the data assimilation exploration at 1702. However, the second explorative pathway 1706 is unable to locate an exploitive pathway and requires additional data assimilation exploration 1706 and thus explores a 3rd step data assimilation 1707. In response to the $3^{rd}$ step data assimilation for the second pathway, the second explorative pathway then finds an exploitative pathway 1708. This approach may be repeated by clinical decision guidance 1015 to build a combinatoric of turning points found from exploitative pathways 1705, 1709 as a transition from the exploration pathways 1704, 1707 as a transition from the exploration pathways 1704, 1707 that the practitioner can related to the index patient related to the index patient in determining of which tests and/or examinations to perform and what is expected to be learned from the tests and examinations were they to be performed.

As an example, the turning points from exploitative pathways 1705, 1708, as a transition from the exploration pathways 1704, 1707, respectively, can investigate in response to either the healthcare practitioner input or data analysis by the clinical guidance for treatment options and explore how they will perform so a particular diagnosis can be re-evaluated during treatment. The exploration can continue (even if treatment is false) in order to determine what next examination or test should be performed to better understand the patient's condition. Based on the turning points identified by respective explorative pathways, the clinical decision guidance 1015 (e.g., clinical guidance system 0100) can determine autonomously what test should be performed and/or notify the medical practitioner for his or her intervention.

As a further example, the data assimilation exploitative pathway turning points, demonstrated at 1705 and 1708, explain the testing hypothesis. For example, they inform the physician how likely a condition is from predictive models. They compare risk factors and transitions from diagnosis, treatment, and even prevention. The medical practitioner can perform tests and exams that will identify similar clinical case studies (see—FIG. 20). The scored common factors are modified to include patient relevant data and population health statistics of probability (if so desired). The turning points as exploitative pathways 1705, 1708 from the transition exploration pathways 1704, 1707 can look for these aspects on local populations by means of a specific policy. As mentioned, the exploration may also execute instructions programmed to identify minimalist states that is exploration pathway before any exploitative pathways is identified. This combination of data and policy may be stored in the system as local guidelines.

Figure 19:
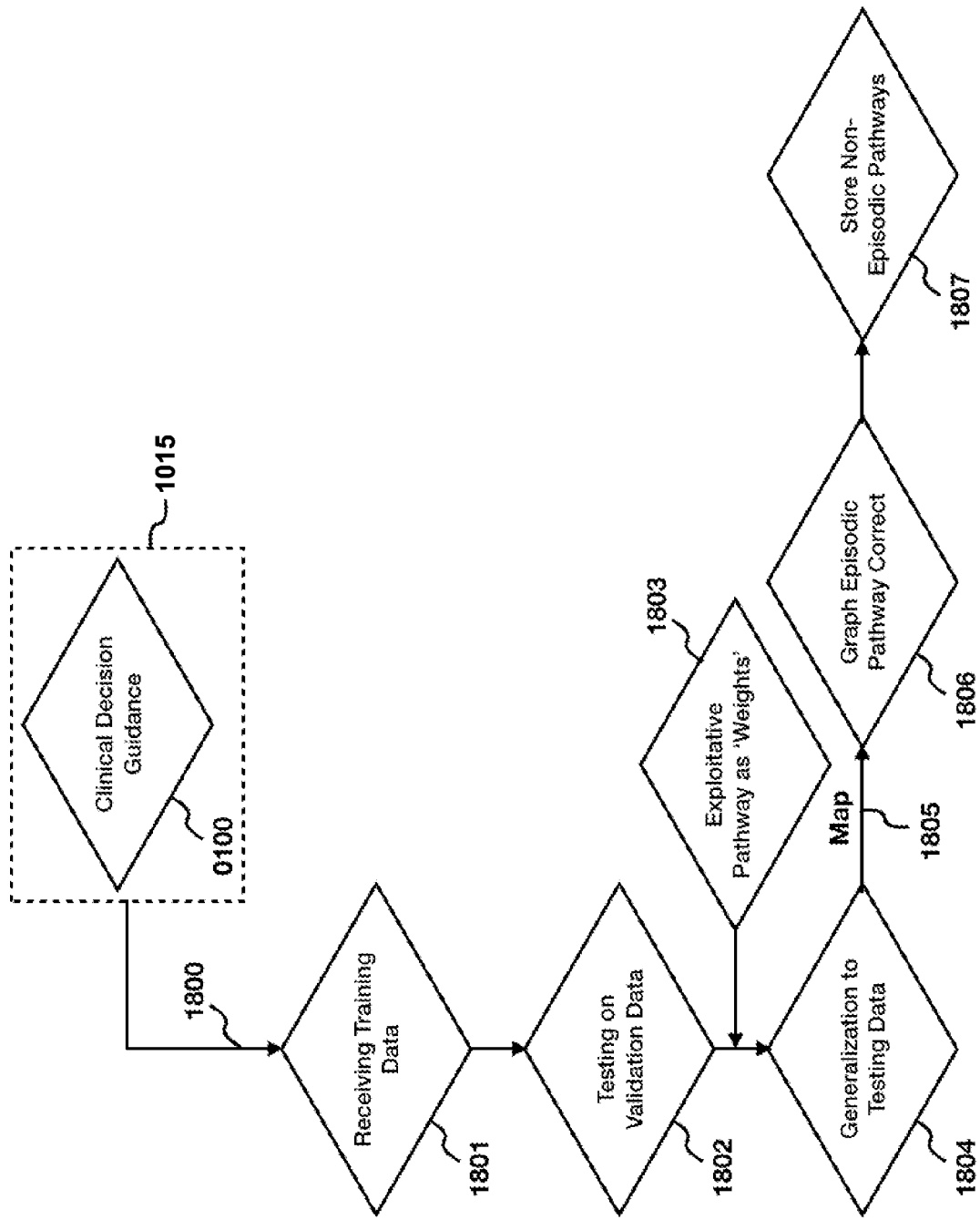
FIG. 19 is a workflow diagram illustrating an example of a policy driven method implemented by System Clinical guidance.

FIG. 19 is a workflow diagram illustrating an example method implemented by clinical decision guidance system 1015 using the policies of the Clinical Decision Guidance 0100. For example, the Clinical Decision Guidance 0100 is programmed to collect codified medical data with taxonomy 1800 and to receive training data 1801. For example, the received training data 1801 are in different categories and need to be normalized in order to correlate results from other methods. Example categories includes cardiovascular, respiratory, primary care, maternal health, mental health, and any type of medical discipline or combinations thereof. The taxonomy and training data are tested against the validation data at 1802 in order to find the exploitative pathway as weights 1803 from exploration. In this context, the weights describe the amount of steps to exploitative pathway during exploration. Testing on validation data 1802 may be drawn from already studied experiential case-files by healthcare and medical practitioners, such as utilizing known methods used for machine learning to determine a receiver operating characteristic (ROC) curve for number of steps to find the exploitative pathway 1803. The weights thus define how many decision steps or next states are required to then find the exploitative pathway. This can be many or small compared from training data 1801 in comparison to validation data 1802. The generalization 1804 is mapped 1805 to provide a graph (e.g., that is displayed on a display device) indicating a level of correctness for the episodic pathway 1806. For example, the graph episodic pathway 1806 provides an illustration of how accurate the system was, where it was correct, deviation of pathways from experiential case-files, which can include testing data 1804. Additionally, non episodic pathways from the graph may be stored at 1807.

The training of the clinical decision guidance 0100 validates how much it has learned from experiential case-files needs to be understood. For example, such training can be implemented with respect to pathway analysis. There may also be training for generative models to see how they compare with the clinical guidance that is being provided by the systems and methods herein. In an example, the training model can be implemented for exploring how accuracy increases with increased training case-files. The training model can also be implemented to show how the system's capacity for learning is affected by adding more training data. A trajectory of the learning (learning meaning the number of steps to arrive at a conclusion) may be made for the system with more complex information and case-file data.

Another analysis applied to the reinforcement learning framework is the behavior of scored common factors for the clinical guidance making next step decisions. For example, the action value function is compared to actor critic models by using the receiving training data 1801 to score the most similar experiential case-files as the critic and testing on validation data 1802 as the actor. For example, the behavior of scored common factors may be analyzed by stating what a practitioner (e.g., physician) serving as the training data 1801 would do based on prior similar experiential case-files, and classifying how they relate to similar case-files of the validation data 1802, or even using generative models that to reduce the error aim at learning the true data distribution of the training set so as to generate new data points with some variations from the experiential case files and how they adjust with similar experiential case-files.

The graph 1806 concludes at episodic tasks and shows statistics of the system and its review of correlated analysis. Finally, a comparison is made with decisions made by other samples of medical practitioners from a particular or group or groups.

Figure 20:
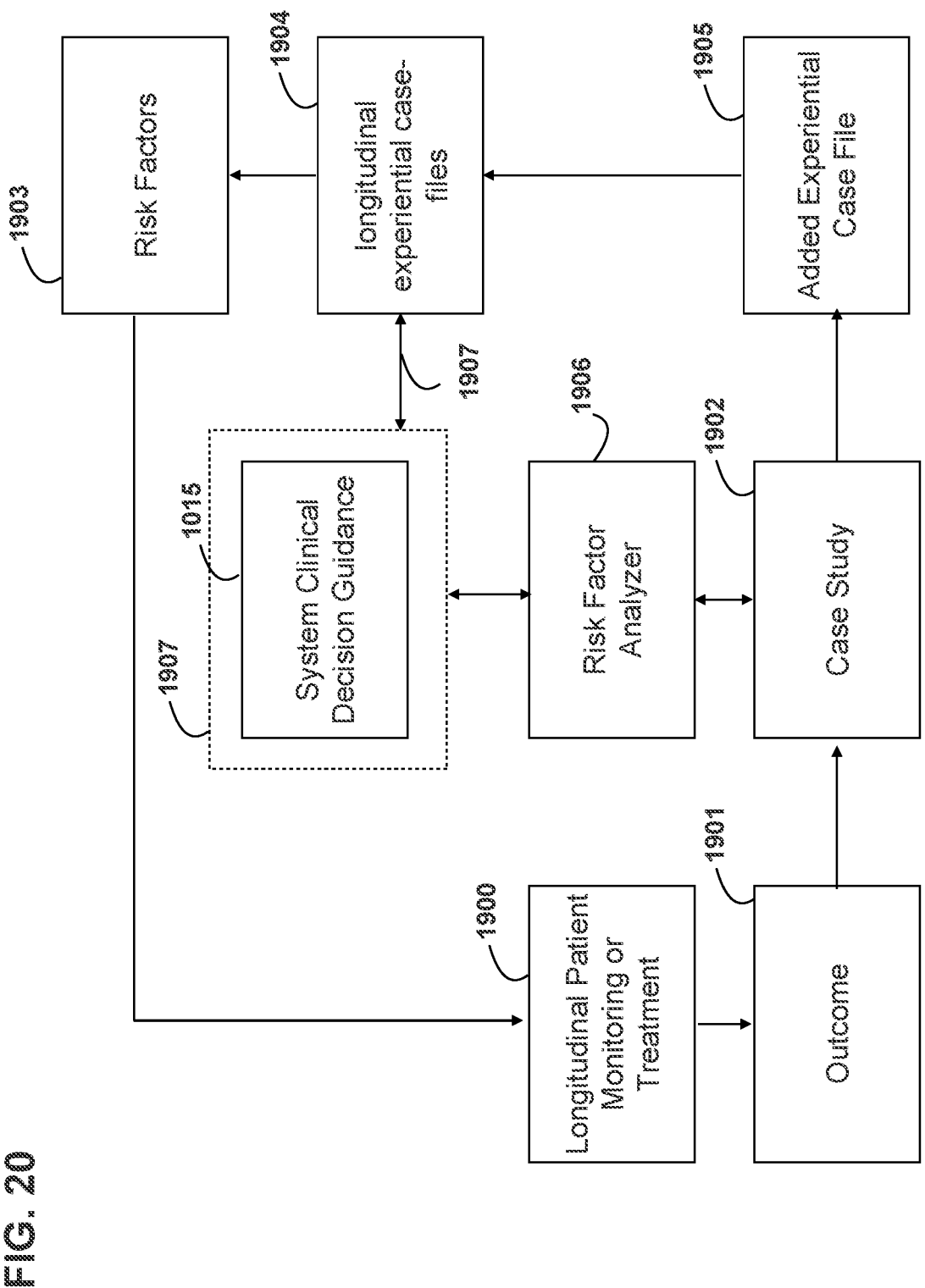
FIG. 20 is a flow diagram is a workflow diagram that illustrates risk factor analysis from longitudinal experiential case-files.

FIG. 20 is a workflow diagram that illustrates risk factor analysis from longitudinal experiential case-files. For example, the analysis identifies when to test risk factors from a case study that includes diagnostic, genetic tests, patient exam, population health, and the like by observing similarity of longitudinal experiential case-files 1904. The clinical guidance system 1015 finds the similarity of index case files 1907, such as new EHR data input such as diagnostic, genetic tests, pharmacoepidemiology, patient exam, population health, longitudinal data, etc., where the risk factor analyzer 1906, which is analogous to the pathway analyzer 50, is programmed for identifying the risk factors 1903 from the longitudinal experiential case-files 1904 that is part of the clinical decision guidance system 1015. The risk factor analyzer 1906 is analogous to a learning identifier, which searches from the clinical decision guidance system 1015 to find similarity in the longitudinal experiential case-files 1904 from the index patient the risk factors 1903. In an example, risk factors 1903 are how an index patient condition could progress if not monitored or treated in time. The healthcare practitioner determines a course of longitudinal monitoring and/or treatment 1900 to early prevent, alleviate, or minimize the risk factors 1903. The outcome 1901 of the longitudinal patient monitoring or treatment 1900 produces a case study 1902 example that is added experiential case files 1905 and thus becomes part of the longitudinal experiential case-files 1904. The case study 1902 includes information that describes how well the monitoring was identified and treated for the index patient.

An example objective of the identifying the risk factors 1903 is to reduce hospitalizations. The longitudinal patient monitoring or treatment 1900 may be derived from health apps, wearable sensors, medical imaging with deep radiomics, early cancer diagnostic, and the like. The risk factor analyzer 1906 can be programmed to implement a look ahead function with respect to similar case files over time to see if the index patient has risk factors that can progress into hospitalization. The risk factor analyzer 1906 can also recommend a diagnostic test.

The case study 1901 uses risk factor analyzer 1906 to find how the outcome 1901, which is determined to reduce, minimize, or alleviate the risk factors 1903, compares with the similar longitudinal experiential case-files 1904. For example, the risk factor analyzer 1906 looks ahead for longitudinal experiential case-files 1904 progression when the index patient is 10 years older to then find similar longitudinal experiential case-files 1904 would compare an outcome 1901 with how the risk factor alleviates a medical condition from developing or further progressing. The risk factor analyzer 1906 may include what-if scenarios by testing a pathway analyzer 50 in FIG. 1 for identifying risk factors 1903, such as performing a diagnostic test and how that could identify potential risk factors 1903. In an example, the what-if scenarios can be simulated and automated to alert the healthcare practitioner of a way to test for a risk factor 1903 or what-if scenarios using population health metrics.

Figure 21:
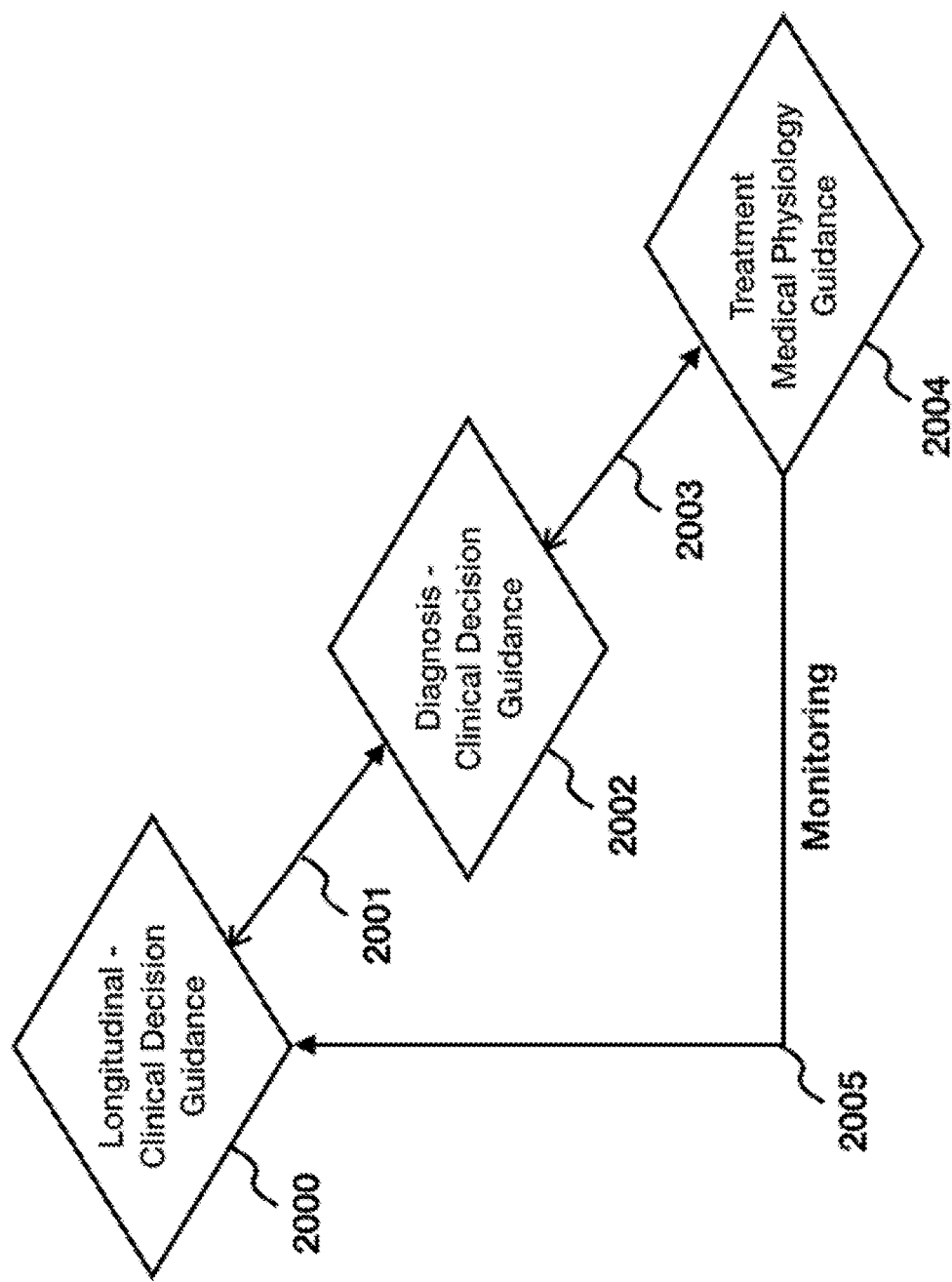
FIG. 21 is a flow diagram that illustrates a Clinical guidance that transitions information from longitudinal data, diagnosis, and treatment with monitoring data.

FIG. 21 is a flow chart illustrating an example method of generating and storing longitudinal data by the Clinical decision guidance 2000. For example, the longitudinal Clinical decision guidance 2000 is programmed to exchange data 2001 with the diagnosis category of the Clinical guidance 2002. The diagnosis Clinical decision guidance 2002 also is programmed to exchange data with treatment medical physiology Guidance 2004 that is programmed for monitoring 2005, such as by patient input to determine effects from treatment. For example the monitoring at 2005 can include medically imaging the patient to see how treatment is improving, and the like. The Guidance at 2004 based on the monitoring 2005 may be utilized by the Diagnosis-Clinical decision guidance 2002 to acquire data representing a biological and medical behavior of the patient condition.

As an example, longitudinal Clinical decision guidance 2000 is programmed to learn from IoT/health sensors (and/or other sensors and devices, medical diagnostic(s), medical imaging) as well as to interpret the diagnosis results from monitoring 2005 information. For example, the Clinical decision guidance 2000 can implement such learning by using a decision hypothesis from the Diagnosis-Clinical decision guidance 2002 in the clinical guidance system 0100 and for other new information through diagnosis and treatment. The interpretation of IoT/health sensors provides support or lack thereof to the healthcare practitioner for the treatment medical physiology Guidance 2004 from the Diagnosis-Clinical decision guidance 2002 using the learning identifier similar experiential case-files to find similarity between IoT/health sensor data results. For example, the longitudinal Clinical decision guidance 2000 is programmed to find explorative and exploitative pathways, such as using a pathway analyzer 50 from the IoT/health sensor data across each particular longitudinal, diagnosis, treatment, and monitoring in real time as it is entered. The new information affects each new data assimilation step and updates the system similar to a controlled process. This can relate prior history of the patient and continue to update the data assimilation of the patient such to provide a corresponding longitudinal data electronic health record. As a result, the longitudinal Clinical decision guidance 2000 generates an evidence based guideline for each patient.

Figure 22:
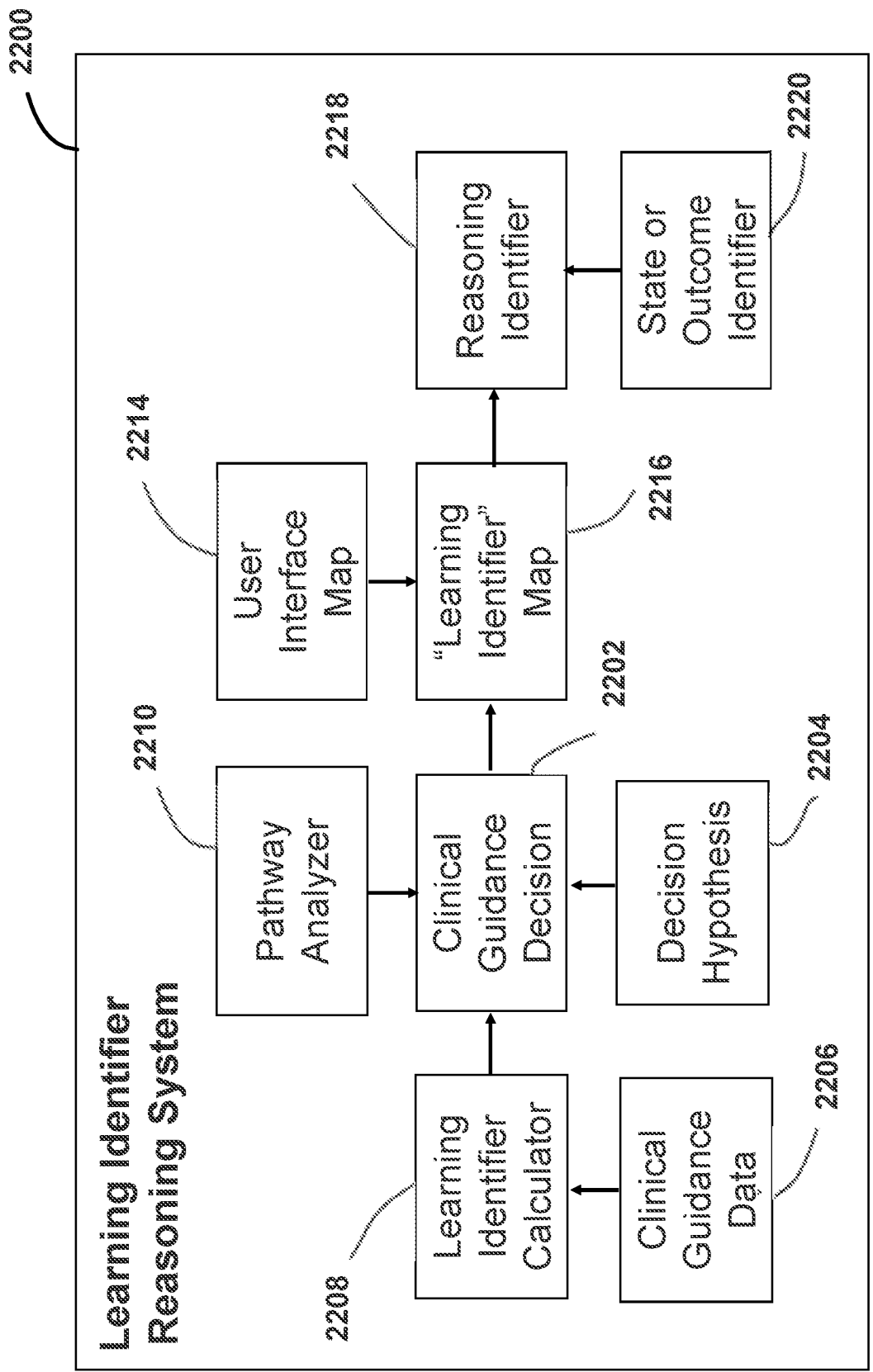
FIG. 22 is illustrates an example of a learning identifier reasoning system.

FIG. 22 illustrates an example of a learning identifier reasoning system 2200. The system 2200 is operative to compare the clinical guidance decision 2202 that is provided from the decision hypothesis 2204 of the healthcare practitioner (e.g., corresponding to learning identifier 32). The clinical guidance decision 2202 also receives a learning identifier that is generated by learning identifier calculator 2208 (e.g., learning identifier calculator 26) based on clinical guidance data 2206. The learning identifier is programmed to find similar experiential case file related to the index patient, and the reasoning identifier 2218 explains the decision of what the healthcare practitioner chooses as a decision for which experiential case file is similar to the index patient. The clinical decision guidance 2202 thus is programmed to create a contextualization of the patient case file being evaluated by the healthcare practitioner based on the learning identifier and decision hypothesis of the healthcare practitioner. The reasoning of the index patient case file derives from the contextualization by means of the pathway analyzer 2210 (e.g., pathway analyzer 50), which is programmed to determine the properties of diagnosis, treatment, and monitoring. For example, the pathway analyzer 2210 is programmed to implement methods for exploration, exploitative, turning points, and categories of environment, sub-environment, and sub-sub environment which are relevant to study the index patient case file from similar experiential case-files, and dissimilar factors in the case file. The reasoning is the derivation of the healthcare practitioner decisions in a software codified language from a learning identifier map 2216. For example, the learning identifier map 2216 is configured to display a user interface map 2214 on the display to visualize the reasoning of the case. The healthcare practitioner can modify or accept the reasoning. This is written and confirmed and stored in memory as the reasoning identifier 2218, which can be a new state or outcome state identifier 2220. The new case file state is updated with new information.

By way of example, the case file state and outcome state identifier 2220 is a patient encounter, longitudinal data from monitoring of the patient, such as, heart monitor, whole genome sequencing at different time intervals, cancer diagnostic, or social and environmental factors. The feedback of the reasoning by the healthcare practitioner serves as both identification to specify whether the case file contextualization is correct and to improve the similarity accuracy of case-files or understand the uniqueness of the index patient case file. The ability to update the identification of contextualization environment, sub environment, and sub-sub environment, etc. reviews the analysis of the Clinical guidance to ascertain better the intuition of the healthcare practitioner. This is particularly useful for understanding the social and environmental behavior of the patient. An aspect of the healthcare practitioner in evaluating the patient is their perception of the patient during the patient encounter. For an example, during a patient encounter within an intensive care unit (ICU): is the patient breathing moderately or fast when their blood pressure is taken; does the patient blood pressure jump because of a ventilator; is the blood pressure increase due to medications, condition that sent him/her to the ICU, or a host of other things; and what is the healthcare practitioner's experience in how they perceive and measure the patient relative to other patients, e.g., anxiety, nervousness, and observation of syncope. As an example of the clinical guidance data 2206, as patient electronic health recorded information, this information is normalized to the healthcare practitioner and mapped by the topology from FIG. 10 to create a state space of i-dimensions 0906 to find a learning identifier from similar experiential case files and the index patient.

The learning identifier map 2216 is programmed to display relevant information about the patient. For example, the medical practitioner may want to see the case file for the patient encounter, patient longitudinal information, similarity of case files during the patient encounter during look ahead similarity of longitudinal case files, population health metrics, and the like. The learning identifier map 2216 thus is programmed to perform data analysis from the reasoning identifier 2218, and automate the analysis as behind the scene analysis to identify behavior of the patient record. For example, the data analysis uses the pathway analyzer 2210 (e.g., pathway analyzer 50) for the index patient environment, sub-environment, and sub-sub environment, etc., and collective index patient environment, sub-environment, and sub-sub environment, etc., from the similarity of what is considered normal of a patient and what is considered a concern from using a learning identifier by finding what other healthcare practitioners found similar experiential case files and healthcare practitioner decisions. The learning identifier map 2216 is able to display information for home health visit, or mobile health app, for example. The healthcare practitioner can request with private-public key permissions to update the mobile health app, wireless monitor, or medical electronic device. The data from the learning identifier map 2216 may be structured as either or a combination thereof, JavaScript, Python Tables, JSON, CSV, and graphing software format, known by those in the art. The learning identifier map and reasoning identifier 2218 are programmed as an API request as a set of software instructions that can be run by a mobile health app, health sensor, medical device, and the like.

As a further example, the reasoning identifier 2218 is programmed to relate differential diagnosis and treatment of the patient. This information is stored between patient encounters to update the longitudinal learning identifier of the case file, which is utilized by the clinical guidance decision 2202. For example, the clinical guidance decision is programmed to perform look ahead of the longitudinal learning identifier to understand (i) properties of the index patient case of what are complications, (ii) diagnosis and treatment assumptions from the learning identifier map 2216 and reasoning identifier 2218, and (iii) what can be learned from the patient and follow up patient visit, monitoring, and new electronic health record information. This can be derived from team based care approach, that is referred to as including various combinations of physicians nurses, physician assistants, social case workers to diagnosis, monitor, and treat a patient. A team based care approach herein is broadened in definition to include health apps with patient input, collection of health sensors, with one or combination of healthcare practitioners.

The social and environmental determinants to personalize medical and practitioner intuition in the EHR require quantifying patient information. For example, questions of the like are needed to contextualize a case file, such as to ascertain 1) is the patient taking their medication, 2) what is the frequency the patient is taking their medication, 3) has the patient encountered issues in the past requiring medication dosage changes, 4) is the regiment of the medication working or not based on the dosage, 5) is it necessary for the patient to try a different medication or continue with the treatment, and 6) whether the patient is using a diet that effects the patient medication, such as, taking the medication at a particular hour. The contextualization further may encompass additional patient behavior and information, such as an indication of whether the patient is generally happy, but today he/she seems down. The clinical guidance decision 2202 may include such categorically sub-decisions for the patient behavior in the learning identifier map 2216, such as by enabling the clinical guidance decision to map from an environment, sub-environment, and sub-sub environment, etc., that is relevant to the index case. This information is presented user interface map 2214. As an example, the learning identifier map 2216 and reasoning identifier 2218 of the index patient case-file includes a collection of information from a team based care. Thus, more than one medical and healthcare practitioner can update each and the clinical guidance decision 2202 can generate a collective learning identifier map 2216. The reasoning identifier documents what is the healthcare practitioner decisions for the index patient case file.

The reasoning identifier 2218 describes the decisions of the healthcare practitioner from the pathway analyzer 2210 (e.g., pathway analyzer 50) for turning points to describe the decision hypothesis of the healthcare practitioner, the exploration and what has been learned by the healthcare practitioner in next steps from each state space learning identifier to what the healthcare practitioner found similar experiential case files and which next variables to study as a next state, and what tests, exams, and new data assimilation the healthcare practitioner can discover about the patient from look ahead analysis, and further policies used to guide the healthcare practitioner, such as, for the healthcare practitioner to first gather data for potential patient acute condition. The reasoning identifier 2218 thus provides a document database tabular description of the case file. The reasoning identifier may be stored in a database or patient case file blockchain. For example, the reasoning identifier is contained in a software tabular format like a blockchain. This describes the case file based on the index patient case file organization that is added to the learning identifier map 2216 and reasoning identifier 2218.

As a further example, the learning identifier map 2216, which is in a data structure format, provides information the healthcare practitioner decisions and how they relate the similar experiential case files that is analyzed by the reasoning identifier 2218. The reasoning identifier 2218 operates on the learning identifier map 2216 data structure and is programmed to store the results of the reasoning identifier 2218 in the clinical guidance system 0100 database. In an example, the database information for the reasoning identifier 2218 is de-identified, which is sent to a server to be included as part of the experiential data sets 20. As an example, the reasoning identifier 2218 database is updated from a particular environment, sub-environment, or sub-sub environment explored by team based care members. For example, the team based care reasoning identifier 2218 information includes social and environmental determinants, wireless monitoring of the patient, nutrition monitoring associated with medical imaging, and patient encounters, and reasoning for early diagnostic testing for cancer and recommendation.

Figure 23:
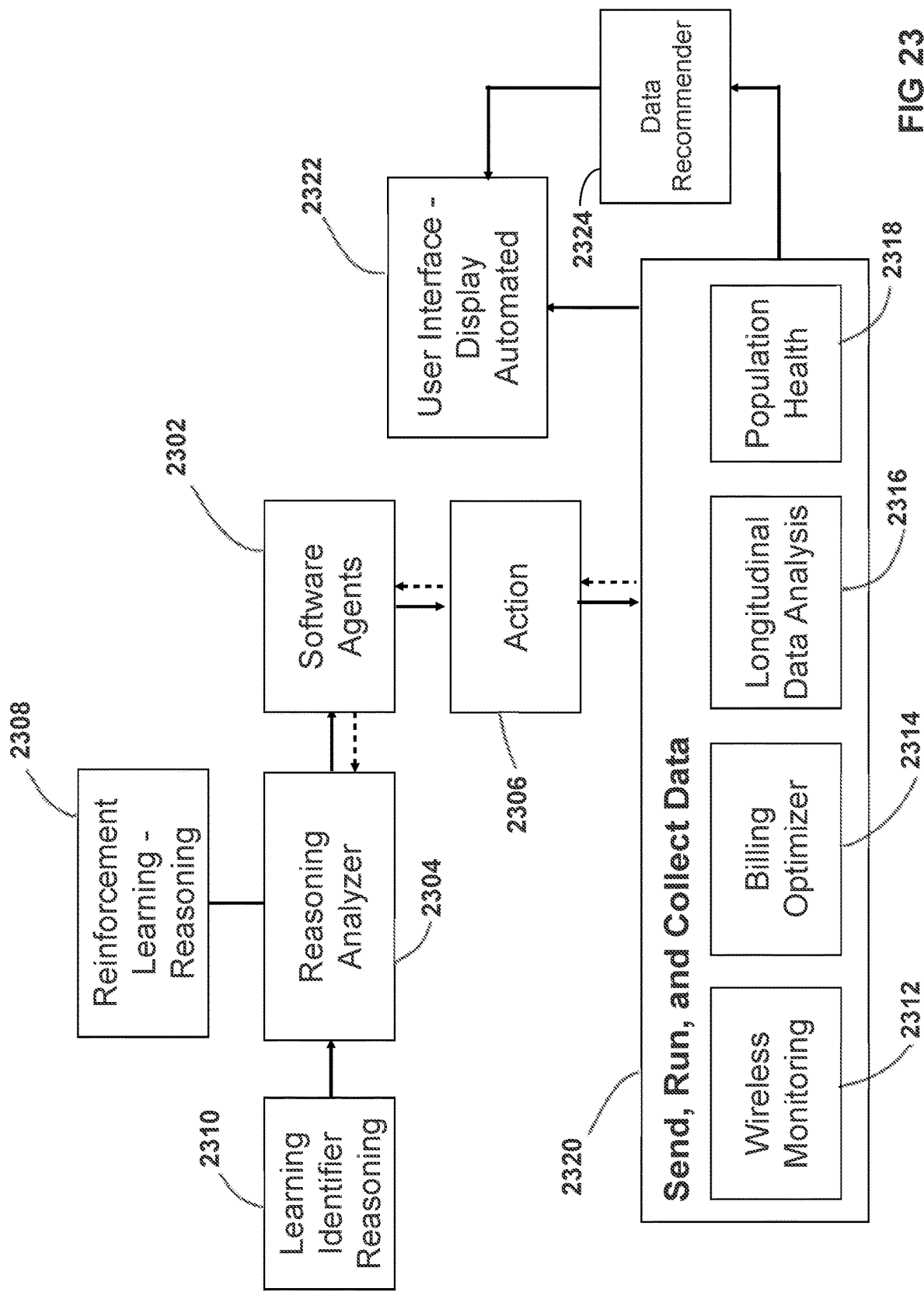
FIG. 23 is a flow diagram illustrating the learning identifier instructing at least one software agent action for patient management and EHR system software tools.

FIG. 23 illustrate of an example method of using the learning identifier reasoning system 2200 (FIG. 22) in a healthcare information technology infrastructure. For example, the learning identifier map 2216 and reasoning identifier 2218 are programmed to generate one or multiple software agents from a reasoning analyzer 2304 is programmed to prepare the data (e.g., index patient data) to produce a software agent 2302 to perform a software action 2306 running another software program. The learning identifier reasoning 2310 (e.g. reasoning identifier 2218) is a database of information that the reasoning analyzer 2304 reads and generates the software agents 2302 from the reinforcement learning reasoning 2308 that analyzes the case-file for tasks to be performed for which software agents 2302 are to carry out respective software tasks 2320. These software tasks 2320 may include an API requests for wireless monitoring 2312, billing optimizer 2314, longitudinal data analysis 2316 and population health analysis 2318. For example, the wireless monitoring task 2312 performs wireless monitoring of a patient. The longitudinal data analysis 2316, runs a software program, such as, for performing data analysis for an index case file using longitudinal data learning identifier, and may assign team based care tasks for another healthcare practitioner case file. The EHR system billing optimizer 2314 uses the information gathered from the electronic health record and the learning identifier map 2216. The tasks further can generate clinician healthcare notes or request a software program to generate the clinician healthcare notes, and perform population health metrics data analysis. Other software tasks 2320 may be utilized via software agents, and the like.

The system includes a user interface 2322 programmed to display the information for the healthcare practitioner to recommend or review the patient case file. This information from the software program 2320 creates a data recommender 2324, where one or multiple data recommendations are displayed on the user interface 2322. For example, the recommendations provide alerts to the patient by means of web socket from mobile health apps and medical devices. The data recommendation 2324 are automatically run for the patient or listed as a policy to provide information as data analysis, billing optimizer, and the like to the healthcare practitioner for review.

The one or multiple software agents 2302 are software code programmed to generate software instructions that run the programs from the case file reasoning and such software instructions are the action instructions 2306. The reinforcement learning reasoning 2308 culls information from the state information of the case file, and from the relevant environment, sub-environment, and sub-sub environment, etc., and provides the culled information to the reasoning analyzer 2304. The information could be the particular patient encounter, longitudinal data from the patient encounter, pathway analyzer information, turning points for exploration and exploitative, and the foregoing properties of the learning identifier. The healthcare practitioner can observe what the reasoning analyzer 2304 variables for the code that is generated from the learning identifier map 2216, or this process is automated. For example, the learning identifier map generates one or multiple keywords to be used for a function or method as a variable.

As a further example, the reasoning analyzer 2304 includes a command line interpreter. The reasoning analyzer 2304 is programmed to perform particular tasks 2320 through the agents 2302 by using software code as software variables, modules, functions, classes, or the like. The sequential tasks that are read to create the software agents 2302 that are instructions from the analysis may run within an embedded software program as part of the clinical guidance system. The reasoning analyzer 2304 can be downloaded and run in embedded software and different devices, such as including a mobile app, web app, and the like. The reasoning analyzer 2304 may issue commands from single healthcare practitioner or multiple practitioners in a team based care. The information from the reasoning analyzer 2304 may be encrypted by private-public key for wireless or other communication. The team based care reasoning analyzer is useful to pass data analysis between team members.

For example, relevant case file EHR and decisions, which are communicated and updated for each team based care using public-private key encryption, is based on their level of practice to perform data analysis. This level of practice is a policy (medical criteria), which assigns information from the reinforcement learning reasoning 2308, is dependent on the medical and healthcare level of practice. The action instructions 2306 may be sent by Bluetooth, Wifi, or other wireless methods or wired methods to another team based care member, wireless monitoring device, medical device, or mobile health app. The action instructions 2306 being sent may be encrypted and read by using public-private key encryption.

The action 2306 contains desired software command information (e.g., via software agents 2302) to test, receive, and review using the Clinical guidance. The test can produce a data recommendation, which is read by the Clinical guidance system and displayed on the user interface 2322. As an example, a type of recommendation would be to review the index patient case file to the similar case files for apprehending what is the behavior of the patient, such as based on social and environmental determinants during patient encounter, from longitudinal data, and in team based care, to explain the contextualization of the patient. The practitioner can review the electronic health record and provide additional analysis and instructions to team based care members by introducing keywords and the healthcare practitioner selecting commands to write a reasoning analyzer program. Other medical and healthcare practitioners develop these new minimalist and additional states for adding to the electronic health record.

As an example, the data recommendation is sent and used in a mobile app. The data recommendation is interoperable using an open source protocol. The medical and healthcare practitioner is able to request information from patient information. The patient, team based care practitioner, or mobile health app when using the interoperable protocol information can interact with the Clinical guidance system.

The user display on which the user interface 2322 is provided in foregoing methods and system for the Clinical guidance system may be implemented as a display of a smartphone, mobile device, laptop computer, augmented reality device, and the like.

Figure 24:
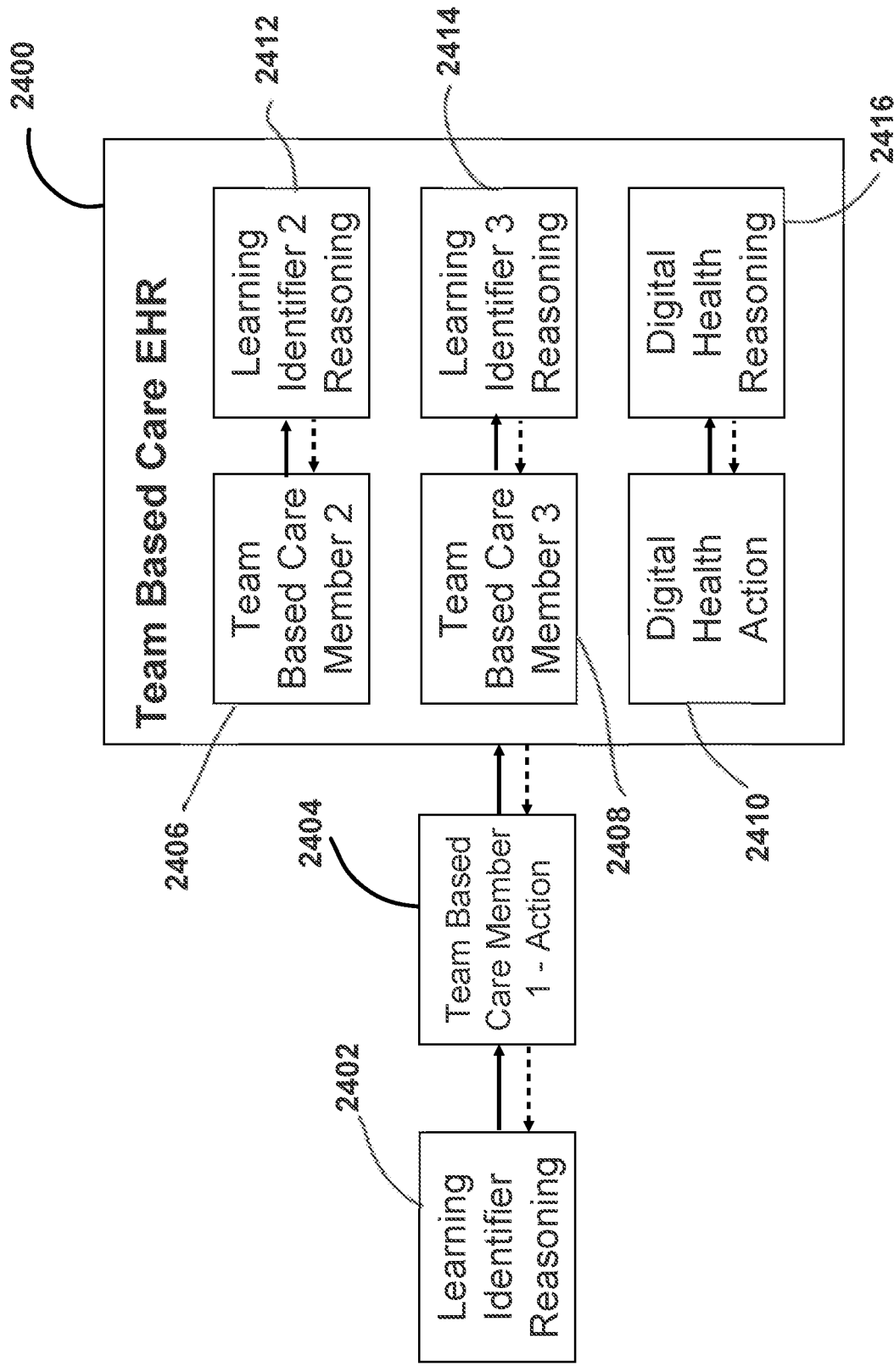
FIG. 24 illustrates an example of a team based care EHR system.

FIG. 24 illustrates an example of a team based care EHR 2400, which may implement clinical decision guidance disclosed herein. In this example, a learning identifier reasoning 2402 (e.g., corresponding to learning identifier reasoning 2310) is generated from team based care member 1 2404 as an action that is assigned to different team based care members 2406 and 2408 1 and team base care member 2. The team based care 1 2404 action software instruction may be implemented as a digital health app to gather patient data or perform a digital therapeutic, and generate a digital health reasoning 2416 of digital health app information, which the digital health reasoning 2416 data analogous to the learning identifier reasoning 2310 in FIG. 23. For example, each team based care member 2 and 3 2406 and 2408 employs digital health data to produces a respective learning identifier reasoning 2412 and 2414 to update the case file that is shared within the team based care Clinical guidance systems.

For an example, team based care is beneficial when tasks and information from the EHR 2400 is requested by a clinician to registered nurse to collect patient data for social and environmental determinants as the learning identifier reasoning 2 2412, 3 2414 and digital health reasoning 2416 is used as variable keywords to run software instruction codes. The team based care clinician further assigns (e.g., in response to a user input) the digital health app to collect information that is longitudinal exercise health data and health app EKG form a digital health reasoning 2416 as keywords with software instruction as the EHR requested by the medical health practitioner that is a software command. As an example, the software instruction is an API request. The clinician can observe a problem. A specialist team based care member would be assigned to review the health information, and make a recommendation, for example.

Figure 25:
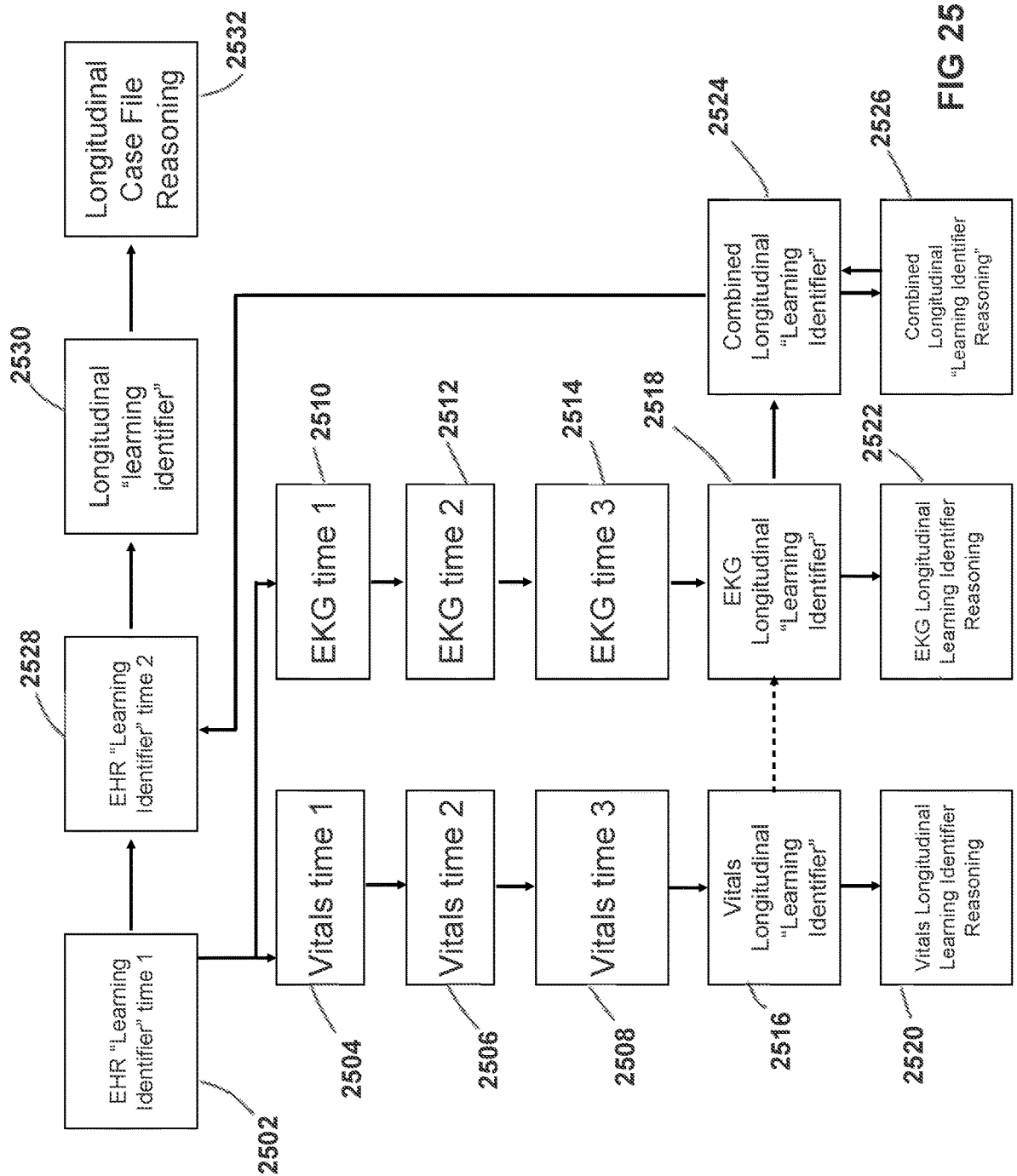
FIG. 25 is a workflow diagram that illustrates the Clinical Guidance generating reinforcement learning identifiers.

FIG. 25 is a workflow diagram that illustrates an example method for generating longitudinal learning identifiers. In this example, an EHR learning identifier at time 1 2502 collects longitudinal data of a specific environment, sub-environment, and sub-sub environment, etc. that is vitals at time 1 2504, vitals at time 2 2506, Vitals at time 3 2508. Concurrently with collecting the vitals at 2504-2508, the EHR learning identifier also collects EKG reading at time 1 2510, EKG reading at time 2 2512, and EKG reading at time 3 2514. From time 1 and time 3 a vitals longitudinal learning identifier 2516 in this timeframe new vital data, for example, is entered into a clinical guidance system 0100 (e.g., by a recorded digital health app, medical device or nurse) to reflect the electronic health record inclusion of the vitals information that was collected. The same is done for the EKG longitudinal identifier 2518. The longitudinal learning identifier reasoning is the contextualization of the decision hypothesis or exploration of longitudinal data pathways and looking at a pathway analyzer 50 in FIG. 1. Another way of longitudinal learning identifier reasoning explanation is in game theory, it is the dynamic equilibrium of the pathways to what it has learned from exploration from similar exploration case files and what can be learned from look ahead exploration and exploitative pathways that is relevant to the patient case file. As an example, the strategy is a manipulated Nash Equilibrium.

Each vital and EKG electronic health record updates specifically the relevant environment, sub-environment, and sub-sub environment, etc. in the state space. The update is the vitals longitudinal learning identifier reasoning 2520 and EKG longitudinal learning identifier reasoning 2522. These are combined to form a longitudinal learning identifier reasoning 2526 that contextualizes from similar case files using pathway analysis of combined specific vitals and EKG longitudinal learning identifier information. The pathway analysis generates the reasoning, wherein updates are made to the EHR learning identifier in what becomes time 2 2528 for the EHR Clinical guidance patient record. This becomes the longitudinal learning identifier 2530 for the index patient case file. The information results of similar case files from the longitudinal learning identifier 2530 is written as the longitudinal learning identifier reasoning 2532 that update analysis of the environment, sub-environment, and sub-sub environment, etc., and state space.

Additionally, the additional new longitudinal data for a specific longitudinal record of new specific environment, sub-environment, and sub-sub environment, and the like, such as after taking vitals and EKG, the patient is monitored for home stress test, this would then be combined with the longitudinal learning identifier 2530 that is re-evaluated.

As a further example, the longitudinal learning identifier 2530 is stored in either a relational or non-relational database. Information from the longitudinal learning identifier 2530 is de-identified to protect patient privacy and sent to a central or distributed servers for processing the learning identifier. For example, the longitudinal data analysis is stored in a central or distributed server and read to an individual computing system. For example, the computing system is a laptop, mobile phone, augmented reality device, and the like. The learning identifier finds similar case files specific to the higher or EHR lower level environments, e.g., EHR environments, sub-environments, and sub-sub environments, etc. The EHR may contain social and environmental determinants, vitals, genomic data, medical tests, medical exams, and the like, as the foregoing description.

Figure 26:
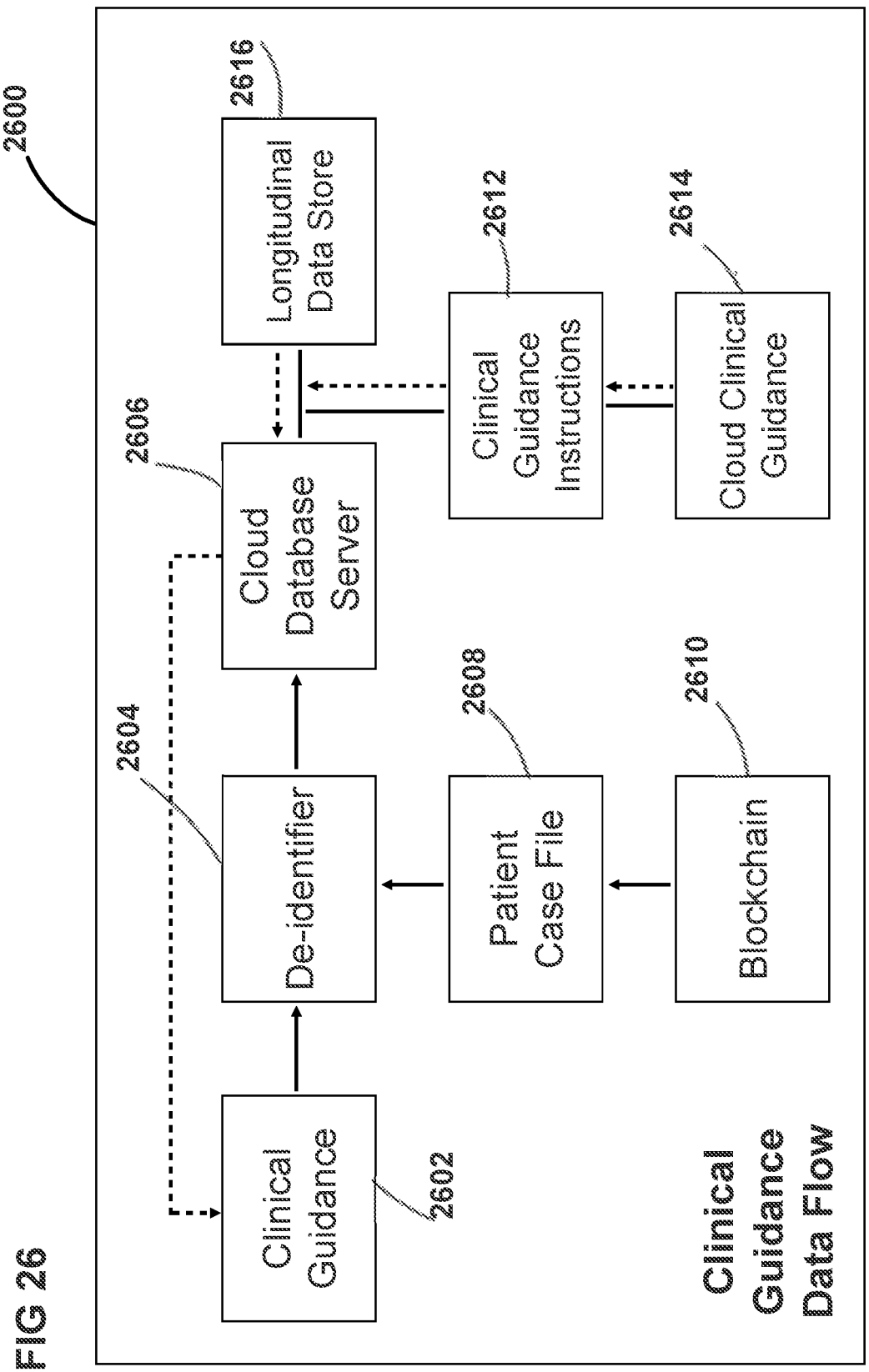
FIG. 26 depicts an example of a clinical guidance data flow.

FIG. 26 illustrates an example of a clinical guidance data flow 2600. For example, a Clinical decision guidance system 2602 (e.g., the guidance system 10 or 0100) includes instructions executing on an individual computer and/or local server. EHR identifiable patient information from the clinical guidance system 2602 is de-identified by a de-identifier 2604. The de-identified information may be recorded in a central or cloud distributed server 2606 as a collective of case-files that are combined in a single state space. The patient case file 2608 may be stored in a blockchain 2610, or one or more health facility servers.

The data analysis is performed for the learning identifier as clinical guidance instructions that are read by a cloud Clinical guidance that relate the instructions of the individual central or distributed server to the individual computer, or multiple individual computers in a team based care. The information exchange may be public-private key encrypted as disclosed herein. The EHR data that is de-identified forms a data warehouse longitudinal data store 2616 of the state space environment, sub-environment, and sub-sub environment.

As a further example, the de-identifier contains the structured format of the case file that includes the environment, sub-environment, and sub-sub environment, etc., such as by using document non-relational database linkers in the cloud central or distributed ledger. The non-relational database is read from one case file to another. After the de-identifier removes the patient identifiable case file information, this becomes an experiential case file, as disclosed herein. The de-identifier 2604 is programmed to strip all direct identifiers from all health information that can be used to identify a patient from whose medical record the health information was derived. The process for de-identification may include the de-identifier 2604 searches from the structured clinical guidance electronic health record, and associated medical record information to scrub the information. Within the Clinician guidance system 2602, structured patient identifiable information are tagged. The de-identifier further performs a search of the de-identified information and information that may contain partial information of the de-identification and removes this information by creating a query to find and delete the above information. Computer vision techniques, such as using convolutional neural networks and object detection, may be implemented to remove the identifiers by reading numbers, letters, and the like, in the document. Identifiers can be partial or full identifiable information. As an example embodiment, the de-identifier shifts the timestamp of the patient case file such as to obfuscate when the electronic health information was entered.

The clinical guidance flow 2600 returns the de-identified data of experiential case file to include only de-identified information that maps from the experiential case-files to a universal information template derived from the case file. The template of mapping information is greater or equal to the index patient case-file. Information is known or not when presenting the learning identifier reasoning 2532 (e.g., from the learning identifier reasoning 2402, 2310) in FIG. 25 as part of the user interface implemented by the clinical guidance system 2602. Information from the learning identifier may be displayed on the user interface as either a distribution, as a map that includes overlapping the case-files that are normalized, where only a collective of patient case file is shown, and maps of case-files are shown to a particular environment, sub-environment, and sub-sub environment, and the like. In an example, the patient case file is stored on the database as a collective of overlapping case-files that are normalized to the environment, sub-environment, and sub-sub-environment.

The longitudinal data store 2616 sends and retrieves the de-identified patient data. For example, the longitudinal data store 2616 is a non-relational database with linkers of the case files for the environment, sub-environment, and sub-sub environment. If the database is relational, it performs normalization for each environment, sub-environment, and sub-sub environment, etc. The information sent and received by the longitudinal data store 2616 and individual Clinical guidance may be encrypted using public-private key encryption and communicated as encrypted data, for example, using wireless communication methods of WiFi, fiber optic, and the like, known by those in the art.

Figure 27:
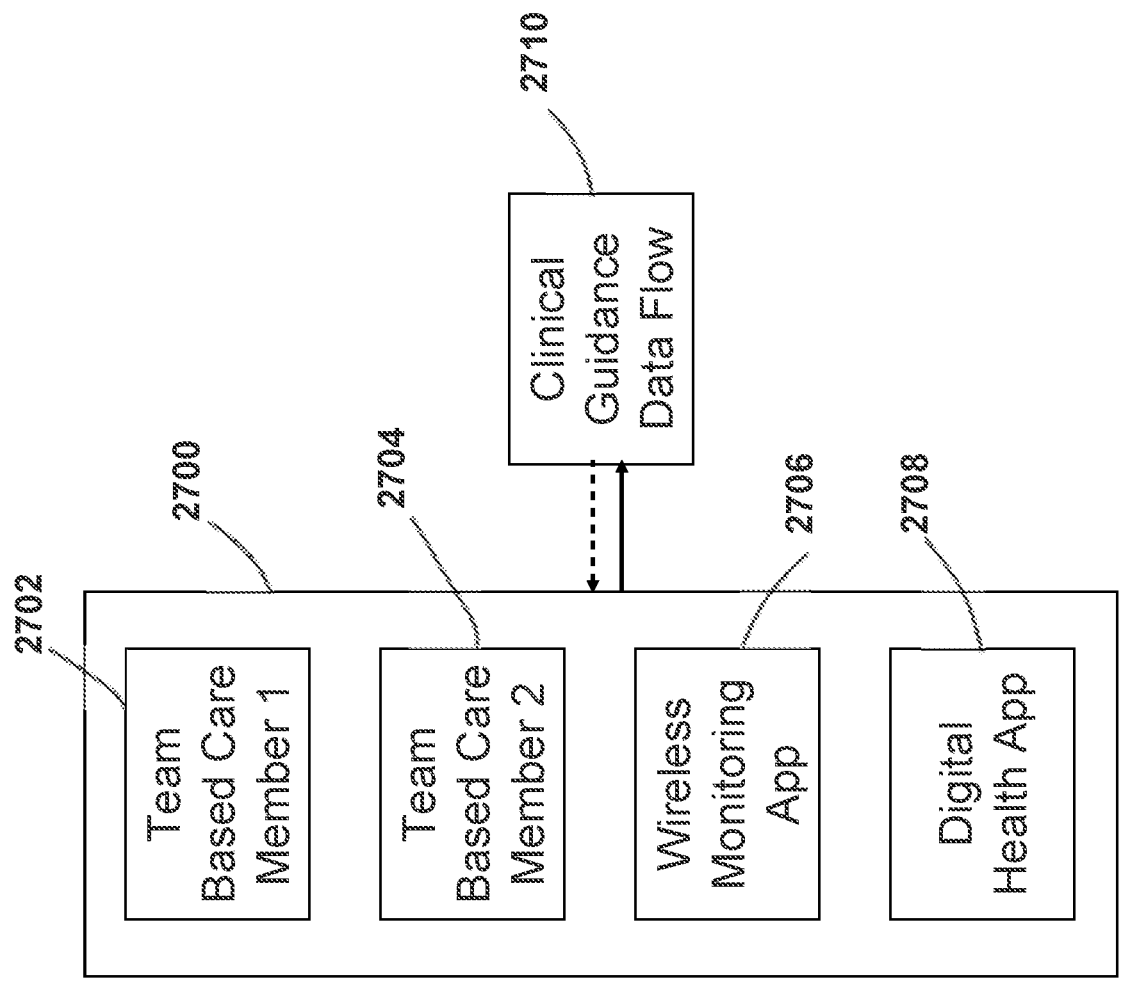
FIG. 27 depicts an example of a clinical guidance interactive team-based care EHR system.

FIG. 27 is a block diagram illustrating an example of a clinical guidance interactive team-based care EHR 2700. In the example of FIG. 27, the EHR 2700 includes team-based care member 1 2702, that uses a computer that includes clinical guidance, team based care member 2 2704, wireless monitoring app 2706, and digital health app 2708. The components 2702-2708 read to a clinical guidance data flow 2710 from the de-identified data on a central or distributed server 2606. The clinical guidance data flow 2710 (e.g., corresponding to 2600) is programmed to runs data analysis. The data analysis implemented by clinical guidance flow 2710 thus includes learning identifier, longitudinal identifier, learning identifier reasoning, longitudinal identifier reasoning, and other features of the clinical guidance methods and systems disclosed herein.

As an example, the information is sent by private-public key encryption for communications from the team based care member 2702 and 2704, wireless monitoring app, and/or digital health app 2708 to and from the central and distributed server or to each other. The private-public key encryption may be encrypted as single, two factor authentication, physical encryption, e.g., fingerprint, eye, facial identification, and the like. For example, the digital health app 2708 is a mobile app, and further may be an augmented reality app that uses computer vision or monitoring of taking medication. As an example, the identifiable patient case information is fully encrypted and not sent to the central or distributed server 2606, where only de-identified information is stored.

Figure 28:
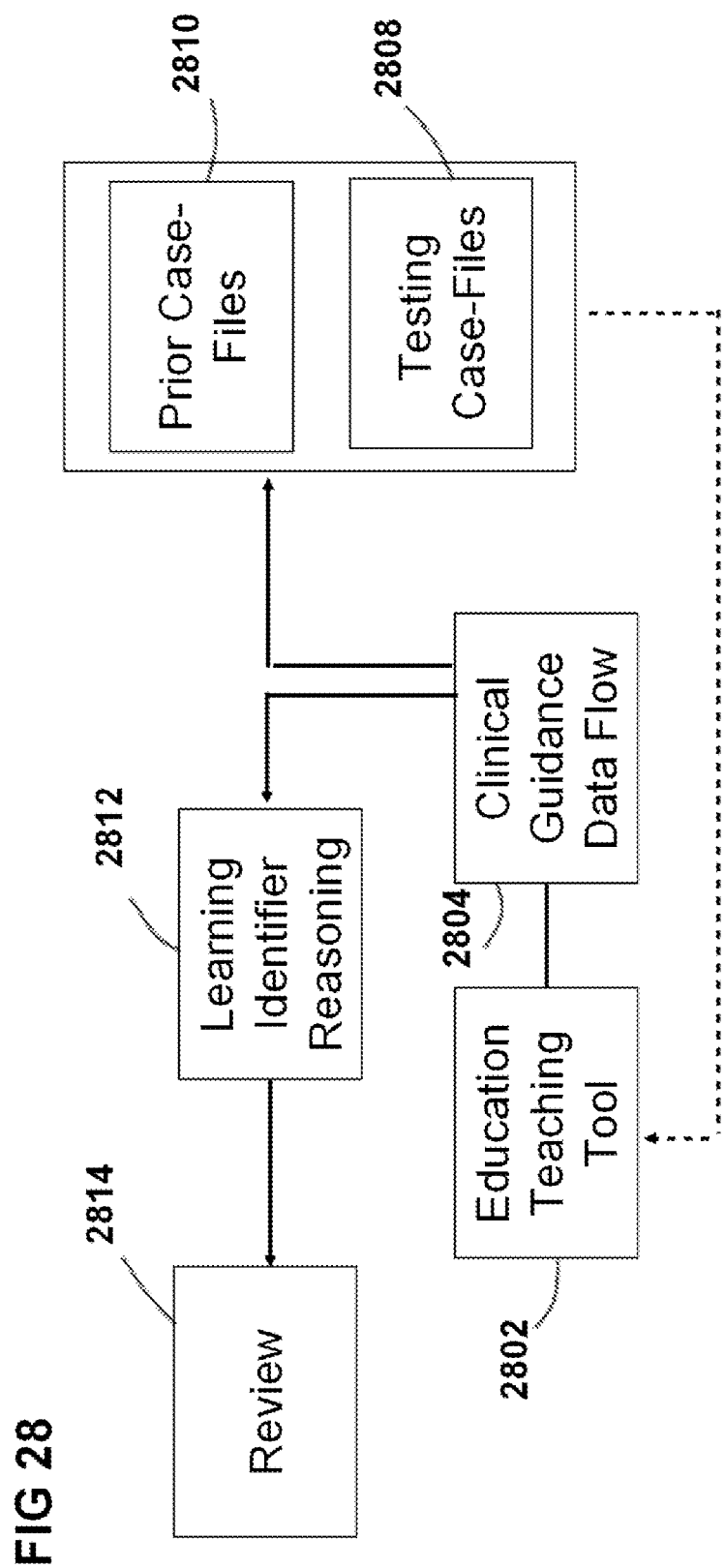
FIG. 28 is a workflow diagram illustrating an example method of an education teaching tool.

FIG. 28 is a workflow diagram illustrating an example method of an education teaching tool 2802 (e.g., for students and healthcare practitioners) that utilizes clinical guidance data flow 2804 (e.g., corresponding to data flow 2600) from a clinical guidance system (e.g., system 10 or 0100). For example, the education teaching tool 2802 is configured to review as a mock index patient or testing case files 2808 to analyze prior case files 2810 as the learning identifier. The student or healthcare practitioner creates a learning identifier reasoning 2812. In an example, a healthcare practitioner reviews 2814 performance of the education and case file learning based on the learning identifier reasoning 2812.

By way of example, the education teaching tool 2802 may be used to educate nurses and healthcare practitioners on mock and/or real case files. This is particular for nurses, which typically lack the clinical rounds of medical students. It is further useful as a teaching tool for healthcare practitioners to analyze longitudinal data. In an example, the education teaching tool 2802 collects only de-identified patient case file data 2806. Healthcare practitioner teachers can select case-file types for cardiovascular, respiratory, material health, primary care, and the like. They do this by inputting properties of an index patient file to review. Another means is to select topics, and save a directory of mock case files, and training de-identified case files used specific for educational purposes.

As a further example, the learning identifier reasoning 2812 (e.g., learning identifier reasoning 2402) for the healthcare practitioner is programmed to relate the similarity of the case files with the index patient and identify properties of the pathway analyzer (e.g., pathway analyzer 50, 2210), such as including the turning points, differential diagnosis and treatment, analysis of social and environmental identifiers, and how time effects the case file. The learning identifier reasoning 2812 (e.g., learning identifier reasoning 2402) is programmed to compare a new index patient or from experiential case-file testing data, and to evaluate the similarity of case files to relate if they made the decisions, what pathway explorative and exploitative pathway next states would lead the patient. The learning identifier reasoning 2812 is programmed to implement the map and data for decision that is reviewed by the health care teacher practitioner at 2814.

For example, the review 2812 utilizes a user interface that both the teacher and student can share their screens. The teacher is able to assign an environment, sub environment, and sub-sub environment. It is possible the student can review de-identified single case with permissions using a public-private key from practitioner and patient, such as to test the case file and to study aspects of the case file. The practitioner can use the review user interface the case file on which the student is performing clinical guidance, and assign notes of the case-file and their decisions. The practitioner can also select the learning identifier and the behavior of the case file if the patient performed such tests based on their recommendations. The screen capture implemented by the review user interface uses the same methods and systems as a team based care.

Figure 29:
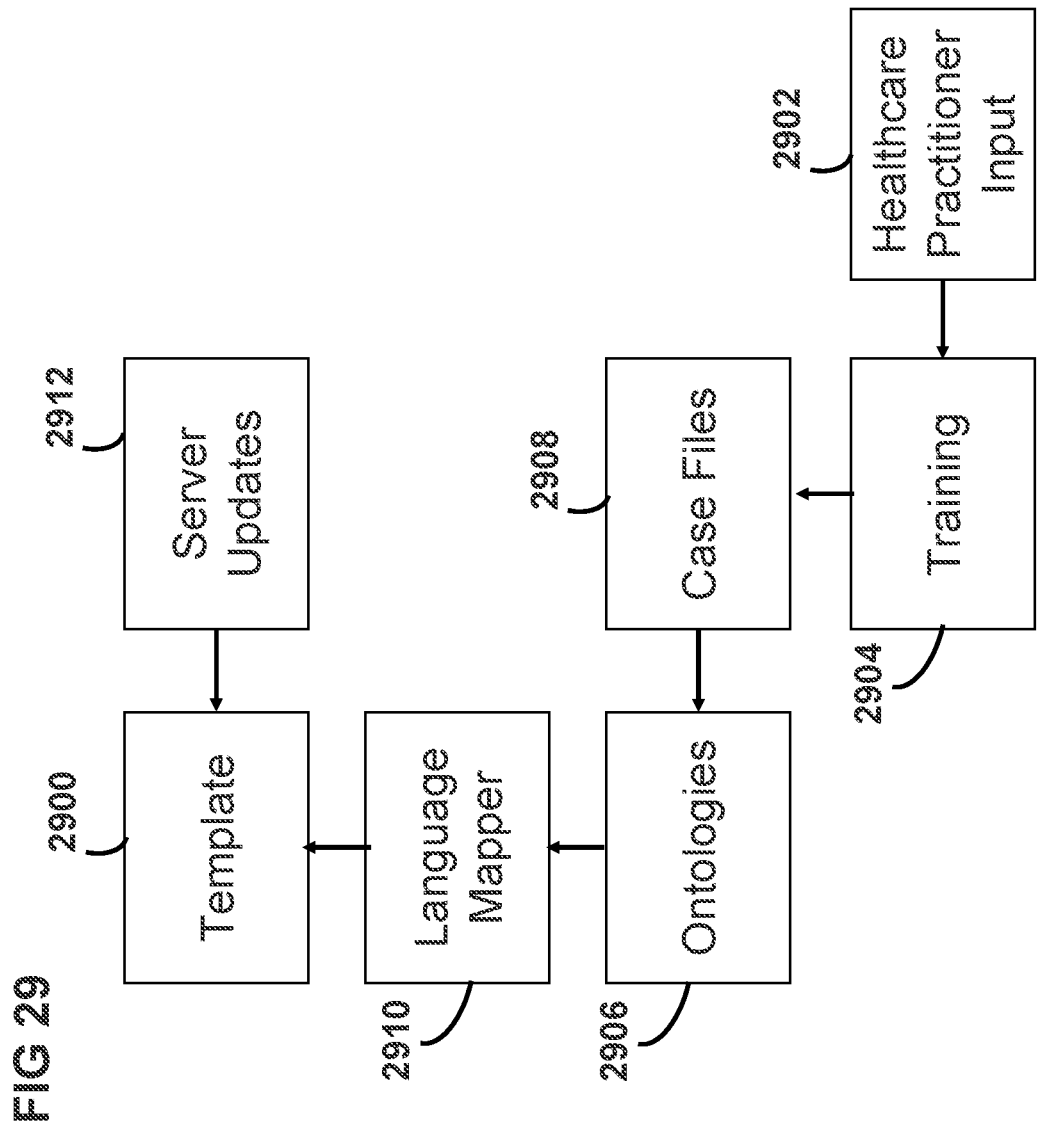
FIG. 29 is a flow diagram that illustrates a learning identifier decision reasoning to assign a software agent to recommend, and display the recommendation of determinant factors, e.g., new medications, risk, social and environmental.

FIG. 29 is a workflow diagram illustrating an example of a template that may be generated for EHR case file information. For example, the healthcare practitioner input 2902 is used to implement training 2904 to generate ontologies 2906 for a set of case files 2908. The ontologies 2906 are sent to a language mapper 2910 programmed to convert the language from the ontology to the template such as according to a Unified Medical Language System database (e.g., UMLS), and the like. The server includes instructions (server updates 2912) programmed to update the template 2900 to include new language and environment, sub-environment, and sub-sub environment, etc.

As a further example, the template 2900 is a structured information stored on the central or distributed server (e.g., server 2606) with the glossary language that is used by the experiential case files and state space of the experiential case-files 2908, and further the environments, sub-environments, and sub-sub environments. These experiential case files 2908 overlap their environment, sub-environment, and sub-sub environment to form a normalized data set, which uses the medical language and states of the template 2900. The template information is convertible into the language ontologies used by the healthcare practitioner. The data set for ontologies 2906 are loaded onto the server and/or on an individual computer. The ontology data set includes a data set like the unified medical language system (UMLS) offered by the NIH natural library of medicine, and the like, that are available.

The language mapper 2910 is a converter of language that the healthcare practitioner uses and selects from the case file record the ontologies based on recommendations of the template. The healthcare practitioner can see from the experiential case files the context of the information. Ontology information may be used by a natural language processing software program that is embedded in a mobile electronic device, e.g., cellphone, tablet, augmented reality device, and electronic recorder, laptop, or stationary computer and the like. The healthcare practitioner is able to relate both learning identifier information, voice commands for recommendations provided in the user interface, and data analysis, such as, longitudinal learning identifier and reasoning of information disclosed herein.

The foregoing server 2912 may be used by the healthcare practitioner program to update the template 2900 using private-public key encryption. The template additions or changes are created based on case-file's new environment, sub-environment, and sub-sub environments, etc. For example, the template 2900 is updated based on new medications and treatments by updating records and labeling the information by the healthcare practitioners as new information. This may be either recorded and approved into the template.

The following examples demonstrate various scenarios, methods and applications in which the clinical guidance system may be utilized for providing guidance in the context of administering healthcare, studying patient data or otherwise providing guidance.

As an example to increase capacity for healthcare practitioners as a software tool, nurses typically spend more time with the patient, they are able to increase the amount of information about the patient, and can play what-if scenarios to explore what are the new data assimilation pathways for differential diagnosis, and early prevention longitudinal nutrition and weight changes with review of test and exams with blood work and wireless monitor EKG in trying to improve a heart condition. They can present the analysis to a nurse practitioner or physician to make pharmacological changes or recommendations for continued monitoring by the nurse. This information is codified in the ICD10 codes for billing with a clinical guidance link to review the healthcare team based care note. It is possible the case file will codify based on a search optimizer the ICD10 codes that are linked with an additional billing code for the contextualization, and cost comparison with patient complexity level of care. This has further application for the LPN/RN, Nurse Practitioners, or both working together in a team-based care could use this information particularly for home-bound patients with multiple chronic diseases, where there is a shortage of Primary Care, and yet, nurse practitioners or physicians will need otherwise in this environment to make home calls, such as in rural areas of the country, or access points for those in underserved communities that have a shortage of primary care and for global health.

As another example, the electronic health record (EHR) system utilizes the learning identifier to simplify and automate billing. As EHR systems were designed specific for medical and healthcare billing. The ability to utilize the direct patient management health information can simplify and automate the billing process, and the physician note would ease the burden for clinicians. The ability to adapt from the learning identifier can define the billing codes produce a template clinician ('healthcare practitioner') note that is modified and updated with new clinical guidance tests, and that is deriving the template from the similarity of the crowd sourced patient case files for what is the what information is known of the patient based on the learning identifier comparing the clinical guidance explorative and when the healthcare practitioner(s) pursue tests and exams specific to their hypothesis of the outcome or called exploitative pathways for diagnosis, treatment monitoring, and subsequent updates of outcomes into the clinician ('healthcare practitioner') note. The information can Tehran search for rules and metrics set forth by Center for Medicaid Services to include these from the case-file into the billing, or provide a recommendation from the found similar case-files and reviews of their billing similarity using a learning identifier for this purpose.

As an example, the learning identifier, which provides contextualization and suggestions, can also make recommendations to update the user interface for the healthcare practitioner based on the patient case file and decisions thereof. The user interface application appears for example using vocal commands or automatically based on data analysis simulation of the learning identifier. This is useful for a healthcare practitioner to open user interface information for patients prior records as the patient describes pain and compare the longitudinal data of pain or the longitudinal data of the patient case file using a longitudinal data learning identifier for condition progression. This creates an environment where the healthcare practitioner does not have to click, as the system provides the information and recommendations. The healthcare practitioner can request the information to be tailored to their needs based on recommendations of similar case files from the learning identifier.

As an example, the use of the learning identifier for contextualization of the reasoning of the healthcare practitioner decisions and data assimilation of the case file from the useful clinical guidance is useful to perform the following by one or other team based members: request for patient case information, review of the patient case information, and clinical guidance analysis for a team based care, e.g., patient, family member, nurse, physician, physician-specialist, for digital health app, wireless monitors, medical devices, etc; and from home health, remote health access points, urgent care, outpatient facilities, hospitals, and the like to provide healthcare services. The learning identifier in the team based care setting can be automated triage to search for specific complications and health results from different team based care members. The information from the learning identifier can automate the clinical guidance for specific tasks among the team based care members, and provide alerts and notifications as interactivity from the EHR information gathered and decision hypothesis of the healthcare practitioner to review the patient case-file, or make requests for digital health applications to gather different or additional information. This would update the learning identifier clinical guidance information for the team based care, and update the contextualization of the reasoning of the healthcare practitioner decisions for the team based care.

To further the example, the update of the learning identifier is particularly useful for the index patient analysis of population health metrics and inclusive of electronic health record inclusive of social and environmental, longitudinal patient medical history, genomic data, and the like to review the patient case-file for each medical visit to create a patient record for risk factors for primary care health. The information may be hard-coded as a medical criteria as a policy in reinforcement learning framework as part of the learning identifier.

The medical information includes without limitation, medical conditions for primary care, chronic diseases, infectious diseases, mental health, neurological diseases, genomic counseling, opioid, etc. The clinical guidance applications comprised of, medical diagnosis, social and environmental determinants, prevention, treatment, monitoring, pre/post operative surgery, in-surgery, and the like. The electronic health record contain social and environmental determinants, genomic information, patient history, vitals, medical imaging, wireless monitoring, mobile apps, drug information including pharmacological information, etc. The application is extensible using patient experiential case-data to guide healthcare system policy, guidelines, local and remote population health analytics, and the like. The application is further extensible using patient experiential case-data to guide insurance policy.

As used herein, the term reinforcement learning is describing the field of machine learning, such as described in Sutton, R. and A. Barto 1998. Reinforcement Learning: An Introduction. The MIT Press. In particular, the reinforcement learning in the context of the framework disclosed herein is utilized as a technique whereby the reinforcement learning is providing generic functionality that can be selectively changed by additional software scoring of common factors tending toward a state of dynamic equilibrium in game theory called the learning identifier. The learning identifier is applied to the reinforcement learning policies and analysis and hypothesis testing from data assimilation information and relating common factors of the the experiential case-files.

By way of example, the reinforcement learning framework is defined for the purposes of medical applications as a modified version agent behavior of the Markov Decision Process (MDP) from the classic Bellman Equation in dynamic programming, current state (s), action (a), next-state (s'), reward (r), and policy ($\pi$). The current state (s) is the current state-space position. The action-reward (a-r) is dependent of the possible reward provided by the learning identifier as a function of a selected policy, and action is the step taken based on the clinical guidance of the medical practitioner. The learning identifier dictates the feedback about the step, and action is the path from current state to next state. The learning identifier is a score of common factors of the experiential case-files. It is further the learning identifier relates the MDP and data assimilation state-space. The policy ($\pi$) is a collection of policies set forth by the medical practitioner, hospital, insurance, pharmacy, etc., without limitation, cost of medication versus side effects, patient behavior, clinic guidelines, quality control/assurances from the software, or a combination thereof, and the like. Each learning identifier is dependent on the policies to find results optimal to the policies when scoring the common factors of the experiential case-files. The discounted rewards are dependent on the historical relevance of the experiential case-data.

The methods and systems of the learning identifier may include one or more of the following features: i) testable in behavior for generalization training, testing, and validation by the medical practitioner; ii) to learn from experiential case-files the relatedness of medical concepts; iii) develop decision based hypothesis; and iv) is explainable by means of inverse from results to find the initial conditions.

As an example of the learning identifier testing, it may pre-compute from known experiential case-files to evaluate system level performance for a medical practitioner to review and test the system. The inverse reinforcement learning capability, which is facilitated by isomorphic mapping of state-space parameters, allows medical practitioners to start from a selected (e.g., desired or hypothesized) outcome and look backwards of their patient's case. It is of further benefit to continue inverse reinforcement learning backwards from patient behavior to learn medical concepts and their relatedness. This is, for example, understanding the location of chest pain and effect on ECG signals, there are issues with left ventricular depolarization in reference to lack of blood flow across other parts of the body that is not pulmonary. As an example, this information can be visualized using computer graphics for web apps, mobile-apps, augmented reality, and virtual reality by medical practitioners in education and clinical practices. Additionally, the received information about related experiential case-files using web app, mobile app, augmented reality, and virtual reality by medical practitioners in education and clinical practices.

As another example, the experiential case-files are stored in single or plurality of relational or non-relational databases across a single or plurality of servers. The experiential case-files describe the outcomes of clinical data (e.g. patient age, pain location, physiological signals, vital signs, lab tests, medical imaging results, medication, etc.) to formulate a condition, such as, a diagnosis, treatment, monitoring, and prevention as feedback for how the patient responds, and decisions of the medical practitioner made in the case-files. The experiential case-files are kept in database storage structures including without limitation heap files, hashing buckets, B+ trees, and the like. The format of the data may be implemented in maps, vectors, matrices, and the like, that comprise dictionaries (associated memory), lists (vectors), and the like known by those in the art. The experiential case-files are aggregately store and are accessed using multi-node CPU and GPU's or multi-threaded memory to allow readiness of data in appropriate time-scales. This can be retrieved in sub-seconds, seconds, and tens of seconds from 100 to 1,000, 1,000 to 100,000, 100,000 to 10,000,000, and above experiential case-files. This is to serve 100 to 1,000, 1,000 to 100,000, 100,000 to 10,000,000, and above at a moment. The experiential case files are kept on one or multiple distributes servers of disk size 1 to 100 Mb, 100 Mb to 1 Gb, 1 Gb to 100 Gb, 100 Gb to 2 Tb, and 2 Tb and above. As an example embodiment, the aggregate case-files are growing with more cases. As another embodiment, the experiential case-files are encrypted across a single server farm, or distributed server farm. High computation power is inherently required in distributed computing of large computational sets.

As foregoing and following examples of the methods and systems, the reinforcement learning framework consists of: a medical knowledge state-space, wherein data is entered in a structured way. The state-space for a given set of index data and experiential case data may also be referred to as the environment. The state-space contains a plurality of sub-environments (also referred to as sub-spaces) of information that describe characteristics. Each environment may consist of a plurality of sub-environments, each of which may include one or more sub-sub-environments and so on to define a set of hierarchical structured data. For example, a given medical condition has a sub-environment descriptor (e.g., condition→pain), and sub-sub-environment state-space position that is location (e.g., location→chest-precordial), and a sub-sub-sub environment state space position of pain and sensation (e.g., pain/sensation→severe). The sub-environments and so forth are analogous to a sub-game, such as a hand in poker. Each position of the data assimilation position represents n-dimensions of the environment. The data collection of the experiential case-files may be a collection of structured information, such as found in a medical glossary. The structured terms can receive contextual natural language processing without limitation sentiment analysis, relate to ontologies, and the like.

As an example of the experiential case-files, the data information has properties of the reinforcement learning wherein the scored common factors is based on look behind and/or look ahead in the state-space. Each of the look behind and look ahead is referred to as pathway, which is a series of state transitions to move from one state space to another. The forward looking pathway of potential outcomes is termed look ahead pathway. There are look ahead pathways, which learn about the patient by acquiring new patient data by means of tests, exams, etc. defined by a learning identifier. If the correct pathway is known for a specific diagnosis, this is known as exploitative. In contrast, the ability to test behavior is explorative. The framework thus enables a user to search for exploitative pathways from exploration and differential diagnosis by acquiring new data assimilation.

As one example, there is a policy that directs the patient information minimalist state positions to learn for example, a cardiovascular (CVD) exam for heart attack, e.g., blood pressure, heart-beat, ECG reading, etc. The pathways are analyzed by past pathways, look ahead and look behind pathways, and the experiential case-files with the learning identifier and directed by policies as part of the reinforcement learning framework. In this way, the scored common factors are explainable from the policies. This is an important feature because the system can tailor itself to the particular needs of the patient, hospital, health-system as required. This type of agility and flexibility has been a challenge of machine learning.

As a further example, the experiential case-files are reactive to the collection of data (e.g., longitudinal healthcare data) that may be acquired over time. It is dependent on the integrity of the data itself. To facilitate the methods and systems, the data should be clean and normalized. In an example, inconsistent data is filtered out and the resultant cleaned experiential-case files can be re-examined.

The clinical guidance further allows the medical practitioner to override a clinical guidance decision recommendation. It is also anticipated the physician to ask one or more questions and pose hypotheses as part of a decision process. For example, this is the likely outcome in the following steps, and forward next steps as a look ahead of the learning identifier. This becomes analogous to a Chess game. The ability to reach a state that is similar, the medical practitioner will add this to his or her decision process. It is tested. There are multiple possible paths. One (or sometimes more) is the desired outcome. If the outcome is different from the desired outcome, then there is a change in direction and the process can be repeated.

As yet another example of using the experiential case-files and learning identifier, the look ahead collection of combinatoric decision hypothesis, as each decision hypothesis is a pathway, can generate anticipated turning points which determine when information is not affected by learning data assimilation. This comes up in cases in an example of when the physical exam is not predictive of diagnosis; and additional exams, or blood-work or other testing may be needed. This is anticipated by the learning identifier with look ahead and relate if the experiential case-files physical exam are indicative of a diagnosis or require differential of scoring common factors of experiential case-files. The look ahead has features of policy analysis scenario at next step data assimilation or multiple steps ahead from current state-space for the index case data. For example, a user (e.g., physician) can look for differential from the learning identifier to score common factors of the experiential case-files. The exploration scenario additionally includes different policies to see how the learning identifier scores common factors of the experiential case-files. This way, different hypothesis can be proposed and evaluated.

As a further example, the common factors are able to provide the hypothesis predictive outcome scoring based on determining a relatedness (e.g., correlation) among the foregoing experiential case-files and learning identifier with respect to the patient condition (e.g., defined based on longitudinal patient data for the index case). The scored common factors may be computed, for example, based on measuring from temporal difference of data assimilation in a look behind pathway and/or look ahead pathway from learning identifier, such as according to one or a combination of the following criteria: i) size of overlapping cases, ii) how many times a factor occurs in a similar case based on a particular policy and rewards, iii) dynamical system finding initial states, iv) number of common factors, v) optimizing policy, vi) look ahead to outcomes and adjustment to outcome look behind from outcome to find exploitative pathways to minimize least loss, vii) mapping n-dimensional volume normalized quotient, and viii) relating modern algebraic operations of various sets known by this in the art. The factors include decisions of prior cases by medical practitioners, minimalist states and assimilation, sub-environments, and relatedness of sub-environments, etc. from current and related experiential case-files. A benefit of common factors is the ability to learn from each patient.

By way of example, the common factors update and are updated from feedback with new data assimilation information. The new data assimilation may include tests, exams, patient information or the like. Feedback in the data assimilation creates rewards. The common factors are affected by rewards that precompute to new updated results and search for possible turning points. As yet a further example, the feedback is read using natural language processing for context to offer structured examples as part of speech. As another embodiment, the feedback is read by health sensor (e.g., Internet of Things sensors) using application program interfaces (API's).

In an example, the clinical guidance is implemented as computer program code that provides a virtual doctor's office. This allows a learning identifier to create agents that can request evidence gathering data from external sources that indirectly affect the predictive process. That is, the learning identifier does not itself create agents. Instead, predetermined policy launches an agent when external information is needed to execute the policy. For example, the policy operates as a function of the learning identifier, such as f(li, ei) where f is the policy function, li is the learning identifier and ei are other parameters that specify the nature of the external information required for such policy. Hence they are termed for externalities. In some cases, the clinical guidance may be automated. This may occur in situations when less-skilled healthcare workers can perform clinical tasks without risk, such as, in underserved areas, or in global health settings.

As another example, the clinical guidance can be modified in response to a user input, such as where the user may over-ride a result or decide on testing a different hypothesis (implemented in a look-ahead or look-behind pathway), implementing a different exam, or changing patient information. The methods and systems can evaluate the decision outcome and test predictive value. The look ahead to such outcomes can relate what the likelihood of next steps should be. This can continue and update with each additional data assimilation step in the pathway.

In some examples, methods can use single agents and interacting agents to gather evidence for a next step in the data assimilation in use of reinforcement learning technology, such as may be part of or extend a learning hypothesis strategy. The agent can extract experiential case data of sub-environments reinforcement learning framework and, based on the evidence gathered, the agent can generate scored by common factors using a learning identifier derived from aggregate experiential case-files. The foregoing aspects of the experiential case-files, learning identifier, common factors, are present in the methods.

As a further example of the methods, feedback from one or more sources (e.g., external data sources, a user input, an intelligent agent or the like) can generate agents and interacting agents. Such feedback can be provided at any state of the state space to provide corresponding information that is used as a parameter to compute the next state. The agents are generated as a result of a selected policy. The feedback is the information input from either the user of an agent) that search for evidence to be gathered to find next steps of what information to gather. The evidence gathering information represents without limitation patient information, exam, test, patient information, case study from the literature to review, contacting a doctor or specialist for feedback, cost of medication, access to equipment, time considerations and the like. One example of feedback that can be provided by agents is that for of an acute condition. The feedback can include guidance in the form of actions to be considered, such as: Should the patient receive an immediate PCI, or is there time for a potential STEMI or Aortic Dissection where time and access to CT rule out differential diagnosis? This could be the EMT and/or physician. In another example, medical practitioners receive results of an analysis of pharmaceutical cost versus side effects.

As a further example of the methods disclosed herein, request guidance of a decision by the doctor can implement a policy-generating agent that is programmed to analyze and, in some cases, change what policies were previously reviewed. This can become needed, for example, in situations when predictive decisions of current policies are not getting positive feedback, or when scoring of common factors are much higher when analyzing other policies for hypothesis testing than hypothesis testing for the current policies. The medical practitioner can present their case and the practitioner can observe (e.g., in real-time) to accept the test, or ask for more data from another test. The methods allow for medical practitioners to guide decisions based on consensus as a policy that may come up for certain conditions.

As another example of the methods disclosed herein, feedback is read by one or more health sensors, such as may be connected to the systems and methods as Internet of Things (IOT) sensors using API's, such as API's known by those the art. Additionally, the feedback in the data assimilation can be utilized to create rewards, such as be a single, n-dimensional map.

As further examples of the methods, natural language processing can be utilized to read and further guide the evidence gathering of natural language inputs. For example, the information is in the form of structured, semi-structured language and referenced in a database as a matrix, hash, and the like. As an example, the feedback is read using natural language processing for context of patient offering structured examples as parsable speech fragments.

In some examples, methods use meta learning to create sub-environments of state-space parameters from longitudinal data and to, in turn, determine if the set of experiential case-files offer evidence for performing a next step in the data assimilation for a given index case. For example, meta learning can be a machine learning technique that learns from information and processes that provides information about other data. There is a classification of type of learning and from experiential case-files to then learn from. This can be seen as analogous to poker, where you can identify the strategy of the type of player and search that, or a robot how to pick up a block using a robot hand. Then, they use that knowledge when trying to learn how to arrange block. The foregoing aspects of the experiential case-files, learning identifier, common factors are included in the present methods disclosed herein.

As another example, the meta learning can be applied to index case data and experiential data to provide minimalist states and related information of the patient index case. The meta learning provides an explanation of the patient case, surgery, and the like, which relate how guidelines are performed and which information is valid casual inference: type of surgery, environmental impact on mental health, and particulars of a patient. The longitudinal data are predictors for disease. An example is nutrition information between doctor appointments that can be collected from integrated mobile app reminders and incorporated with other data assimilation into patient longitudinal data. The longitudinal data represents information from meta learning of patients of scored common factors in conditions, that seek agents and interacting agents (e.g., intelligent agents that interact with each other) to understand the environment. For example, one agent is programmed to find side effects given a specific drug. If that information is not available locally, the system can launch another agent to find that information. This other agent, in some cases, might have to interact with several sources of data (e.g., various insurance companies, government or research databases). Some of these sources have an API to provide such information. Other data sources may have agents who would rendezvous with the internal intelligent agent in the present system. Ultimately, the internal agent provides the requested information or not, if it is unavailable. In an example, the longitudinal data is requested and retrieved by automated processes.

As further aspect of the methods, the longitudinal data represent information of meta learning of patients of scored common factors in conditions that are pre-computed. The information guides the decision hypothesis of what the next information to be requested. The conditions of the patients learning are grouped to gather minimalist states, and probe for additional information. Policies are determined from the precomputed information from longitudinal data from desired outcomes, condition types, and statistical inference of behavior of condition. The longitudinal data is used for understanding if the meta learning cases are in the right sub-space.

As further aspect of the methods, there is one or multiple software agents computing and processing analysis of the learning identifier for identification of the healthcare practitioner, e.g., exploration, exploitation of pathways for data assimilation accumulation and outcome, which contextualizes the patient case-file, and updates the contextualization with each new state to identify the learning hypothesis of the healthcare practitioner decisions from prior states. The clinical guidance healthcare practitioner hypothesis reason learning identifier pathway analysis is automated or by policy in the reinforcement learning framework to identify aspects of the diagnosis, treatment, and longitudinal monitoring of environment, sub-environment, and sub-sub-environment inclusive from differential analysis, population health metrics, and longitudinal learning identifier for early prevention and monitoring. This contextualization of reasoning the processing analysis is automated by the clinical guidance software in the forum of a relational and non-relational database in document tabular form, and relating this information with the similar case-files clinician (healthcare practitioner) notes as a natural language corpus to evaluate the patient case-file using the state of art natural language processing machine learning software methods known to those in the art for add known sentences, paragraph structure, and mapping the patient case-file using a template case-file. The contextualization of reasoning for the processing of analysis is evaluated and can be modified by the healthcare practitioner and software recommender in a team based care by one or more healthcare practitioners describing additional software request for other team healthcare practitioner members, e.g., LPN, RN, NP, PA, and the like, or digitally mobile health apps, medical devices, and the like, or a combination thereof for healthcare information in the software clinical guidance to include in the environment.

As an example embodiment, the medical criteria is policy in the reinforcement learning framework as medical criteria for particular software agent processing. As another embodiment, the healthcare practitioners in a team based care state environment is partitioned, and the contextualization of the reasoning of multiple practitioners from the learning identifier the analysis each individual and combined with updates in the environment, sub-environment, and sub-sub environment as a continuous health record of the patient.

As another embodiment, the what-if scenarios using look ahead and look behind information is included as a contextualization of reasoning for findings by recording in the database based on the what-if scenarios, which are used to monitor, treat, and guide the patient.

By way of example, the template maps from a non-relational database linker to the environment, sub-environment, and sub-sub environment, etc. that from the learning identifier to identify the patient case-file to generate the environment, sub-environment, and sub-sub environment identification of the case file for minimization of states to be inputted by the healthcare practitioner, and lists a language ontologies from the template mapper for the case-file and specific update of ontologies used by healthcare practitioner language linked back to the the template. This template is further used in a team-based care for defining what state space is allowed and useful by the other healthcare practitioner or digital health app using generated open API information developers can add mobile health app and regular information. The healthcare practitioners can request additional information to form their own template in their partitioned database linked to a higher level non-relational database. As an example embodiment, the clinician note contain tags in the note linking to the higher level database or healthcare practitioner partitioned data based. The patient case file is converted to the language of the template when stored in the case file, and the normalization of longitudinal similar case-files link to the language of the templates and converted to the language of the healthcare practitioner as a means of maintaining a consistent language mapping by different healthcare practitioners.

By way of example, the recommender is shown in the display of a laptop, mobile electronic device, including cellphone, augmented reality, and the like, as part of the user interface, which the user selects the command, physical motion from hand or eye, touch screen, and wherein the information opens graph patient analysis, word analysis, alerts, and from the clinical guidance maps, such as, current diagnosis and future pathways with analysis of the patient. An alert as an example embodiment, is a web socket or API protocol. The recommender is configurable to information display that is acute, outcomes of similar patient case files from surgery, nutrition guidance and impact on health, and the like useful by those known in the art. Data entry of the information understands the relationship for ontologies, medical and healthcare abbreviations, numbers, and values, and the like during data entry for each user through continuous training relating to the template, and how they link as the user modifies the data record, and relates other crowd source users to find similarities of how the healthcare practitioner inputs the data. This information can be mapped back to the original template for universal language of healthcare practitioners to review by linking from one database to another.

As an aspect, the clinical guidance is used in a team based care, wherein multiple clinical guidance collaborate, observe each other screens, send and receive information, and allow particular information seen by the clinical guidance tool from one team based care member to another. The information of the team based care is encrypted from each user, the patient gives access for each team based member to receive open encryption to observe particular aspects of their healthcare. This includes home healthcare duties, hospital, and the like. The data within the database if received by a central server, distributed ledger, and the like is encrypted. Information in the database is encrypted. The encryption methods is private-public including two-factor encryption, physical encryption, such as thumb encryption, and the like known by those in the art. The team based care members have an encryption that opens determine who is able to use the clinical guidance in the team based care. As a particular, the contextualization of the reasoning of the case file from learning identifier automates recommendations and search of billing codes to determine which team based care members do which duties by automating the locking and unlocking of the clinical guidance software.

By way of example, the team based care clinical guidance monitors the healthcare practitioner patient case file to determine what is being learned from the patient, longitudinal data of the patient to re-review education while training of similar case-files if the outcome of the patient were different than tested, or to increase the capacity of the healthcare practitioner by showing competency in case-file evaluation by evaluating new data assimilation and outcomes for diagnosis, treatment, and simulate policies of the medical criteria to actual outcome of the patient case-files, and determining from analysis of exploration and exploitation if the healthcare practitioner was able to properly clinically guide the patient case file.

As an aspect of the foregoing aspects, the clinical guidance is an EHR system with the learning identifier sending and receiving requests for software tools of patient management longitudinal data analysis, longitudinal data monitoring, EHR data collection, population health, educational training, and EHR system billing and clinician (healthcare practitioner notes, and the like by using the software agents using patient case-file information, create API's, the contextualization of the reasoning of the healthcare practitioner decisions, team based care assignments, de-identification of case-file information, what-if scenarios, and similar case-files to perform software command instructions. The software command instructions are API's requests, user-interface component information to display, generating instructions for another learning identifier to request additional clinician guidance, searches, and read by the computer to generate case studies from the available information, and the like. The learning identifier information requests are hard coded rules-based using reinforcement learning framework to guide actions based on the learning identifier data assimilation and outcomes, e.g., diagnosis, treatment and monitoring, wherein the reinforcement learning framework passes actions defining variables and methods to the software tools to one or multitude of software code functions or classes.

As a further example, the software command instructions are non-rule based that use the learning identifier to automate from decisions computationally made from a list of possibilities developed by the learning identifier the information. The software command instructions directly read to the appropriate patient management and EHR system tools, including and without limitation, longitudinal data analysis, billing, clinician (healthcare note), and the like. The EHR System benefits from the clinical guidance of practitioner and knowledge of these decisions from the patient management to perform billing.

As an example, the EHR system has a policy('s) as a medical criteria that defines the healthcare practitioner scope of practice for clinical guidance. The policy is selected by the user or healthcare facility using public-private key encryption.

As a further example, the EHR system, the template maps the patient case file is the API call that is interoperable with additional ontologies and languages from medical and healthcare publicly available data sets including UMLS and the like known by those in the art. The format of the interoperable data is JSON, CSV, and the like, known by those in the art. The EHR system able to integrate disparate sources of patient health information using the team based care methods, whereby using individual and collective learning identifiers of one or multitude of healthcare practitioners in the team based care setting digital workspace to direct healthcare services in parallel.

As an example embodiment, the EHR system will connect the learning identifier to other digital applications to transfer information from their device back into the EHR system to update the learning identifier. This inter connectivity is an API for the learning identifier contextualization of the reasoning for the tests, exams, and monitoring. This information from the learning identifier is defined by the healthcare practitioner for data metrics, for example, nutritional value, or updates on the medication being taken with a health app offered by the pharmaceutical.

As an example, the de-identification where the patient case file identity's will be removed when comparing similarity of case files for each patient where patient case files are kept by tagging an identifier to be removed in the environment, sub-environment, sub-sub environment that is used in the clinician (healthcare practitioner) notes, crowd source similar case files stored in a central or decentralized server, that is or not web-linked, and the like, from the templates, and any ontologies from the particular healthcare practitioner are tagged and removed. The patient case files dates are shifted while maintaining consistency with time separations.

As the foregoing aspect, the longitudinal data experiential case file is dependent on time differences to evaluate linkers to evaluate for the learning identifier of the index patient case-file. The time variable differences for patient encounters, monitoring of the patient, and segmented by entirety of patient, onset of condition, and rates of change of data collection appropriate to the relevance of time relationships, e.g., measuring weight gain repeatedly for COPD patients multi-daily, and measuring weight over a course of six months to reduce the risk of heart condition. The longitudinal data is characterized based on the contextualization of the reasoning from the healthcare practitioners as their longitudinal learning identifier and adding this information into the patient case file. The longitudinal case file is related similarity as an experiential case file search for specific monitoring, inclusive of whole genome and phenotype analysis, patient weight and vitals during monitoring or medical condition, and social and environmental determinant changes with aging.

By way of example, the longitudinal data for primary care healthcare practitioners the experiential case files for specialists that provided a diagnosis and treatment to review, such as a cardiologist, endocrinologist, nutritionist, and the like. The primary care practitioner is able to look at the longitudinal data learning identifier to compare the index patient with similar experiential case-files for look backward and look ahead in the longitudinal data case-file to identify condition progression from primary care patient visits and specialist to compare with the longitudinal learning identifier and risk factors. This is especially useful to provide the information for primary care to find early prevention risk factors.

As will be appreciated by those skilled in the art, portions of the systems and methods disclosed herein may be embodied as a method, data processing system, or computer program product (e.g., a non-transitory computer readable medium having instructions executable by a processor). Accordingly, these portions of the present invention may take the form of an entirely hardware embodiment, an entirely software embodiment, or an example embodiment combining software and hardware. Furthermore, portions of the invention may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments are disclosed herein with reference to flowchart illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in one or more non-transitory computer-readable media that can direct a computer or other programmable data processing apparatus (e.g., one or more processing cores) to function in a particular manner, such that the instructions stored in the computer-readable medium result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks or the associated description.

What are disclosed herein are examples. It is, of course, not possible to describe every conceivable combination of components or methods, but one of ordinary skill in the art will recognize that many further combinations and permutations are possible. Accordingly, the disclosure is intended to embrace all such alterations, modifications, and variations that fall within the scope of this application, including the appended claims.

As used herein, the term includes means includes but not limited to, the term including means including but not limited to. The term based on means based at least in part on. Additionally, where the disclosure or claims recite a, an, a first, or another element, or the equivalent thereof, it should be interpreted to include one or more than one such element, neither requiring nor excluding two or more such elements.

The invention claimed is:

1. A guidance system comprising:
one or more memories configured to store:
a database of a plurality of experiential case file data sets, each experiential case file data set including at least one outcome and state-space parameters that represent an experiential state-space for a respective predetermined patient encounter associated with the at least one outcome; and
an index case file data set that includes state-space parameters representing a state-space for a given patient;
one or more processors configured to access the one or more memories and to execute a reinforcement learning framework comprising:
a master data set generator programmed to generate a master data set by combining the plurality of experiential case file data sets and the index case file data set into a flattened database of state-space parameters that represents an aggregate state-space for the plurality of experiential case file data sets and the index case file data set;
a learning identifier calculator programmed to:
compute a learning identifier that includes a set of common factors based on applying the given index case file with respect to the master data set, each of the common factors in the learning identifier including a weight/score that is calculated to quantify a measure of similarity of each common factor in a current index state-space of index case file data set and the aggregate state-space of the master data set; and
apply a Boolean operator to evaluate the current index state-space of the index case file data set with respect to the aggregate state-space of the master data set;
an action interface configured to receive one or more user-defined actions and/or to set a predetermined policy, the learning identifier calculator being configured to recalculate the learning identifier in response to one or more of the user-defined actions that cause changes in the state-space parameters for the current index state-space, corresponding to a pathway of at least one state change from the current index state-space to a next state-space based on the scored common factors determined by the learning identifier and the predetermined policy and an action parameter describing the at least one state change; and
a reasoning identifier programmed to contextualize decisions of one or more practitioners based on the learning identifier and a similarity of the index case data set and the plurality of experiential case file data sets and to generate a command and/or instruction executable at the action interface, the command and/or instruction executable executed in response to a user input to operate on contextualization for the index case file data set; and
an output device to display user feedback representing at least one of an indication of an expected outcome, a proposed decision, and a proposed intervention according to at least one of the current index state-space and the next-state space for the given patient.

2. The system of claim 1, wherein the flattened database of state-space parameters is a matrix of the state-space parameters.

3. The system of any of claim 1, wherein the learning identifier calculator includes a scoring function that is programmed to compute each of the scored common factors for the learning identifier to indicate a reward to transition to a new state for the index case data set.

4. The system of claim 1, wherein the learning identifier calculator further comprises a pathway analyzer programmed to determine a set of one or more state transitions from an input state of the index case data set that correlate to an exploitive pathway based on the learning identifier computed for each state space along the pathway.

5. The system of claim 4, wherein the pathway analyzer is programmed to compute which actions, corresponding to the set of state transitions, optimize the learning identifier scored common factors for a plurality of different explorative pathways to ascertain the exploitive pathway.

6. The system of claim 5, wherein the pathway analyzer is programmed to evaluate the scored common factors computed by the learning identifier calculator for each state space along each of the plurality of explorative pathways.

7. The system of claim 4, wherein the exploitive pathway corresponds to a desired or hypothesized outcome.

8. The system of claim 1, wherein each experiential case file data set corresponds to an isomorphic mapping of the state-pace parameters for a respective environment.

9. The system of claim 1, wherein the scoring function is programmed to compute the scored common factors for the state-space parameters by measuring at least one of a frequency of all state-space parameters between the master data set and the index case data set, a size of overlapping cases or a number of common factors between the index case data set and the master data set.

10. The system of claim 1, wherein the common factors are updated in response to receiving additional data via the action interface, wherein the additional data includes at least one of feedback provided by a user in response to a user input or sensor data received via an application program interface.

11. The system of claim 1, wherein the state-space for the index case data set and the experiential case data sets comprises a hierarchical arrangement of ordered pairs of isomorphically mapped state-space parameters organized along a pathway.

12. The system of claim 11, wherein the reinforcement learning framework is autonomously placed in the state space, corresponding to a patient environment, sub-environment, and/or sub-sub-environment, according to information type and/or category of the data.

13. The system of claim 1, wherein the learning identifier further comprises a pathway analyzer to analyze, by perturbing or changing one or more state-space parameters for the index case data set to impose at least one state transition on the current state space, the scored common factors being recomputed based on the pathway analysis.

14. The system of claim 13, wherein the pathway analyzer further comprises a look-behind pathway analyzer to analyze the state space for the index case data set by inverting an isomorphic mapping of the state-space parameters associated with the given patient.

15. The system of claim 13, wherein the pathway analyzer further comprises a look-ahead pathway analyzer programmed to analyze the state space for the index case data set by analyzing an isomorphic mapping of the state-space parameters associated with the given patient.

16. The system of claim 13, wherein the changes to index case data set are applied to the state-space parameters through the action interface.

17. The system of claim 1, wherein the reasoning identifier is programmed to update or modify the contextualization of decisions in response to a user input executing the command or instruction.

18. One or more non-transitory computer-readable media having instructions programmed to perform a method when the instructions are executed by one or more processors, the method comprising:

storing in memory a plurality of experiential case file data sets, each experiential case file data set including at least one outcome and state-space parameters that represent an experiential state-space for a respective predetermined patient encounter associated with the at least one outcome;

storing in memory an index case file data set that includes state-space parameters representing a state-space for a given patient;

executing a reinforcement learning framework, the executing comprising:

receiving at an action interface one or more user-defined actions and/or setting a predetermined policy;

generating a master data set by combining the plurality of experiential case file data sets and the index case file data set into a flattened database of state-space parameters that represents an aggregate state-space for the plurality of experiential case file data sets and the index case file data set;

computing a learning identifier that includes a set of common factors based on applying the given index case file with respect to the master data set, each of the common factors in the learning identifier including a weight/score that is calculated to quantify a measure of similarity of each common factor in a current index state-space of index case file set and the aggregate state-space of the master data set;

applying a Boolean operator to evaluate the current index state-space of the index case file data set with respect to the aggregate state-space of the master data set;

contextualizing decisions of one or more practitioners based on the learning identifier and a similarity of the index case data set and the plurality of experiential case file data sets and to generate a command or instruction executable at the action interface, the command/and/or instruction executable executed in response to a user input to operate on contextualization for the index case file data set; and in response to one or more actions that cause changes in the state-space parameters for the current index state-space, recalculating the learning identifier corresponding to a pathway of at least one state change from the current index state-space to a next state-space based on the scored common factors determined by the learning identifier and the predetermined policy and an action parameter describing the at least one state change; and displaying on an output device user feedback representing at least one of an indication of an expected outcome, a proposed decision and a proposed intervention according to at least one of the current index state-space and the next-state space for the given patient.

* * * * *

UNITED STATES PATENT AND TRADEMARK OFFICE
CERTIFICATE OF CORRECTION

| | |
|---|---|
| PATENT NO. | : 11,468,998 B2 |
| APPLICATION NO. | : 16/596267 |
| DATED | : October 11, 2022 |
| INVENTOR(S) | : Yeshaya Koblick and Reuven Koblick |

It is certified that error appears in the above-identified patent and that said Letters Patent is hereby corrected as shown below:

In the Specification

Before the heading "TECHNICAL FIELD", please insert the following paragraph:
-- GOVERNMENT FUNDING
This invention was made with government support under R44MD010495, 3R44MD014095, and 5R44MD014095 awarded by the National Institute of Health. The government has certain rights in the invention. --

Signed and Sealed this
Twenty-ninth Day of November, 2022

Katherine Kelly Vidal
*Director of the United States Patent and Trademark Office*